United States Patent [19]

Lee et al.

[11] Patent Number: 4,921,530
[45] Date of Patent: May 1, 1990

[54] CERTAIN 3,5-PYRIDINE DICARBOXYLATES, THEIR THIO ANALOGUES HAVING HERBICIDAL ACTIVITY

[75] Inventors: Len F. Lee, St. Charles; Maria L. Miller, Manchester, both of Mo.

[73] Assignee: Monsanto Company, St. Louis, Mo.

[21] Appl. No.: 64,647

[22] Filed: Jun. 22, 1987

Related U.S. Application Data

[60] Division of Ser. No. 768,659, Aug. 27, 1985, Pat. No. 4,698,093, which is a continuation-in-part of Ser. No. 668,929, Nov. 6, 1984, abandoned.

[51] Int. Cl.$^5$ .................... C07D 213/55; A01N 43/40

[52] U.S. Cl. .......................................... 71/94; 546/193; 546/194; 546/275; 546/276; 546/278; 546/279; 546/281; 546/291; 546/299; 540/484; 544/124

[58] Field of Search ..................... 546/291, 299; 71/94

[56] References Cited

U.S. PATENT DOCUMENTS 4,692,184  9/1987  Lee ............................................. 71/94

Primary Examiner—Alan L. Rotman
Attorney, Agent, or Firm—James C. Bolding

[57] ABSTRACT

Disclosed herein are 3,5-pyridinedicarboxylic acid derivatives having substituted thio, sulfinyl or sulfonyl substitution at the 4 position which are useful as herbicides and herbicide precursors.

39 Claims, No Drawings

CERTAIN 3,5-PYRIDINE DICARBOXYLATES, THEIR THIO ANALOGUES HAVING HERBICIDAL ACTIVITY

This application is a divisional of copending application Ser. No. 768,659 filed Aug. 27, 1985, Patent No. 4,698,093 which is a continuation-in-part of Application Ser. No. 668,929 filed Nov. 6, 1984, now abandoned.

This invention relates to a new class of 2,6-substituted pyridinecarboxylic acid derivatives having a wide range of activity as herbicides.

Pyridine derivatives have, for many years, been investigated for use in the biological sciences. For example, 2,6-bis(trifluoromethyl)-4-pyridols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent 44,262 there are disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intravenous injection of such compounds. The above described pior art does not disclose pyridines containing both 2-halomethyl and 3-carboxyl groups.

BRIEF DESCRIPTION OF THE INVENTION

It is an object of this invention to provide herbicidal methods and compositions utilizing the novel pyridines of this invention.

Another object of this invention is to provide novel methods for preparing the novel compounds of this invention and novel intermediates useful therein.

The novel compounds of this invention are useful as herbicides or intermediates which can be converted to herbicides and represented by the generic formula

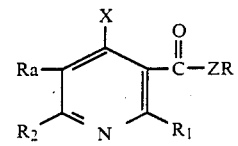

wherein:
R is selected from the group consisting of hydrogen, lower alkyl, lower alkenyl, lower alkynyl, cyanoalkyl, alkoxyalkyl, haloalkyl, haloalkenyl benzyl, phenyl, and a cation, and Z is selected from O and S;

$R_1$ and $R_2$ are independently selected from fluorinated methyl, chlorofluorinated methyl, fluorinated ethyl, and lower alkyl provided that $R_1$ and $R_2$ cannot both be lower alkyl radicals;

Ra is selected from

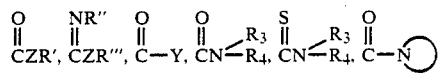

and CN radicals wherein R' is selected from hydrogen, lower alkyl, lower alkenyl, lower alkynyl, cyanoalkyl, alkoxyalkyl, haloalkyl, haloalkenyl, phenyl, benzyl, and a cation; R" and R''' are independently selected from lower alkyl, lower alkenyl, lower alkynyl, cyanoalkyl, alkoxyalkyl, haloalkyl, and haloalkenyl provided that R" may also be hydrogen; $R_3$ and $R_4$ are independently selected from hydrogen, lower alkyl, aralkyl, lower alkenyl, lower alkynyl, haloalkyl, and halo-alkenyl; Y is a halogen selected from F, Cl, and Br; and

is a 3- to 6-membred heterocyclic ring moiety optionally containing one or more additional atoms selected from O, S, and N, and;

X is selected from
(a) a halogen selected from F, Cl, and Br;
(b) —$OR_5$ in which $R_5$ is selected from hydrogen, lower alkyl, lower alkenyl, $C_3$–$C_6$ cycloalkyl, $C_3$–$C_6$ cycloalkylalkyl, haloalkyl, aryl, aralkyl, and a cation;
(c) —$S(O)_nR_6$ in which n is an integer from 0–2 inclusive and $R_6$ is selected from lower alkyl, lower alkenyl, lower alkynyl, $C_3$–$C_6$ cycloalkyl, $C_3$–$C_6$ cycloalkylalkyl, haloalkyl, aryl, and 3 to 7 membered ring saturated and unsaturated heterocycles,
(d)

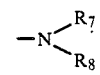

in which $R_7$ is selected from hydrogen, lower alkyl, lower haloalkyl, lower alkenyl, lower alkynyl, and haloalkenyl; and $R_8$ is selected from hydrogen, lower alkyl, lower haloalkyl, lower alkenyl, haloalkenyl, lower alkynyl, aryl, aralkyl, cyanoalkyl, dialkylamino, haloacetyl, $C_3$–$C_6$ halocycloalkylcarbonyl, alkoxycarbonylalkyl, alkoxy, $C_3$–$C_6$ cycloalkyl, $C_3$–$C_6$ cycloalkylalkyl, 3–6 membered ring saturated and unsaturated heterocyclic alkyl, and 3–6 membered ring saturated heterocycles, (e)

in which

is a nitrogen containing saturated or unsaturated 3 to 8 membered heterocyclic ring moiety optionally containing one or more additional atoms selected from O, S, and N, and optionally substituted with one or more groups selected from lower alkyl and epoxy;

(f)

in which $R_9$ and $R_{10}$ are alkoxy;

(g)

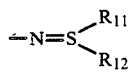

in which $R_{11}$ and $R_{12}$ are lower alkyl;

(h)

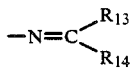

in which $R_{13}$ is trifluoro methyl and $R_{14}$ is halogen, alkoxy, lower alkyl, alkylthio, or dialkylamino;

(i)

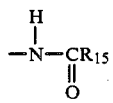

in which $R_{15}$ is haloalkyl;

(j)

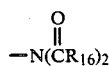

in which $R_{16}$ is alkyl;

(k) —SCN; and (l) —$N_3$.

The terms "lower alkenyl" and "lower alkynyl" herein mean alkenyl and alkynyl groups having 3 to 7 carbon atoms wherein the unsaturation is remote from the moiety attaching the lower alkenyl or alkynyl group to the pyridine ring. Examples of such alkenyl groups include 2-propenyl, 2-butenyl, 3-butenyl, 2-methyl-2-propenyl, and the like. Examples of such lower alkynyl groups include 2-propynyl, and so forth.

The term "lower alkyl" means both straight and branched chain radicals having 1 to 7 carbon atoms, which include, but are not limited to ethyl, methyl, n-propyl, 1-ethylpropyl, 1-methylpropyl, n-butyl, 2,2-dimethylpropyl, pentyl, isobutyl, isopropyl. The term "cycloalkyl" is intended to mean saturated and unsaturated cyclic radicals such as cyclopropyl, cyclobutyl, cyclopentyl, and cyclohexyl.

The term "cycloalkylalkyl" means alkyl radicals substituted with a $C_3$–$C_6$ cycloalkyl radical. The term "haloalkyl" means alkyl radicals substituted with one or more halogen atoms.

The term heterocyclic alkyl means alkyl radical substituted by a 3 to 6 membered heterocyclic radical such as furanyl, tetrahydrofuranyl, and like radicals.

As used herein, "aryl" means a substituted or unsubstituted phenyl radical. Substituents include one or more halogen atoms, nitro radicals, lower alkyl, lower alkoxy, lower haloalkyl, lower haloalkoxy, and carboalkoxy groups.

The term "saturated or unsaturated heterocyclic ring moiety optionally containing one or more additional atoms selected from O, S, and N, and optionally substituted with one or more groups selected from lower alkyl and epoxy" includes radicals such as aziridinyl, piperidinyl, azetidinyl, pyrrolidinyl, hexahydroazepinyl, imidazolyl, pyrrolyl, triazolyl, pyrazolyl, and morpholino, optionally substituted with lower alkyl substituents, as well as radicals such as

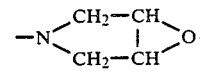

The term "cation" means any cation derived from a base providing a salt. Typical cations include, but are not limited to, alkali metals such as sodium, potassium, and lithium; alkaline earth metals such as calcium, organic amines, and ammonium salts, sulfonium, phosphonium salts, and other salt complexes.

The term "fluorinated methyl" means herein methyl radicals having one or more fluorine atoms attached thereto including radicals wherein all hydrogen atoms replaced by fluorine.

The term "chlorofluorinated methyl" means herein a methyl radical having at least one hydrogen replaced by fluorine and at least one other hydrogen replaced by chlorine.

DETAILED DESCRIPTION OF THE INVENTION

Route 1 below schematically depicts a method whereby the pyridine dicarboxylate compounds of this invention may be prepared from compounds which are readily available commercially, proceeding by way of a pyridine monocarboxylate intermediate. In Route 1, a 3-ketoester of the formula shown is reacted with trifluoroacetonitrile in the presence of a base. Examples of suitable bases are potassium-t-butoxide, sodium, sodium acetate, and the like. The result of this reaction is a 2-acetyl-3-amino-2-alkenoate ester; i.e., an enamine monoester.

The enamine compound so produced is then reacted with 2-2.5 equivalents of a strong base, suitably as lithium diisopropylamine (LDA) in a suitable solvent such as tetrahydrofuran or 1,2-dimethoxyethane to produce a dianion of a structure formula (1). The dianion (1) so produced is then reacted with an ester of a carboxylic acid of the formula shown wherein $R_2$ is selected from trifluoromethyl and chlorofluorinated methyl in which all hydrogens are replaced by chlorine and flourine. The reaction product is a mixture of the substituted 2,3-dihydro-2-hydroxy-4-pyridone (Formula (2)) and 4-hydroxy-2-(trifluoromethyl)-3-pyridinecarboxylate (Formula A), which dehydrates readily when heated to form only the pyridinecarboxylate product.

The 4-hydroxy pyridine monoester compound shown in Formula A may be converted to a 4-alkoxy compound (Formula B) by alkylation with an alkyl halide in the presence of a base. Alkali metal carbonates or hydroxides, amines, and the like, are examples of suitable bases which promote the alkylation reaction.

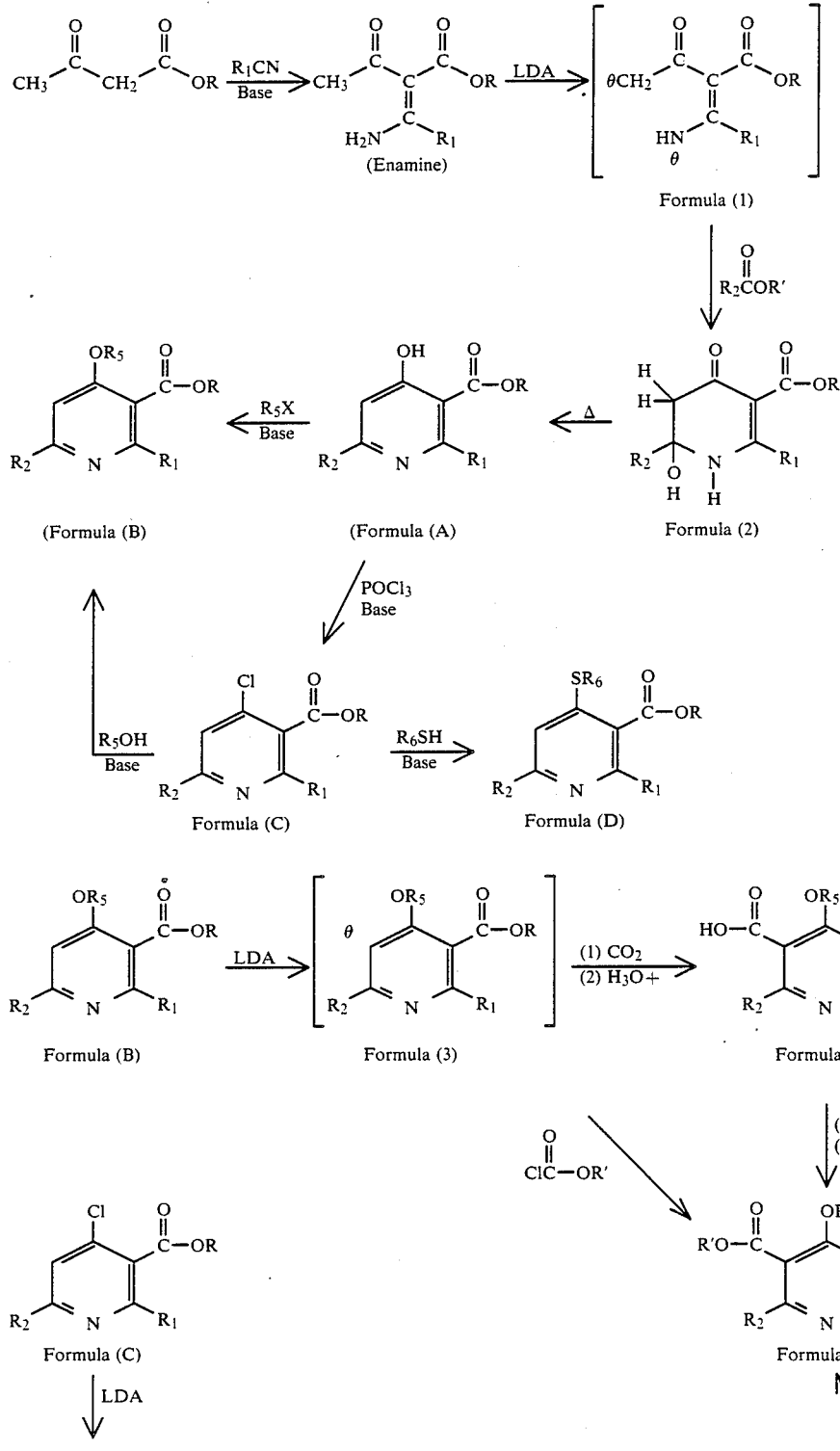

ROUTE 1

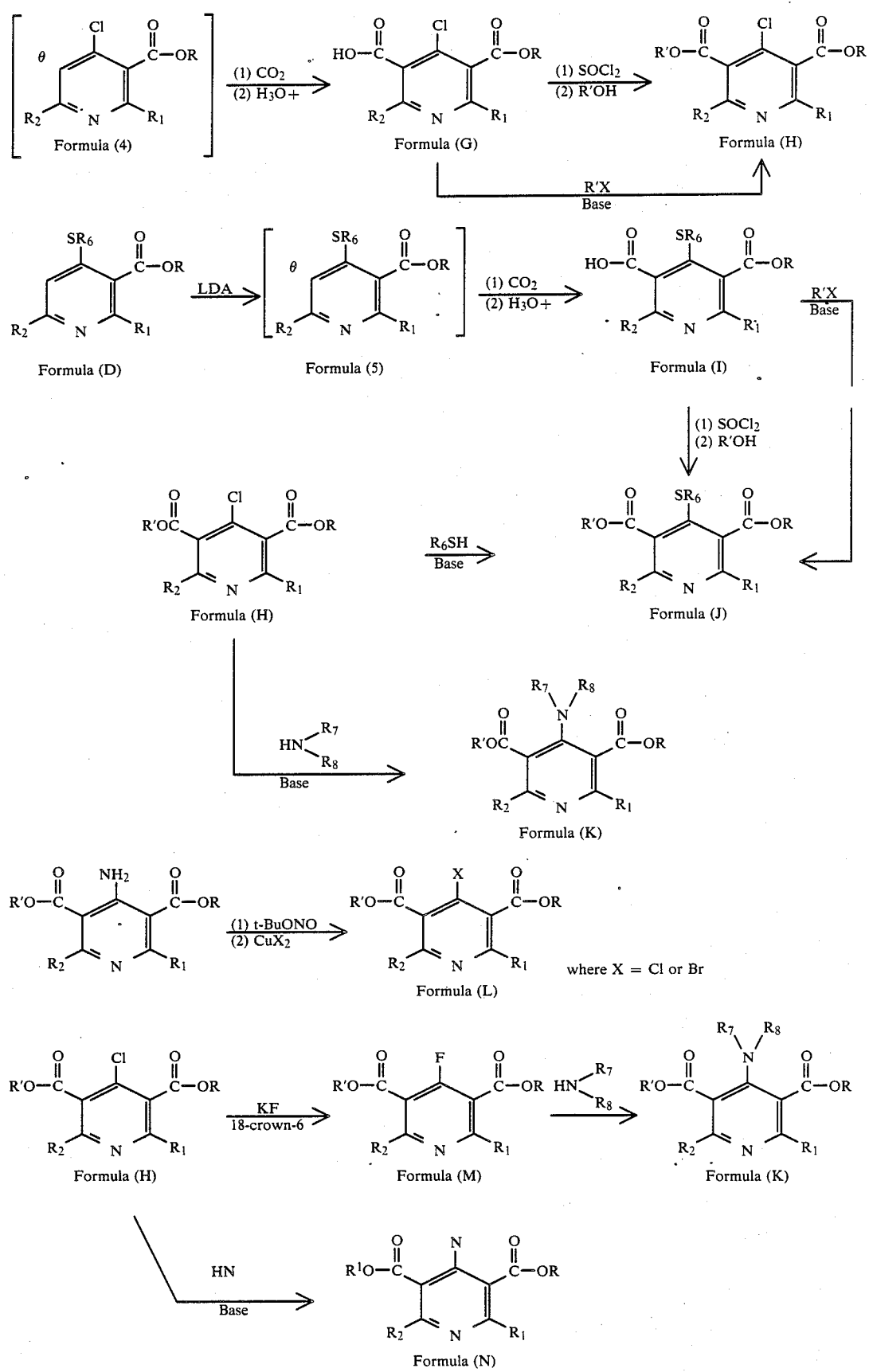

ROUTE 1 -continued

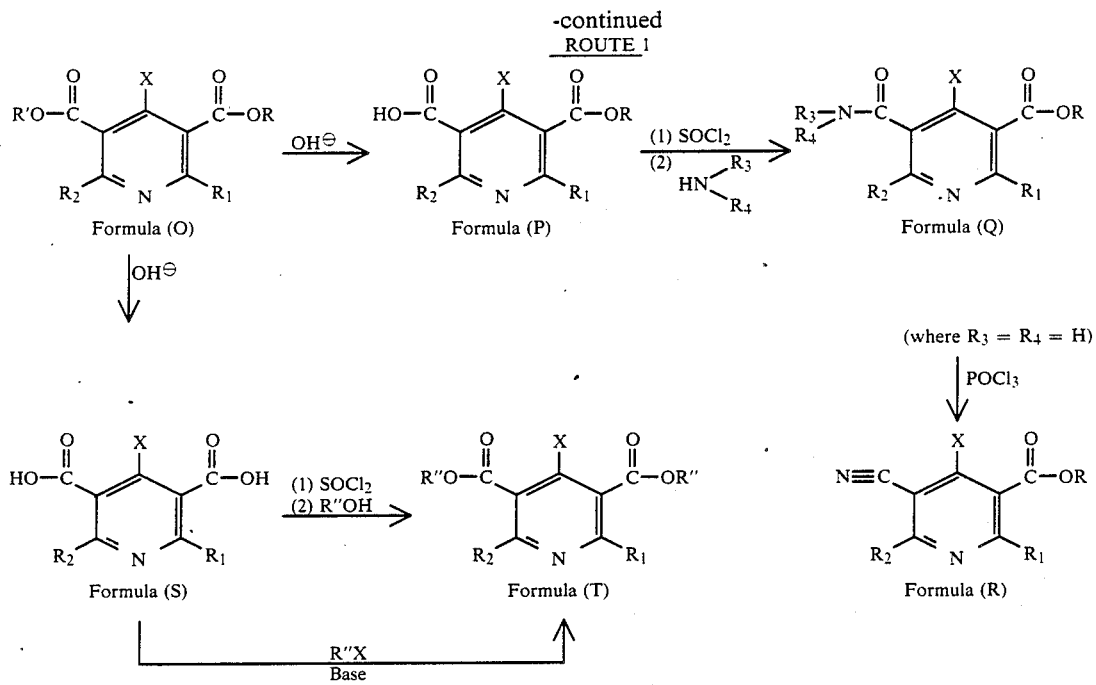

The 4-halo-substituted pyridine monoester intermediate compounds (Formula C) are prepared by reaction of the 4-hydroxy pyridine with a halogenating agent such as phosphorus oxychloride, in the presence of a suitable base. The 4-halopyridines are intermediates in the preparation of compounds of this invention having a sulfur, nitrogen, or oxygen atom substituted at the 4-position on the pyridine ring.

Intermediate compounds with sulfur substitution at the 4-position (Formula D) may be prepared by reaction of the 4-halo compounds with a mercaptan in the presence of a base. The compounds of Formula D may then be oxidized, if desired, to compounds having $-SO_nR_6$ substitution at the 4-position. Suitable oxidizing agents include m-chloroperbenzoic acid.

An alternative means of preparation of oxygen-substituted compounds of Formula B involves the 4-halo-substituted compounds as an intermediate. In this alternate procedure the 4-halopyridine is reacted with a compound having the formula $R_5OH$ in the presence of a base.

Following preparation of the pyridine-monocarboxylate intermediate compounds of Formula B, C, or D, pyridinecarboxylate compounds of the present invention having oxygen, halogen, or sulfur substitution at the 4-position of the pyridine ring (Formula F, H, or J, respectively) may be prepared by first reacting the pyridinemonocarboxylate intermediate compounds of Formula B, C, or D with 1-2 equivalents of LDA to generate an anion of the structure of formula 3, 4 or 5 which then is reacted with carbon dioxide and worked up with diluted hydrochloric acid to generate the acid of a structure formula E, G or I.

The pyridinedicarboxylate monoacids E, G or I may then be reacted with thionyl chloride followed by an appropriate alcohol R'OH to give pyridinedicarboxylates F, H or J. Alternatively, pyridinedicarboxylate monoacids E, G, or I can be alkylated with an appropriate alkyl halide R'X to give pyridinedicarboxylates F, H or J. Alternatively, dicarboxylate compounds of Formula F or J may be prepared from the 4-halo-dicarboxylate (Formula H, L, or M) by reaction with an alcohol or mercaptan compound as in the case of pyridinemonocarboxylates. Dicarboxylates of Formula K having a nitrogen atom substituted at the 4-position may be prepared via the 4-halo-substituted dicarboxylate compounds (Formula H, L, or M) as intermediates by reaction with a primary or secondary amine, a nitrogen containing heterocycle having a hydrogen attached to the nitrogen, an appropriate hydrazine, an alkali metal azide or the like.

Alternatively the pyridinedicarboxylate may be prepared by reaction of the monocarboxylate anion of Formula (3) with an alkyl chloroformate directly.

The 4-halo-substituted pyridinedicarboxylate compounds of Formula L may alternatively be prepared by first diazotizing a 4-amino-substituted pyridinedicarboxylate with a diazotization agent such as t-butyl nitrite followed by reacting the resulting diazonium salt with a copper (II) halide in an appropriate solvent such as acetonitrile. The 4-fluoro-substituted pyridinedicarboxylates of Formula M may be prepared from the corresponding 4-chloro-substituted compound by reaction with metal fluoride, suitably potassium fluoride in a solvent, suitably acetonitrile optionally in the presence of a phase transfer catalyst, suitably 18-crown-6.

The dicarboxylate compounds (Formula O) of this invention may also be transformed to monoacids (Formula P), diacids (Formula S), monoamides (Formula Q), mononitriles (Formula R) and other dicarboxylates (Formula T) by standard synthetic organic methods well known in the arts.

The compounds of this invention wherein X is a dialkoxyphosphonyl, haloalkylamino or haloalkoxy can be preferentially prepared from the corresponding dicarboxylates substituted at the 4-position by a fluorine.

A more preferred method of preparation of pyridine dicarboxylate compounds of the present invention is shown schematically in Route 2 below.

ROUTE 2

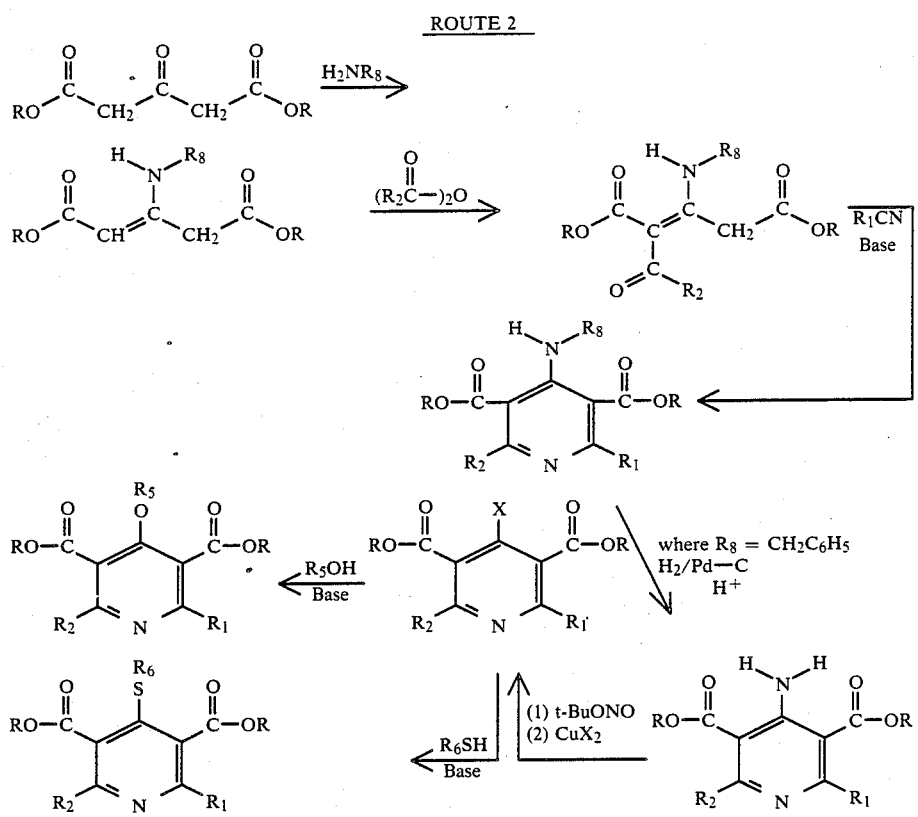

This route employs an enamine diester intermediate and may be employed to make any of the compounds of this invention in which $R_1$ is a halomethyl radical.

In Route 2, a 2-pentene-3-one-dioate ester, also referred to as an acetonedicarboxylate, is reacted with an appropriate primary amine in a suitable reaction medium to provide a 3-amino-2-pentenedicarboxylate (enamine diester). The reaction medium employed in this step is not narrowly critical; the acetonedicarboxylate may be employed alone or a solvent such as an ether may be used. The reaction proceeds smoothly at low temperatures (0°–50° C.) and is exothermic.

In the second step of Route 2, the enamine diester is reacted with a fluorinated or chlorofluorinated alkanoic acid anhydride or fluorinated or chlorfluorinated alkanoyl halide or a mixed anhydride in which one alkyl group is fluorinated or chlorofluorinated and the other is not. In this reaction the fluorinated or chlorofluorinated alkyl moiety becomes the radical $R_2$ in the ultimate pyridinedicarboxylate compound. In this reaction step, suitable solvent media include diethyl ether, THF, and the like with or without a suitable base. Temperatures in the range of about 0° C. to ambient are sufficient for this reaction, although lower or higher temperatures may be used.

The third step of Route 2 involves the reaction of the 2-(fluorinated or chlorofluorinated alkanoyl)-3-amino-2-pentenedicarboxylate produced in step 2 with a perfluorinated or perchlorofluorinated alkylnitrile in the presence of a base to form a 4-aminopyridinedicarboxylate compound of this invention. Suitable bases include but are not limited to triethylamine and DBU. Again, as in step 2 of Route 2, diethyl ether, tetrahydrofuran and 1,2-dimethoxyethane or the like are suitable solvent media. Temperatures of −60° C. to 50° C. are generally sufficient for this reaction step. The 4-aminopyridinedicarboxylate compound of this invention wherein $R_8$ is hydrogen can be prepared from 4-aminopyridinedicarboxylate compound of this invention wherein $R_8$ is benzyl by hydrogenolysis.

The 4-halo-substituted compounds of the invention are conveniently prepared from the 4-amino compounds wherein $R_8$ is hydrogen from the third step of Route 2 by the same manner as in Route 1.

The 4-oxy and 4-thio-substituted pyridinedicarboxylates of this invention are readily prepared from the 4-halo compounds so produced in the same manner as in Route 1. The 4-phosphorus compounds are likewise prepared from the 4-halo compounds, preferably the 4-fluoropyridinedicarboxylate compounds.

Still another process for preparation of compounds of the present invention is shown below in Route 3. In this method, an acetone diester is reacted with magnesium chloride hexahydrate in the presence of a base to form a magnesium chelate compound. This reaction has been reported in Chemical and Pharmaceutical Bulletin 29(5) 1214–1220 (1981). This magnesium chelate is then reacted with a fluorinated or chlorofluorinated acid halide or acid anhydride to form a γ-pyrone in the case in which the 2 and 6 positions are desired to be substituted with the same radical. When the 2 and 6 position substituents are desired to be different, the magnesium chelate is dehydrated by heating and then reacted with an acid halide or an acid anhydride to form a haloalkanoyl-, or alkanoylacetonediester, which is then reacted with a differently-substituted acid anhydride or halide to form a γ-pyrone. In either case, the γ-pyrone is reacted with $NH_3$ to form a 4-hydroxy pyridine compound. The 4-hydroxy pyridine compound can also be prepared by treating the haloalkanoyl- or alkanoylacetonediester with a perhaloalkylnitrile to form the pyridine compound in one step.

fied with the desired alcohol. The benzyl ester group on the CF$_3$ side is then removed by hydrogenolysis using a

ROUTE 3

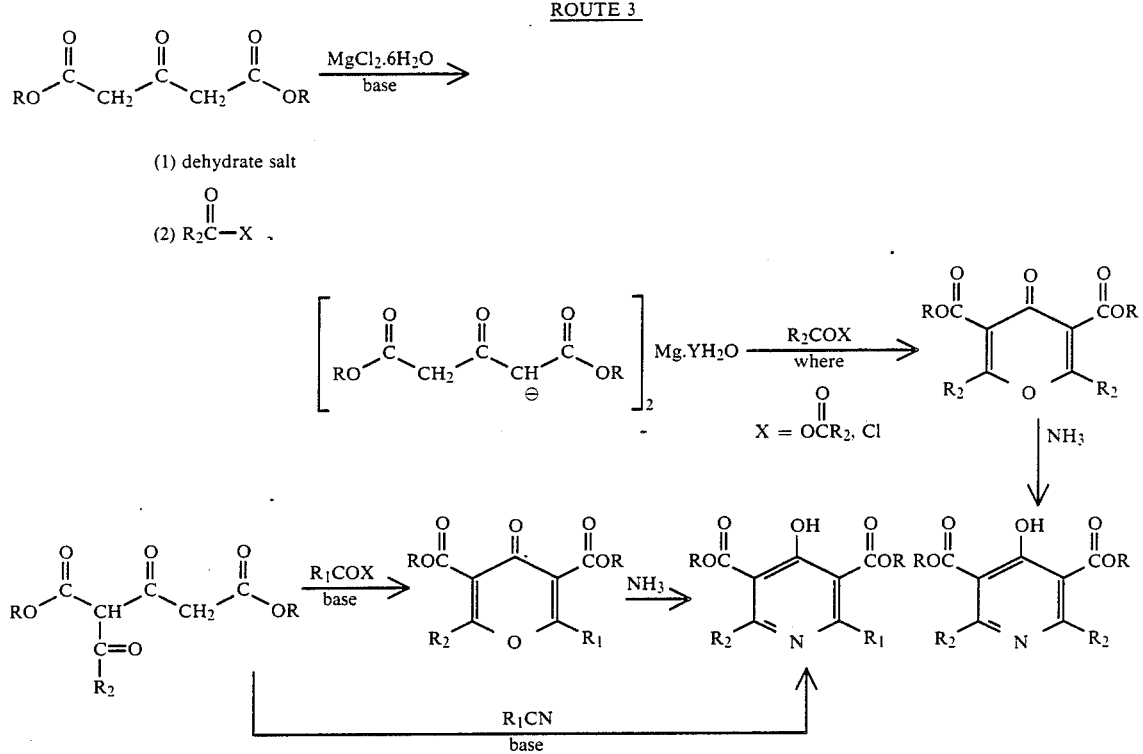

Compounds of this invention in which one (or both) of R$_1$ and R$_2$ is difluoromethyl or fluoromethyl are conveniently prepared from the corresponding pyridinedicarboxylate in which one (or both) of R$_1$ and R$_2$ is chlorodifluoromethyl or dichlorofluoromethyl by hydrogenation using a supported, finely-divided palladium catalyst, a suitable base, and a hydrogen atmosphere. Hydrogen partial pressure of 275 to 1150 kPa are suitable, as are temperatures of about 30° to about 100° C., although none of these values is critical. Ethanol and the like are suitable medium for this hydrogenation reaction. Activated carbon has been found to be a suitable support for the palladium catalyst.

Compounds of this invention in which one of R$_1$ and R$_2$ is trifluoromethyl and the other is methyl are conveniently prepared from the corresponding pyridinedicarboxylate in which one of R$_1$ and R$_2$ is trifluoromethyl and the other is difluoromethyl or fluoromethyl by reduction with metallic zinc in trifluoroacetic acid.

Nitrogen-substituted compounds are conveniently prepared from the 4-halo pyridines by reaction with a primary or secondary amine, an alkali metal azide in the same manner as in Route 1.

Compounds of this invention in which the 5-position is an acid chloride on the same side as the 6-trifluoro methyl group and the 2-position has a difluoromethyl substituent are prepared by reacting a 3,5-diacid pyridine compound with PCl$_5$ to form the diacidchloride, and then reacting the diacidchloride with one equivalent of an alcohol. The alcohol selectively reacts on the same side as the CF$_2$H substituent, forming the desired compound. Alternatively, the diacid may be reacted with a benzyl halide (2 equivalents) in presence of base to form the bis(3,5-benzyl) ester. The benzyl ester group on the CF$_2$H side of the molecule is then selectively hydrolyzed in the presence of a base and then reesterified with the desired alcohol. The benzyl ester group on the CF$_3$ side is then removed by hydrogenolysis using a catalyst such as palladium on carbon. The resulting monoacid is then reacted with PCl$_5$ to form the desired product.

A better appreciation of the present invention will be gained by reference to the following Examples.

As used throughout the specification, including the Examples, the following abbreviations have the following meanings:

LDA—lithium diisopropylamide
THF—tetrahydrofuran
DME—1,2-dimethoxyethane
DBU—1,8-diazobicyclo-[5.4.0]-undec-7-ene
DMF—N,N-dimethylformamide
MCPBA—m-chloroperbenzoic acid
HPLC—high pressure liquid chromatography
TLC—thin layer chromatography
n-BuLi—n-Butyl lithium
DMSO—dimethylsulfoxide
Pd/C—hydrogenation catalyst which is palladium deposited on finely-divided carbon.

PREPARATION OF ENAMINE MONOESTER INTERMEDIATE COMPOUND OF ROUTE 1

EXAMPLE 1

Ethyl 2-acetyl-3-amino-4,4,4-trifluoro-2-butenoate

To a 1 liter, four-necked flask equipped with nitrogen inlet, thermometer, and mechanical stirrer was charged 499.74 g (490 ml, 3.84 mol) of ethyl acetoacetate and 12.9 g (0.115 mol) of potassium-t-butoxide. The resulting mixture was stirred while 391 g (4.04 mol) of trifluoroacetonitrile was added. The reaction mixture was washed with hexane and the resulting solid was dried in vacuo affording 535 g (62%) of the enamine as a yellow solid; mp 63°–65° C.

PREPARATION OF PYRIDINE MONOCARBOXYLATE PRECURSOR COMPOUNDS

The following Examples 2–3 illustrate the preparation of compounds of Formula A in Route 1 by the reaction of an enamine compound from Example 1 with an appropriate fluorinated ester.

EXAMPLE 2

Ethyl 2,6-bis(trifluoromethyl)-4-hydroxy-3-pyridinecarboxylate

To a flame dried, 3-liter, four-necked flask equipped with nitrogen inlet, low temperature thermometer, 500 ml addition funnel and mechanical stirrer was charged 91.0 g (126 ml, 0.899 mol) of diisopropylamine and 500 ml of dry tetrahydrofuran. The resulting solution was cooled to −78° C. using an acetone-dry ice bath. To this was slowly added 383 ml (0.880 mol) of 2.3M n-BuLi in hexane at such a rate that the reaction temperature was kept below −60° C. After stirring at −78° C. for 1 hour, a solution of 90.0 g (0.400 mol) of ethyl 2-acetyl-3-amino-4,4,4-trifluoro-2-butenoate from Example 1 in 150 ml of dry tetrahydrofuran was added at such a rate that the reaction temperature was kept below −60° C. The reaction mixture turned yellow and a solid suspension formed. After 1 hour of stirring at −78° C., the reaction mixture was treated with 184.7 g (155 ml, 1.300 mol) of ethyl trifluoroacetate at such a rate that the reaction temperature was kept below −60° C. This reaction mixture was left at −78° C. for 1 hour, then warmed to room temperature (the yellow suspension disappeared and a brown solution was formed) and stirred for 18 hours. The resulting solution was poured into 1.5 L of 10% HCl (aq.) and extracted 3 times with methylene chloride. The combined methylene chloride layers were dried (MgSO$_4$) and reduced in vacuo affording a brown thick oil. The residue was kugelrohr distilled at 47 Pa. The earlier fraction (pot temperature 50° C.) was discarded. The later fraction (pot temperature 80° C.) afforded 80.0 g (66%) of the pyridine product, mp 70°–77° C.

Anal. Calc'd. for $C_{10}H_7F_6N_1O_3$: C, 39.62; H, 2.33; N, 4.62. Found: C, 39.62; H, 2.37; N, 4.62.

EXAMPLE 3

Ethyl 6-(chlorodifluoromethyl)-4-hydroxy-2-(trifluoromethyl)-3-pyridinecarboxylate This pyridine compound was prepared as described in Example 2, but instead of using ethyl trifluoroacetate, 188 g (1.300 mol) of ethyl chlorodifluoroacetate were reacted affording 75 g (78%) of product after kugelrohr distillation at 60 Pa and pot temperature of 85° C.; mp 56.5°–58.5° C.

Anal. Calc'd. for $C_{10}H_7Cl_1F_5N_1O_3$: C, 37.58; H, 2.21; N, 4.38. Found: C, 37.30; H, 2.19; N, 4.19.

PREPARATION OF 4-ALKOXYPYRIDINE COMPOUNDS from 4-HYDROXY COMPOUNDS

Pyridine monocarboxylate compounds of Formula B shown in Route 1 may be prepared from the 4-hydroxy pyridine compounds of Examples 2–3 above via alkylation using a haloalkyl compound R$_5$X and a basic compound such as K$_2$CO$_3$ as is illustrated in the following Examples 4–8.

EXAMPLE 4

Ethyl 2,6-bis(trifluoromethyl)-4-methoxy-3-pyridinecarboxylate

A mixture of 8.0 g (0.026 mol) of product of Example 2, 3.6 g (0.026 mol) of potassium carbonate, 20 g of methyl iodide, and 50 ml of acetone was held at reflux for 6 hours and concentrated. The residue was treated with water and extracted with ether. The ether extract was washed once with 30 ml of 10% NaOH, dried, and concentrated. The residue was crystallized from hexane to give 6.91 g (82.5%) of product; mp 58.5°–59.5° C.

Anal. Calc'd for $C_{11}H_9F_6N_1O_3$: C, 41.65; H, 2.86; N, 4.42. Found: C, 41.33; H, 2.94; N, 4.36.

EXAMPLE 5

Ethyl 2,6-bis(trifluoromethyl)-4-isopropoxy-3-pyridinecarboxylate

Following the procedure of Example 4, this material was prepared in 74% yield from product of Example 2 and 2-iodopropane as a liquid, n$_D^{25}$ 1.420.

Anal. Calc'd. for $C_{13}H_{13}F_6N_1O_3$: C, 45.23; H, 3.80. Found: C, 45.18; H, 3.79.

EXAMPLE 6

Ethyl 2,6-bis(trifluoromethyl)-4-ethoxy-3-pyridinecarboxylate

This material was prepared following the procedure of Example 4 in 77% yield from product of Example 2 and ethyl iodide as a white solid; mp 57°–59° C.

Anal. Calc'd. for $C_{12}H_{11}F_6N_1O_3$: C, 43.52; H, 3.35. Found: C, 43.56; H, 3.35.

EXAMPLE 7

Ethyl 6-(chlorodifluoromethyl)-4-ethoxy-2-(trifluoromethyl)-3-pyridinecarboxylate This product was prepared as described in Example 4, 25.5 g (0.080 mol) of product of Example 3, 14.3 g (0.103 mol) of K$_2$CO$_3$, 37.5 ml (0.470 mol) of ethyl iodide in 100 ml of acetone were reacted affording 22.86 g of oil which was purified by HPLC using 3% ethyl acetate/cyclohexane as eluting solvent to give 14.73 g of solid. Crystallization in hot hexane gave 11.11 g (41.6%) of solid. A portion (0.98 g) of this solid was kugelrohr distilled at 29 Pa, pot temperature 70° C., to give 0.81 g of product as a white solid; mp 54.5°–56.5° C.

Anal. Calc'd. for $C_{12}H_{11}Cl_1F_5N_1O_3$: C, 41.46; H, 3.20; N, 4.03. Found: C, 41.57; H, 3.23; N, 4.02.

EXAMPLE 8

Ethyl 6-(chlorodifluoromethyl)-4-(isopropoxy)-2-(trifluoromethyl)-3-pyridinecarboxylate A mixture of 15.0 g (0.047 mol) of product of Example 3, 6.5 g (0.047 mol) of K$_2$CO$_3$ and 5.2 ml (0.052 mol) of 2-iodopropane in 100 ml of acetone was stirred at reflux for 64 hours. The cooled reaction mixture was concentrated in vacuo. The residue was dissolved in ether, washed with H$_2$O, dried (MgSO$_4$), and concentrated in vacuo to a brown oil which was kugelrohr distilled at 68 Pa, pot temperature 90° C., affording 15.11 g (88.9%) of product as a clear oil, $n_D^{25}$ 1.4405.

Anal. Calc'd. for $C_{13}H_{13}Cl_1F_5N_1O_3$: C, 43.20; H, 3.62; N, 3.87. Found: C, 43.03; H, 3.66; N, 3.86.

PREPARATION OF 4-HALO-PYRIDINE-MONOCARBOXYLATE PRECURSOR COMPOUNDS

Compounds of Formula C in Route 1 are prepared as precursors for compounds having an O, S, or N atom substituted on the pyridine ring at the 4-position. The 4-halo-substituted compounds are conveniently prepared by treatment of a 4-hydroxy pyridine compound such as from Examples 2 or 3, with a halogenating agent such as $POCl_3$ in the presence of a base. Preparation of these compounds is exemplified in the following Examples 9–10.

EXAMPLE 9

Ethyl 2,6-bis(trifluoromethyl)-4-chloro-3-pyridinecarboxylate

A 500 ml round bottom flask equipped with nitrogen inlet and magnetic stirrer is charged with 40 g (0.132 mol) of product from Example 2 and 24.97 g (0.233 mol) of 2,6-lutidine. To this is slowly added (exothermic) 185 ml (1.98 mol) of phosphorus oxychloride. The flask is fitted with a condenser and the mixture is heated to reflux. After refluxing for 18 hours the material is cooled, concentrated, and the mixture was poured into 150 g of ice slowly. The ice mixture was then poured into 200 ml of 10% HCl (aqueous) and extracted twice with ether. The combined ether layers were washed with 10% NaOH (aqueous), dried (MgSO$_4$), and concentrated in vacuo affording a black oil. The residue was kugelrohr distilled at 67 Pa. The earlier fraction (pot temperature 50° C.) was discarded. The later fraction (pot temperature 85° C.) afforded 25.15 g (60%) of product, $n_D^{25}$ 1.4185.

Anal. Calc'd. for $C_{10}H_6Cl_1F_6N_1O_2$: C, 37.35; H, 1.88; N, 4.36. Found: C, 37.51; H, 1.74; N, 4.23.

EXAMPLE 10

Ethyl 4-chloro-6-(chlorodifluoromethyl)-2-(trifluoromethyl)-3-pyridinecarboxylate This compound was prepared as described in Example 9: 75 g (0.235 mol) of product of Example 3, 50.29 g (55 ml, 0.469 mol) of 2,6-lutidine and 252.66 g (214 ml, 2.3 mol) of phosphorus oxychloride were reacted affording 68 g of a black oil. The crude product was purified by kugelrohr distillation at 200 Pa, pot temperature 110° C., to give 48 g (60%) of product as a yellow oil, $n_D^{25}$ 1.4466.

Anal. Calc'd. for $C_{10}H_6Cl_2F_5N_1O_2$: C, 35.53; H, 1.79; N, 4.14. C, 35.86; H, 2.12; N, 4.16.

PREPARATION OF 4-SULFUR SUBSTITUTED PYRIDINEMONOCARBOXYLATE PRECURSOR COMPOUNDS

The foregoing 4-halo substituted compounds of Examples 9–10 may be employed as intermediates in the preparation of substituted pyridinemonocarboxylate compounds in which the substituent atom at the 4-position on the pyridine ring is selected from O, S, and N. Pyridinemonocarboxylate precursors of compounds according to the present invention, which are substituted by a sulfur atom at the 4-position of the pyridine ring, are prepared by the reaction of the corresponding 4-halo pyridine compound with a thiol in the presence of a base, as illustrated in the following Example 11.

EXAMPLE 11

Ethyl 4-(ethylthio)-2,6-bis(trifluormethyl)-3-pyridinecarboxylate

A mixture of 3.0 g (0.009 mol) of product of Example 9, 1.55 g (0.011 mol) of $K_2CO_3$ and 3.5 ml (0.047 mol) of ethanethiol in 15 ml of methyl isobutyl ketone was stirred at reflux for 60 hours. The reaction mixture was concentrated. The residue was taken up in ether, washed with 10% NaOH and water, dried (MgSO$_4$) and concentrated in vacuo to 2.98 g of dark oil which was purified by HPLC using 5% ethyl acetate/cyclohexane as eluting solvent affording 2.18 g (69.8%) of product as a tan solid; mp 36°–37.5° C.

Anal. Calc'd. for $C_{12}H_{11}F_6N_1O_2S_1$: C, 41.50; H, 3.19; N, 4.03. Found: C, 41.45; H, 3.22; N, 4.01.

PREPARATION OF 4-OXYGEN-SUBSTITUTED PYRIDINEDICARBOXYLATE COMPOUNDS

Pyridinedicarboxylate compounds of this invention having an oxygen atom substituted on the pyridine ring in the 4-position have been prepared in two ways. The first preparative procedure is by carboxylation at the 5-position on the pyridine of a 4-alkoxy-3-pyridinemonocarboxylate from one of Examples 4–8 above, the 4-substituent group being the same in the dicarboxylate compound as in the monocarboxylate. This technique and compounds derived from are illustrated in the following Examples 12–25.

EXAMPLE 12

3-Ethyl 5-methyl 6-(chlorodifluoromethyl)-4-isopropoxy-2-(trifluoromethyl)-3,5-pyridinedicarboxylate To 50 ml of dry THF at −78° C. was added 6.3 ml (0.045 mol) of diisopropylamine followed by 19 ml (0.043 mol) of 2.3M n-butyllithium in hexane. After stirring at −78° C. for 15 minutes, a solution of 13.0 g (0.036 mol) of product of Example 8 in 50 ml of dry THF was added. After stirring at −78° C. for one hour, small pieces of dry ice were added. The addition was stopped when the exotherm ceased. Stirring at −78° C. was continued for 1 hour and then the reaction mixture was allowed to warm up to room temperature in 1½ hour. The reaction mixture was poured into 450 ml of $H_2O$ containing 50 ml of concentrated HCl, extracted with ether, dried (MgSO$_4$) and concentrated in vacuo to a dark oil. This oil, 5.5 g (0.040 mol) of $K_2CO_3$ and 11.2 ml (0.180 mol) of methyl iodide in 125 ml of acetone was refluxed for 17 hours. The cooled reaction mixture was concentrated in vacuo. The residue was poured into water, extracted with ether, dried (MgSO$_4$) and concentrated in vacuo to a dark oil which was kugelrohr distilled at 51 Pa, pot temperature 90° C., to give 11.01 g (72.9%) of product as a yellow oil, $n_D^{25}$ 1.4484.

Anal. Calc'd. for $C_{15}H_{15}Cl_1F_5N_1O_5$: C, 42.92; H, 3.60; N, 3.34. Found: C, 42.71; H, 3.60; N, 3.31.

EXAMPLE 13

3-Ethyl 5-methyl 6-(difluoromethyl)-4-isopropoxy-2-(trifluoromethyl)-3,5-pyridinedicarboxylate A mixture of 3.0 g (0.007 mol) of product of Example 12, 0.72 g (0.007 mol) of triethylamine and 0.36 g of Pd/C (10%) in 30 ml of ethanol was hydrogenated with 501 kPa hydrogen pressure at 50° C. for 1 hour and filtered. The filtrate was concentrated, the residue dissolved in ether, washed with 3.7% aqueous HCl, dried (MgSO$_4$) and concentrated in vacuo to 2.74 g of a brown oil. This oil was kugelrohr distilled at 67 Pa, pot temperature 90° C., to give 2.45 g (90.8%) of product as a yellow solid; mp 29°–31° C.

Anal. Calc'd. for $C_{15}H_{16}F_5N_1O_5$: C, 46.76; H, 4.19; N, 3.64. Found: C, 46.52; H, 4.18; N, 3.61.

EXAMPLE 14

3-Ethyl 5-hydrogen 2,6-bis(trifluoromethyl)-4-ethoxy-3,5-pyridinedicarboxylate This material was prepared in 52.7% yield from 0.06 mol of LDA and 0.024 mol of product of Example 6 according to the following general procedure as a beige solid, mp 115°–117° C. To a −78° C. solution of 2.5 eq (0.06 mol) of LDA in DME was added a solution of 1 eq (0.024 mol) of starting material, the monocarboxylate product (Example 6) in dry DME. The resulting dark colored solution was stirred for 30 minutes at −78° C. To the above solution was added excess of dry ice. The reaction mixture was stirred at −78° C. for 15 minutes and warmed to room temperature in 1 hour. The reaction mixture was poured into ice water (100 ml) and extracted with ether. The aqueous layer was made acidic. The oil precipitate was extracted with ether. The ether extract was dried (MgSO$_4$) and concentrated in vacuo to give the desired product.

Anal. Calc'd. for $C_{13}HHd\ 11F_6N_1O_5$: C, 41.61; H, 2.96. Found: C, 41.62; H, 2.98.

EXAMPLE 15

Diethyl 2,6-bis(trifluoromethyl)-4-methoxy-3,5-pyridinedicarboxyate

To a cold (−78° C.) solution of LDA, from 0.02 mol (2.8 ml) of diisopropylamine, 0.0208 mol of n-BuLi, and 30 ml of DME was added a solution of 4.65 g (0.015 mol) of product of Example 4 in 20 ml of DME. The resulting greenish solution was stirred at −78° C. for 10 minutes and treated with 2.7 ml (0.035 mol) of ethyl chloroformate. The reaction mixture was warmed to room temperature in 40 minutes, then poured into a mixture of 20 ml of concentrated HCl and 50 ml of water. The mixture was extracted with ether (200 ml). The ether extract was dried and concentrated. The residue was kugelrohr distilled at 13 Pa. The earlier fraction (pot temperature 50°–65° C.) was discarded. The later fraction (pot temperature 90° C.) was an oil (5.47 g) which was crystallized from hexane at low temperature to give 4.4 g (75%) of product; mp 46.5°–47.5° C.

Anal. Calc'd. for $C_{14}H_{13}F_6N_1O_5$: C, 43.20; H, 3.37; N, 3.60. Found: C, 43.17; H, 3.37 N, 3.57.

EXAMPLE 16

3-Ethyl 5-methyl-2,6-bis(trifluoromethyl)-4-isopropoxy-3,5-pyridinedicarboxylate 3-Ethyl 4-hydrogen-2,6-bis(trifluoromethyl)-4-isopropoxy-3,5-pyridinedicarboxylate was obtained in 92.8% yield from 0.118 mol of LDA and 0.052 mol of product of Example 5 according to the above general procedure described for Example 14 and was used without further purification. A mixture of 8.0 g (0.020 mol) of the crude acid, 11.67 g (0.082 mol) of methyl iodide and 5.68 g (0.041 mol) of K$_2$CO$_3$ and 200 ml of acetone was held at reflux for 20 hours. The reaction mixture was filtered and concentrated. The residue was dissolved in ether. The ether solution was washed with 20% K$_2$CO$_3$, dried and concentrated to give 7.08 g of an oil which was purified by HPLC using 10% ethyl acetate/cyclohexane as eluant to give 5.36 g (64.7%) of product as an oil, n$_D^{25}$ 1.4308.

Anal. Calc'd. for $C_{15}H_{15}F_6N_1O_4$: C, 44.68; H, 3.75; N, 3.47. Found: C, 45.07; H, 3.70; N, 3.53.

EXAMPLE 17

3-Ethyl 5-methyl 2,6-bis(trifluoromethyl)-4-ethoxy-3,5-pyridinedicarboxylate A mixture of 8.0 g (0.021 mol) of product of Example 14 and 50 ml of thionyl chloride was held at reflux for 1 hour and concentrated. The residue was then refluxed with 50 ml of methanol for 2 days and concentrated. The residue was dissolved in ether. The ether solution was washed with 15% potassium carbonate, dried (MgSO$_4$) and concentrated. The residue was chromatographed by HPLC using 5% ethyl acetate/cyclohexane as eluant to give 4.56 g (55.8%) of product as an oil, n$_D^{25}$ 1.4290.

Anal. Calc'd. for $C_{14}HHd\ 13F_6N_1O_5$: C, 43.20; H, 3.37; N, 3.66. Found: C, 43.27; H, 3.51; N, 3.47.

EXAMPLE 18

3-Ethyl 5-hydrogen 6-(chlorodifluoromethyl)-4-ethoxy-2-(trifluoromethyl)-3,5-pyridinecarboxylate This compound was prepared as described for Example 14, 84 ml of dry THF, 19 ml (0.134 mol) of diisopropylamine, 85 ml (0.129 mol) of 1.53M n-BuLi in hexane, 35.89 g (0.108 mol) of product of Example 7, and small pieces of dry ice were reacted affording a tan solid, which was recrystallized in hot hexane to give 23.84 g (56.4%) of product as a tan solid; mp 81°–83° C.

Anal. Calc'd. for $C_{13}H_{11}Cl_1F_5N_1O_5$ C, 39.86; H, 2.83; N, 3.58. Found C, 39.94; H, 2.85; N, 3.57.

EXAMPLE 19

3-Ethyl 5-methyl 6-(chlorodifluoromethyl)-4-ethoxy-2-(trifluoromethyl)-3,5-pyridinedicarboxylate A mixture of 7.0 g, (0.018 mol) of product of Example 18 and 25 ml of thionyl chloride were stirred at reflux for 2½ hours. Reaction mixture was concentrated and 25 ml of methanol was added, and refluxing was continued for 60 hours. The reaction mixture was concentrated to a dark oil which was kugelrohr distilled at 47 Pa, pot temperature 90° C., affording 6.33 g (87.3%) of product as a yellow solid; mp 37.5°–39.5° C.

Anal. Calc'd. for $C_{14}H_{13}Cl_1F_5N_1O_5$: C, 41.45; H, 3.23; N, 3.45. Found: C, 41.26; H, 3.24; N, 3.41.

EXAMPLE 20

Ethyl 5-aminocarbonyl-2,6-bis(trifluoromethyl)-4-ethoxy-3-pyridinecarboxylate hemihydrate A mixture of 8.0 g (0.021 mol) of product of Example 14 and 10 ml of thionyl chloride was held at reflux until gas evolution ceased. The reaction mixture was concentrated to give an oil. This oil was dissolved in ether (ca 20 ml) and the ether solution was added to 10 ml of liquid ammonia. The resulting solid was collected and washed with hexane to give 8.27 g of a solid. This solid was stirred with 50 ml of ether and 50 ml of 15% $K_2CO_3$ and filtered. The insoluble solid (2.83 g) is believed to be crude product. The ether layer was concentrated to give 5.04 g (61.7%) of purified product, mp 158°–160° C.

Anal. Calc'd. for $C_{13}H_{12}F_6N_2O_4$ [0.5 $H_2O$]: C, 40.74; H, 3.46; N, 7.31. Found: C, 40.73; H, 3.19; N, 7.04.

EXAMPLE 21

Diethyl 2,6-bis(trifluoromethyl)-4-ethoxy-3,5-pyridinedicarboxylate

This material was obtained from product of Example 14 and ethanol according to the following general procedure: A 5.0 g portion of the acid product of Example 14 was refluxed with excess thionyl chloride until the reaction was completed. Excess thionyl chloride was removed in vacuo. The residual acid chloride was refluxed with an excess of appropriate alcohol (ethanol in this Example) for 2–4 hours and concentrated to give the desired product. The crude product was purified by a wash with 20% $K_2CO_3$ and isolated as a solid (20.3% yield), mp 28°–30° C.

Anal. Calc'd. for $C_{15}H_{15}F_6N_1O_5$: C, 44.68; H, 3.75 N, 3.47. Found: C, 44.24; H, 3.66 N, 3.57.

EXAMPLE 22

3-Ethyl 5-methyl 6-(difluoromethyl)-4-ethoxy-2-(trifluoromethyl)-3,5-pyridinedicarboxylate (0.2 hydrate)

A mixture of 5.0 g (0.012 mol) of product of Example 19, 1.72 ml (0.012 mol) of triethylamine and 0.75 g of 10% Pd-C in 65 ml of ethanol was hydrogenated at 40° C. under 522 kPa of $H_2$ pressure for 18 hours. The reaction mixture was filtered through celite and concentrated. The residue was taken up in ether, washed with 10% HCl (aq), dried (MgSO4) and concentrated in vacuo to 3.28 g of yellow solid, which was recrystallized in hot hexane to give 2.13 g (47.4%) of product as a light yellow solid, mp 59°–61° C.

Anal. Calc'd. for $C_{14}H_{14}F_5N_1O_5$ [0.2 $H_2O$]: C, 44.86; H, 3.87; N, 3.74. Found: C, 44.84; H, 3.55; N, 3.71.

EXAMPLE 23

Dimethyl 6-(difluoromethyl)-4-(isopropoxy)-2-(trifluoromethyl)-3,5-pyridinedicarboxylate A solution of 4.3 g (0.011 mol) of product of Example 13, 8.6 g (0.154 mol) of KOH and 50 ml of $H_2O$ in 125 ml of methanol was refluxed for two days and then stirred at room temperature for 2½ days. The reaction mixture was poured into 250 ml of water containing 50 ml of concentrated HCL, extracted with ether, dried (MgSO4) and concentrated in vacuo affording 3.06 g of white solid. This solid, 4.4 g (0.032 mol) of $K_2CO_3$ and 4.0 ml (0.065 mol) of methyl iodide in 50 ml of DMF was stirred at room temperature for 4½ hours. Reaction mixture was poured into 10% HCl, extracted with ether, dried (MgSO4) and concentrated in vacuo to an orange oil which was kugelrohr distilled at 47 Pa, pot temperature 100° C., affording 1.90 g (39.4%) of product as a yellow solid; mp 41°–42° C.

Anal. Calc'd. for $C_{14}H_{14}F_5N_1O_5$: C, 45.29; H, 3.80; N, 3.77. Found: C, 45.38; H, 3.83; N, 3.76.

EXAMPLE 24

Dimethyl 2-(difluoromethyl)-4-hydroxy-6-(trifluoromethyl)-3,5-pyridinedicarboxylate The product from Example 18 (12.34 g, 0.032 mol), 9.0 ml (0.064 mol) of triethylamine and 0.62 g of Pd-C (10%) in 100 ml of ethanol were reacted as described in Example 22 above affording 9.99 g of dark orange oil. A portion of this oil (5.0 g, 0.014 mol), 4.51 g (0.070 mol) of 87% KOH, 1 ml of $H_2O$ in 30 ml of ethanol was stirred at reflux for 5 days. The reaction mixture was concentrated and the residue was poured into water and washed with ether. The aqueous layer was acidified with concentrated HCl, extracted with ether, dried (MgSO4) and concentrated in vacuo to 4.26 g of foamy oil, which was further treated as described in Example 19; 4.26 g (0.013 mol) of this foamy oil and 25 ml of thionyl chloride were reacted. The resulting acid chloride was reacted with methanol to afford a dark solid residue which was taken up in ether and extracted with 15% of $K_2CO_3$ and water, acidified with concentrated HCl, extracted with ether, dried (MgSO4) and concentrated in vacuo to 2.7 g of solid. Recrystallization in hot hexane-ether afforded 1.37 g (32.0%) of product as a tan solid; mp 83°–84.5° C.

Anal. Calc'd. for $C_{11}H_8F_5N_1O_5$: C, 40.14; H, 2.45; N, 4.26. Found: C, 40.00; H, 2.47; N, 4.23.

EXAMPLE 25

Ethyl 2,6-bis(trifluoromethyl)-5-cyano-4-ethoxy-3-pyridinedicarboxylate

A mixture of 4.0 g (0.011 mol) of product of Example 20 and 100 ml of phosphorus oxychloride was held at reflux for 7 hours and concentrated in vacuo. The residue was poured into water and extracted with ether. The ether extract was washed with 15% aqueous $K_2CO_3$, dried (MgSO4) and concentrated to give 1.43 g (37.6%) of product as an oil, $n_D^{25}$ 1.4370.

Anal. Calc'd. for $C_{13}H_{10}F_6N_2O_3$: C, 43.83; H, 2.83; N, 7.86. Found: C, 43.82; H, 2.79; N, 7.86.

PREPARATION OF 4-HALO PYRIDINEDICARBOXYLATE DERIVATIVES FROM 4-HALOMONOCARBOXYLATES

Pyridinecarboxylate derivatives of this invention substituted with a halogen in the 4-position may be prepared by carboxylation of monocarboxylates having the same 4-halogen such as those of Examples 9–10 above. Examples of this preparation method and compounds derived from are shown in the following Examples 26–30.

EXAMPLE 26

3-Ethyl 5-hydrogen 2,6-bis(trifluoromethyl)-4-chloro-3,5-pyridinedicarboxylate

To a −78° C. solution of LDA (0.128 mol) in 85 ml of DME was added a solution of 18.28 g (0.057 mol) of product of Example 9 in 20 ml of DME. The reaction mixture was stirred at −78° C. for 1 hour. To the above solution was added excess of dry ice. After stirring at −78° C. the reaction mixture was warmed to room temperature in 1 hour and poured into 250 ml of water containing 50 ml of concentrated HCl. The oil precipitate was extracted into ether. The ether extract was extracted with saturated NaHCO$_3$. The basic extract was made acidic with concentrated HCl. The oil precipitate was extracted into ether. The ether solution was dried (MgSO$_4$) and concentrated in vacuo to give 7.81 g (37.6%) of product as a solid; mp 113°–115° C.

Anal. Calc'd. for $C_{11}H_6Cl_1F_6N_1O_4$: C, 36.14; H, 1.65; N, 3.83. Found C, 36.54; H, 1.70; N, 3.89.

EXAMPLE 27

3-Ethyl 5-methyl 2,6-bis(trifluoromethyl)-4-chloro-3,5-pyridinedicarboxylate

A mixture of 5.0 g (0.014 mol) of product of Example 26 and 50 ml of thionyl chloride was held at reflux for 2 days and concentrated. The residue was held at reflux with 50 ml of methanol for 24 hours and concentrated. The residue was dissolved in ether. The ether solution was dried (MgSO$_4$) and concentrated to give 2.75 g (53%) of product as a solid; mp 46°–48° C.

Anal. Calc'd. for $C_{12}H_8Cl_1F_6N_1O_4$: C, 37.96; H, 2.12; N, 3.69. Found: C, 37.67; H, 2.09; N, 3.77.

EXAMPLE 28

3-Ethyl 5-methyl 4-chloro-6-(chlorodifluoromethyl)-2-(trifluoromethyl)-3,5-pyridinedicarboxylate To 90 ml of dry THF at −78° C. was added 20 ml (0.142 mol) of diisopropylamine followed by 90 ml (0.137 mol) of 1.53M n-butyllithium in hexane. After stirring at −78° C. for 20 minutes, a solution of 38.55 g (0.114 mol) of product of Example 10 in 40 ml of dry THF was added. After stirring at −78° C. for 1 hour, small pieces of dry ice were added. The addition was stopped when the exotherm ceased. Stirring at −78° C. was continued for 1 hour and then at room temperature for 60 hours. The reaction mixture was poured into H$_2$O and washed with ether. The ether was extracted with 15% K$_2$CO$_3$ and H$_2$O and the combined aqueous layers were acidified with concentrated HCl. The precipitate was extracted with ether, dried (MgSO$_4$) and concentrated in vacuo to 22.02 g of brown solid. This solid, 22.02 g (0.058 mol), 12 g (0.086 mol) of K$_2$CO$_3$ and 18 ml (0.288 mol) of methyl iodide in 100 ml of acetone was refluxed for 17 hours. The cooled reaction mixture was concentrated in vacuo. The residue was dissolved in ether, washed with 15% K$_2$CO$_3$, dried, and concentrated in vacuo to 18.23 g of dark semi-solid oil. Purification by HPLC using 4% ethyl acetate/cyclohexane as eluating solvent afforded 14.51 g (63.29%) of product as a white solid; mp 57.5°–59.5° C.

Anal. Calc'd. for $C_{12}H_6Cl_2F_5N_1O_4$: C, 36.39; H, 2.04; N, 3.54. Found: C, 36.25; H, 2.20; N, 3.49.

EXAMPLE 29

Diethyl 2,6-bis(trifluoromethyl)-4-chloro-3,5-pyridinedicarboxylate

To a cold (−78° C.) solution of LDA, from 0.0155 mol of n-BuLi, 0.0157 mol (2.2 ml) of diisopropylamine and 30 ml of dry DME was added a solution of 3.2 g (0.01 mol) of product of Example 9 in 5 ml of DME. The resulting purple solution was stirred for 5 minutes and treated with 4 ml of ethyl chloroformate. The mixture was stirred at −78° C. for 10 minutes, the cooling bath was removed, and the reaction mixture was stirred for an additional 30 minutes, then poured into water. The mixture was extracted with ether. The ether extract was washed with 50 ml of 3N HCl, dried, and concentrated. The residue was kugelrohr distilled at 53 Pa. The low bp distillate (pot temperature 50°–60° C.) was identified as ethyl N,N-diisopropylurethane. The higher bp distillate (pot temperature 100° C.) was 1.64 g of a solid which was recrystallized from hexane at low temperature to give 1.2 g (30%) of product; mp 76°–77° C.

Anal. Calc'd. for $C_{13}H_{10}Cl_1F_6N_1O_4$: C, 39.66; H, 2.56; Cl, 9.01; N, 3.56. Found: C, 39.73; H, 2.56; Cl; 9.08; N, 3.55.

EXAMPLE 30

Diethyl 4-chloro-6-(chlorodifluoromethyl)-2-(trifluoromethyl)-3,5-pyridinedicarboxylate The material was prepared by the method shown in Example 28: 20.0 g (0.052 mol) of crude monoacid, 8.0 g (0.058 mol) of K$_2$CO$_3$ and 12.6 ml (0.157 mol) of ethyl iodide in 100 ml of acetone were reacted affording 17.51 g of a dark oil. Crude product was purified by HPLC using 1% ethyl acetate/cyclohexane as eluting solvent to give 10.04 g (47%) of product as a beige solid; mp 45°–47° C.

Anal. Calc'd. for $C_{13}H_{10}Cl_2F_5N_1O_4$: C, 38.07; H, 2.46; N, 3.42. Found: C, 37.97; H, 2.48; N, 3.37.

PREPARATION OF 4-SULFUR-SUBSTITUTED PYRIDINEDICARBOXYLATE DERIVATIVES

Pyridinedicarboxylate derivatives which are substituted with a sulfur atom at the 4-position may be prepared in either of two ways; they may be made by reaction of the corresponding 4-chloro-pyridinedicarboxylate derivative with an alkali metal derivative of a thiol, or they may be obtained by carboxylation of the corresponding 4-sulfur substituted monocarboxylate. These two methods and compounds derived from them are illustrated in the following Examples 31–36.

EXAMPLE 31

3-Ethyl 5-methyl, 6-(chlorodifluoromethyl)-4-isopropylthio-2-(trifluoromethyl)-3,5-pyridinedicarboxylate Sodium (0.06 g, 0.0025 mol) was dissolved in 6 ml of methanol. To this was added 0.26 mol (0.0028 mol) of 2-propanethiol. The resulting solution of the sodium salt of the thiol compound was added to 1.0 g (0.0025 mol) of product of Example 28 in 8 ml of methanol at 0° C. The temperature rose about 3° C. and then the reaction mixture was allowed to warm up to room temperature. After 1 hour the reaction mixture was poured into water, extracted with ethyl acetate, washed with 10%

HCl, dried (MgSO$_4$) and was concentrated in vacuo to a yellow oil. This oil was kugelrohr distilled at 47 Pa, pot temperature 96° C., affording 0.63 g (57.8%) of product as a yellow oil, n$_D^{25}$ 1.4700.

Anal. Calc'd. for C$_{15}$H$_{15}$Cl$_1$F$_5$N$_1$O$_4$S$_1$: C, 41.34; H, 3.47; N, 3.21. Found: C, 41.07; H, 3.32; N, 3.20.

EXAMPLE 32

3-Ethyl 5-methyl 6-(difluoromethyl)-4-isopropylthio-2-(trifluoromethyl)-3,5-pyridinedicarboxylate A mixture of 4.51 g (0.01 mol) of product of Example 31, 1.44 ml (0.01 mol) of triethylamine and 0.25 g of 10% Pd/C in 50 ml of ethanol were hydrogenated as described in Example 22, giving 4.6 g of an oil. The crude mixture was purified by HPLC using 3% ethyl acetate/cyclohexane as eluting solvent to give 2.87 g of an oil. This oil was kugelrohr distilled at 102° C./40 Pa affording 2.61 g of a light yellow oil, n$_D^{25}$ 1.4676.

Anal. Calc'd. for C$_{15}$H$_{16}$F$_5$N$_1$O$_4$S$_1$: C, 44.89; H, 4.02; N, 3.49. Found: C, 44.75; H, 4.00; N, 3.47.

EXAMPLE 33

3-Ethyl 5-methyl 4-ethylthio-2,6-bis(trifluoromethyl)-3,5-pyridinedicarboxylate This material was prepared as described in Example 11: 3.36 g (0.009 mol) of product of Example 27, 0.86 g (0.006 mol) of K$_2$CO$_3$ and 12 ml (0.180 mol) of ethanethiol in 25 ml of acetone were reacted affording an orange oil which was kugelrohr distilled at 33 Pa, pot temperature 79° C. to give 2.11 g (58.8%) of product as a clear oil, n$_D^{25}$ 1.4507.

Anal. Calc'd. for C$_{14}$H$_{13}$F$_6$N$_1$O$_4$S$_1$: C, 41.49; H, 3.23; N, 3.46. Found: C, 41.53; H, 3.27; N, 3.46.

EXAMPLE 34

3-Ethyl 5-methyl 4-(ethylsulfinyl)-2,6-bis(trifluoromethyl)-3,5-pyridinedicarboxylate To a 0° C. solution of 4.8 g (0.012 mol) of product of Example 33 in 30 ml of CH$_2$Cl$_2$ was added 4.08 g (0.024 mol) of MCPBA. The reaction was monitored by TLC. The reaction mixture was filtered, washed with NaHCO$_3$, dried (MgSO$_4$) and concentrated in vacuo to give 4.56 g of solid which was purified by HPLC using 8% ethyl acetate/cyclohexane to elute the first fraction (1.52 g) followed by 15% ethyl acetate/cyclohexane to elute 1.46 g of the desired product. Recrystallization of the 1.46 g solid in hot hexane afforded 0.88 g (17.4%) of product as a white solid; mp 87°–88.5° C.

Anal. Calc'd. for C$_{14}$H$_{13}$F$_6$N$_1$O$_5$S$_1$: C, 39.91; H, 3.11; N, 3.32. Found: C, 39.86; H, 3.04; N, 3.29.

EXAMPLE 35

3-Ethyl 5-methyl 4-(ethylsulfonyl)-2,6-bis(trifluoromethyl)-3,5-pyridinedicarboxylate This material was prepared as described in Example 34: 4.5 g (0.011 mol) of product of Example 33, 7.66 g (0.024 mol) of MCPBA in 30 ml of CH$_2$Cl$_3$ were heated to reflux for 8 hours to afford 2.66 g of yellow oil. This oil, along with 1.52 g of solid, eluted with 8% ethyl acetate/cyclohexane in the purification of the compound of Example 34 above, were combined and chromatographed giving 3.39 g of solid. Recrystallization in hot hexane-ether afforded 2.14 g (44.5%) of product as a white solid; mp 99°–100.5° C.

Anal. Calc'd. for C$_{14}$H$_{13}$F$_6$N$_1$O$_6$S$_1$: C, 38.45; H, 3.00; N, 3.20. Found: C, 38.34; H, 2.94; N, 3.15.

EXAMPLE 36

3-Ethyl 5-hydrogen 4-ethylthio-2,6-bis(trifluoromethyl)-3,5-pyridinedicarboxylate This thio compound was prepared as described for the corresponding 4-oxy compound of Example 14 above by carboxylation: 14 ml of dry THF, 3.0 ml (0.022 mol) of diisopropylamine, 13.6 ml (0.021 mol) of 1.53M n-BuLi in hexane, 6.0 g (0.017 mol) of monocarboxylate product of Example 11, small pieces of dry ice were reacted affording a solid which was recrystallized in hot hexane to give 0.92 g (13.8%) of product as a beige solid; mp 108°–109.5° C.

Anal. Calc'd. for C$_{13}$H$_{11}$F$_6$N$_1$O$_4$S$_1$: C, 39.90; H, 2.83; N, 3.58. Found: C, 39.98; H, 2.85 N, 3.58.

PREPARATION OF PYRIDINEDICARBOXYLATE COMPOUNDS SUBSTITUTED WITH A NITROGEN ATOM AT THE 4-POSITION

Nitrogen-substituted compounds according to this invention may be prepared from the corresponding 4-halo-substituted pyridinedicarboxylate compound derived from Route 1 such as those of Examples 26–30 above. Representative of such compounds substituted in the 4-position with a nitrogen atom are those made in the following Examples 37–91.

EXAMPLE 37

3-Ethyl 5-methyl 6-(chlorodifluoromethyl)-4-(1-pyrrolidylamino)-2-(trifluoromethyl)-3,5-pyridinedicarboxylate A mixture of 5.0 g (0.013 mol) of product of Example 23, 3.42 g (0.034 mol) of triethylamine, 2.08 g (0.017 mol) of N-aminopyrrolidine hydrochloride in 30 ml of DMF were reacted at 45° C. for 1 hour. The reaction mixture was poured into water, extracted with ether, washed with diluted HCL, dried (MgSO$_4$) and concentrated in vacuo to 4.06 g of light yellow solid. This solid was recrystallized in hot hexane affording 3.47 g (59.9%) of product as a beige solid; mp 101°–103° C.

Anal. Calc'd. for C$_{16}$H$_{17}$Cl$_1$F$_5$N$_3$O$_4$: C, 43.11; H, 3.84; N, 9.43. Found: C, 42.80; H, 3.61; N, 9.37.

EXAMPLE 38

3-Ethyl 5-methyl 6-(chlorodifluoromethyl)-4-(allylamino)-2-(trifluoromethyl)-3,5-pyridinedicarboxylate This amino compound was prepared as described in Example 37: A 5.0 g (0.013 mol) portion of product of Example 28, 1.32 g (0.013 mol) of triethylamine, 0.98 ml (0.013 mol) of allylamine in 30 ml of DMF were reacted at room temperature affording 4.69 g of yellow semi-solid oil which was kugelrohr distilled at 47 Pa, pot temperature 107° C., affording 4.45 g (82.1%) of product as a light yellow oil, n$_D^{25}$ 1.4865.

Anal. Calc'd. for C$_{15}$H$_{14}$Cl$_1$F$_5$N$_2$O$_4$: C, 43.23; H, 3.39; N, 6.72. Found: C, 43.34; H, 3.40; N, 6.71.

EXAMPLE 39

3-Ethyl 5-methyl 6-(chlorodifluoromethyl)-4-(furfurylamino)-2-(trifluoromethyl)-3,5-pyridinedicarboxylate This amino compound was prepared as described in Example 37: A 5.0 g (0.013 mol) portion of product of Example 28, 1.32 g (0.013 mol) of triethylamine, 1.20 ml (0.013 mol) of furfurylamine in 30 ml of DMF were reacted affording 5.54 g of solid which was kugelrohr distilled at 40 Pa, pot temperature 129° C., to give 4.94 g of solid. This solid was chromatographed by HPLC using 5% ethyl acetate/cyclohexane as eluting solvent affording 4.54 g (76.5%) of a white solid. A portion of this solid, 2.2 g, was kugelrohr distilled at 29 Pa, pot temperature 134° C., to give 1.99 g of white solid which was recrystallized in cold hexane affording 1.44 g of product as a white solid; mp 47°–48° C.

Anal. Calc'd. for $C_{17}H_{14}Cl_1F_5N_2O_5$: C, 44.70; H, 3.09; N, 6.13. Found: C, 44.61; H, 3.11; N, 6.10.

EXAMPLE 40

3-Ethyl 5-methyl 6-(difluoromethyl)-4-(tetrahydrofurfurylamino)-2-(trifluoromethyl)-3,5-pyridinedicarboxylate This amino compound was prepared as described in Example 22: 2.36 g (0.005 mol) of product of Example 39, 51 g (0.005 mol) of triethyl-amine and 0.12 g of Pd/C (10%) in 30 ml of ethanol were hydrogenated affording a yellow oil which was kugelrohr distilled at 28 Pa, pot temperature 133° C., affording 1.67 g (78.3%) of product as a yellow oil, $n_D^{25}$ 1.4884. Anal. Calc'd. for $C_{17}H_{19}F_5N_2O_5$: C, 47.89; H, 4.49; N, 6.57. Found: C, 47.69; H, 4.53; N, 6.48.

EXAMPLE 41

3-Ethyl 5-methyl 6-(chlorodifluoromethyl)-4-cyclopropylmethylamino-2-(trifluoromethyl)-3,5-pyridinedicarboxylate This amino compound was prepared as described in Example 37: 5.0 g (0.013 mol) of product of Example 28, 2.63 g (0.026 mmol) of triethylamine, 1.4 g (0.013 mol) of aminomethylcyclopropane hydrochloride in 30 ml of DMF were reacted at room temperature affording 4.86 g of orange oil which was chromatographed by HPLC using 10% ethyl acetate/cyclohexane as eluting solvent to give 3.87 g (69.1%) of product as a yellow oil, $n_D^{25}$ 1.4837.

Anal. Calc'd. for $C_{16}H_{16}Cl_1F_5N_2O_4$: C, 44.61; H, 3.74; N, 6.50. Found: C, 44.60; H, 3.73; N, 6.47.

EXAMPLE 42

3-Ethyl 5-methyl 6-(chlorodifluoromethyl)-4-(1-imidazolyl)-2-(trifluoromethyl)-3,5-pyridinedicarboxylate This amino compound was prepared as described in Example 37: 5.0 g (0.013 mol) of product of Example 28, 2.63 g (0.026 mol) of triethylamine, 0.89 g (0.013 mol) of imidazole in 30 ml of DMF were reacted at room temperature for 16 hours affording an oil which was chromatographed by HPLC using 10% acetic acid/cyclohexane as eluting solvent to give 3.41 g of yellow oil. This oil was kugelrohr distilled at 40 Pa, pot temperature 80° C., in order to remove the excess traces of acetic acid. The pot residue was dissolved in ether, concentrated in vacuo and the solid which remained was recrystallized in hot hexane to afford 1.24 g (22.3%) of product as a tan solid; mp 81°–82° C.

Anal. Calc'd. for $C_{15}H_{11}Cl_1F_5N_3O_4$: C, 42.12; H, 2.59; N, 9.82. Found: C, 42.23; H, 2.61; N, 9.80.

EXAMPLE 43

3-Ethyl 5-methyl 6-(difluoromethyl)-4-(n-propylamino)-2-(trifluoromethyl)-3,5-pyridinedicarboxylate This amino compound was prepared as described in Example 22: 2.2 g (0.005 mol) of product of Example 38, 0.53 g (0.005 mol) of triethylamine and 0.12 g of Pd/C (10%) in 30 ml of ethanol were hydrogenated affording 1.76 g of solid which was recrystallized in hot hexane to give 1.45 g (75.5%) of produce as a white solid; mp 84°–86° C.

Anal. Calc'd. for $C_{15}H_{17}F_5N_2O_4$: C, 46.88; H, 4.46; N, 7.29. Found: C, 47.04; H, 4.44; N, 7.26.

EXAMPLE 44

3-Ethyl 5-methyl 6-(difluoromethyl)-4-(cyclopropylmethylamino)-2-(trifluoromethyl)-3,5-pyridinedicarboxylate This amino compound was prepared as described in Example 22: 2.15 g (0.005 mol) of product of Example 41, 0.51 g (0.005 mol) of triethylamine and 0.12 g of Pd/C (10%) in 30 ml of ethanol were hydrogenated affording 1.45 g of solid which was recrystallized in hot ethyl acetate/hexane affording 1.32 g (66.6%) of product as a white solid; mp 101°–103° C.

Anal. Calc'd. for $C_{16}H_{17}F_5N_2O_4$: C, 48.49; H, 4.32; N, 7.07. Found: C, 48.54; H, 4.35; N, 7.02.

EXAMPLE 45

3-Ethyl 5-methyl 4-aziridinyl-6-(chlorodifluoromethyl)-2-(trifluoromethyl)-3,5-pyridinedicarboxylate This amino compound was prepared as described in Example 37: 5.0 g (0.013 mol) of product of Example 28 and 1.12 g (0.026 mol) of aziridine in 30 ml of DMF were reacted at room temperature for 16 hours affording 4.82 g of an orange oil containing a 65:35 mixture of reaction products. The crude mixture was purified by HPLC using 10% ethyl acetate/cyclohexane as eluting solvent to give two fractions. The first fraction gave 2.08 g (40%) of the above product, after kugelrohr distillation at 128°–130° C./53 Pa, as a white solid; mp 67°–69° C.

Anal. Calc'd. for $C_{14}H_{12}Cl_1F_5N_2O_4$: C, 41.76; H, 3.00; N, 6.96. Found: C, 41.61; H, 3.02; N, 6.88.

EXAMPLE 46

3-Ethyl 5-methyl 4-(2-chloroethylamino)-6-(chlorodifluoromethyl)-2-(trifluoromethyl)-3,5-pyridinedicarboxylate The second fraction from the HPLC purification of Example 45 afforded 1.13 g (20%) of this product, after kugelrohr distillation at 134° C./47 Pa, as a clear oil, $m_D^{25}$ 1.4903.

Anal. Calc'd. for $C_{14}H_{13}Cl_2F_5N_2O_4$: C, 38.29; H, 2.98; N, 6.38. Found: C, 38.38; H, 3.02; N, 6.33.

EXAMPLE 47

3-Ethyl 5-methyl 6-(chlorodifluoromethyl)-4-cyclobutylamino-2-(trifluoromethyl)-3,5pyridinedicarboxylate This amino compound was prepared as described in Example 37: 5.0 g (0.013 mol) of product of Example 28, 1.32 g (0.013 mol) of triethylamine and 0.92 g (0.013 mol) of cyclobutylamine in 30 ml of DMF were reacted at room temperature for ½ hour affording an orange oil. The crude product was purified by HPLC using 2% ethyl acetate/cyclohexene as eluting solvent followed by kugelrohr distillation at 128° C./60 Pa to give 3.64 g (65%) of product as a white solid; mp 51°–53° C.

Anal. Calc'd. for $C_{16}H_{16}Cl_1F_5N_2O_4$: C, 44.61; H, 3.74; N, 6.50. Found: C, 44.55; H, 3.76; N, 6.48.

EXAMPLE 48

3-Ethyl 5-methyl 4-azido-2,6-bis(trifluorometyl)-3,5-pyridinedicarboxylate

A mixture of 15.13 g (0.040 mol) of product of Example 27, 2.85 g (0.040 mol) of sodium azide and 175 ml of DMF was stirred for 1 hour and poured into 500 ml of water. The mixture was extracted with ether. The ether was extract was washed several times with water, dried (MgSO$_4$) and concentrated to give 14.4 g (93.7%) of product; mp 46°–47° C.

Anal. Calc'd. for $C_{12}H_8F_6N_4O_4$: C, 37.32; H, 2.09; N, 14.51. Found: C, 37.51; H, 2.06; N, 14.35.

EXAMPLE 49

3-Ethyl 5-methyl 4-(isopropylamino)-2,6-bis(trifluoromethyl)-3,5-pyridinedicarboxylate This compound was prepared as described in Example 37: 7.0 g (0.018 mol) of product of Example 27, 3.2 ml (0.037 mol) of isopropylamine in 30 ml of DMF were reacted at room temperature for ½ hour affording a brown oil which was kugelrohr distilled at 78 Pa, pot temperature 95° C., to give 6.07 g (83.8%) of product as a yellow oil, $n_D^{25}$ 1.4560.

Anal. Calc'd. for $C_{15}H_{16}F_6N_2O_4$: C, 44.78; H, 4.01; N, 6.96. Found: C, 44.68; H, 4.05; N, 6.94.

EXAMPLE 50

3-Ethyl 5-methyl 4-(dipropylamino)-2,6-bis(trifluoromethyl)-3,5-pyridinedicarboxylate This compound was prepared as described in Example 37: 7.0 g (0.018 mol) of product of Example 27, 5.1 ml (0.037 mol) of dipropylamine in 30 ml of DMF were reacted at room temperature affording 7.7 g (96.3%) of solid which was recrystallized in hot hexane to give 2.19 g of product as a tan solid; mp 65°–66° C.

Anal. Calc'd. for $C_{18}H_{22}F_6N_2O_4$: C, 48.65; H, 4.99; N, 6.30. Found: C, 48.67; H, 4.98; N, 6.28.

EXAMPLE 51

3-Ethyl 5-methyl 4-(1-pyrrolidinyl)-2,6-bis(trifluoromethyl)-3,5-pyridinedicarboxylate This compound was prepared as described in Example 37: 6.0 g (0.016 mol) of product of Example 27, 2.6 ml (0.032 mol) of pyrrolidine in 30 ml of DMF were reacted affording a brown solid which was recrystallized in hot hexane giving 5.18 g (78.1%) of product as a tan solid; mp 68.5°–70° C.

Anal. Calc'd. for $C_{16}H_{16}F_6N_2O_4$: C, 46.38; H, 3.89; N, 6.76. Found: C, 46.27; H, 3.93; N, 6.77.

EXAMPLE 52

3-Ethyl 5-methyl 4-(cyclopropylamino)-2,6-bis(trifluoromethyl)-3,5-pyridindicarboxylate This compound was prepared as described in Example 37: 5.0 g (0.013 mol) of product of Example 27, 1.83 ml (0.026 mol) of cyclopropylamine in 30 ml of DMF were reacted at room temperature affording 4.95 g of dark oil which was purified by HPLC using 5% ethyl acetate/cyclohexane as eluting solvent to give 3.87 g (74.4%) of product as a yellow oil, $n_D^{25}$ 1.4708.

Anal. Calc'd. for $C_{15}H_{14}F_6N_2O_4$: C, 45.01; H, 3.53; N, 7.00. Found: 45.12; H, 3.48; N, 6.86.

EXAMPLE 53

3-Ethyl 5-methyl 6-(chlorodifluoromethyl)-4-(diethylamino)-2-(trifluoromethyl)-3,5-pyridinedicarboxylate This compound was prepared as described in Example 37: 5.0 g (0.013 mol) of product of Example 28, 2.6 ml (0.025 mol) of diethylamine in 25 ml of DMF were reacted at room temperature for 16 hours affording a yellow semi-solid oil which was kugelrohr distilled at 80 Pa, pot temperature 102°–105° C., to give 4.63 g (82.3%) of product as a yellow solid; mp 31.5°–33° C.

Anal. Calc'd. for $C_{16}H_{18}Cl_1F_5N_2O_4$: C, 44.41; H, 4.19; N, 6.47. Found: C, 44.36; H, 4.16; N, 6.43.

EXAMPLE 54

3-Ethyl 5-methyl 4-(diethylamino)-6-(difluoromethyl)-2-(trifluoromethyl)-3,5-pyridinedicarboxylate A mixture of 2.5 g (0.006 mol) of product of Example 53, 0.61 g (0.006 mol) of triethylamine and 0.12 g of Pd/C (10%) in 35 ml of ethanol was hydrogenated at 50° C. under 480 kPa of hydrogen pressure for 45 minutes. Reaction mixture was filtered through Celite and concentrated in vacuo. The residue was dissolved in ether, washed with 10% HCl and the aqueous 10% HCl layer was extracted with chloroform. The combined organic layers were dried (MgSO$_4$) and concentrated in vacuo to 1.91 g. Crude was kugelrohr distilled at 109 Pa, pot temperature 99° C., affording 1.63 g (68.2%) of this product as a yellow oil, $n_D^{25}$ 1.4682.

Anal. Calc'd. for $C_{16}H_{19}F_5N_2O_4$: C, 48.25; H, 4.81; N, 7.03. Found C, 48.19; H, 4.61; N, 6.96.

EXAMPLE 55

3-Ethyl 5-methyl 6-(chlorodifluoromethyl)-4-(cyclopropylamino)-2-(trifluoromethyl)-3,5-pyridinedicarboxylate This compound was prepared as described in Example 37: 6.0 g (0.015 mol) of product of Example 28, 2.1 ml (0.030 mol) of cyclopropylamine in 25 ml of DMF were reacted at room temperature affording 7.24 g of oil. Purification by HPLC using 5% ethyl acetate/cyclohexane as eluting solvent afforded 4.77 g of solid which was recrystallized in hot hexane to give 3.92 g (62.7%) of product as a beige solid; mp 72°–73.5° C.

Anal. Calc'd. for $C_{15}H_{14}Cl_1F_5N_2O_4$: C, 43.23; H, 3.39; N, 6.72. Found: C, 43.20; H, 3.37; N, 6.74.

EXAMPLE 56

3-Ethyl 5-methyl 4-(cyclopropylamino)-6-(difluoromethyl)-2-(trifluoromethyl)-3,5-pyridinedicarboxylate This compound was prepared as described in Example 22: 2.0 g (0.005 mol) of product of Example 55, 0.49 g (0.005 mol) of triethylamine and 0.12 g of Pd/C (10%) in 30 ml of ethanol were reacted affording a residue which was Kugelrohr distilled at 126 Pa, pot temperature 130° C., and 1.18 g (61.7%) of product was collected as a beige solid; mp 68°–69.5° C.

Anal. Calc'd. for $C_{15}H_{15}F_5N_2O_4$: C, 47.13; H, 3.96; N, 7.33. Found: C, 46.99; H, 3.96; N, 7.27.

EXAMPLE 57

3-Ethyl 5-methyl 6-(chlorodifluoromethyl)-4-(2,2-dimethylhydrazino)-2-(trifluoromethyl)-3,5-pyridinedicarboxylate This compound was prepared as described in Example 37: 5.0 g (0.013 mol) of product of Example 28, 1.9 ml (0.025 mol) of unsym-dimethylhydrazine in 30 ml of DMF were reacted affording a residue which was recrystallized in hot hexane to give 4.57 g (83.8%) of product as a yellow solid; mp 97°–98° C.

Anal. Calc'd. for $C_{14}H_{15}Cl_1F_5N_3O_4$: C, 40.06; H, 3.60; N, 10.01. Found: C 40.07; H, 3.65; N, 9.97.

EXAMPLE 58

3-Ethyl 5-methyl 6-(chlorodifluoromethyl)-4-(t-butylamino)-2-(trifluoromethyl)-3,5-pyridinedicarboxylate This compound was prepared as described in Example 37: 5.0 g (0.013 mol) of product of Example 28, 3.9 ml (0.036 mol) of t-butylamine in 30 ml of DMF were reacted affording a residue which was kugelrohr distilled at 133 Pa, pot temperature 126° C., giving 4.49 g. Purification by HPLC using 5% ethyl acetate/cyclohexane as eluting solvent afforded 1.12 g (19.9%) of product as a white solid; mp 51.5°–53° C.

Anal. Calc'd. for $C_{16}H_{18}Cl_1F_5N_2O_4$: C, 44.41; H, 4.19; N, 6.47. Found: C, 44.24; H, 4.18; N, 6.44.

EXAMPLE 59

3-Ethyl 5-methyl 6-(difluoromethyl)-4-(2,2-dimethylhydrazino)-2-(trifluoromethyl)-3,5-pyridinedicarboxylate This compound was prepared as described in Example 22: 2.2 g (0.005 mol) of product of Example 57, 0.53 g (0.005 mol) of triethylamine and 0.12 g of Pd/C (10%) in 30 ml of ethanol were hydrogenated affording a residue which was recrystallized in hot hexane to give 1.28 g (66.4%) of product as a yellow solid; mp 98.5°–100° C.

Anal. Calc'd. for $C_{14}H_{16}F_5N_3O_4$: C, 43.64; H, 4.19; N, 10.91. Found: C, 43.51; H, 4.20; N, 10.90.

EXAMPLE 60

3-Ethyl 5-methyl 6-(chlorodifluoromethyl)-4-(isopropylamino)-2-(trifluoromethyl)-3,5-pyridinedicarboxylate This compound was prepared as described in Example 37: 5.0 g (0.013 mol) of product of Example 28, 2.2 ml (0.026 mol) of isopropylamine in 30 ml of DMF were reacted at room temperature affording a residue which was kugelrohr distilled at 80 Pa, pot temperature 112° C., to give 4.86 g (89.3%) of product as a yellow solid; mp 43.5°–45° C.

Anal. Calc'd. for $C_{15}H_{16}Cl_1F_5N_2O_4$: C, 43.02, H, 3.85; N, 6.69. Found: C, 42.99; H, 3.87; N, 6.64.

EXAMPLE 61

3-Ethyl 5-methyl 4-amino-6-(chlorodifluoromethyl)-2-(trifluoromethyl)-3,5-pyridinedicarboxylate This compound was prepared as described in Example 37: 5.0 g (0.013 mol) of product of Example 28 in 30 ml of DMF was stirred at room temperature while $NH_3$ was bubbled in. Reaction was monitored by GC. The residue was kugelrohr distilled at 80 Pa, pot temperature 106° C., giving 4.17 g (85.2%) of product as a yellow solid; mp 69°–70° C.

Anal. Calc'd. for $C_{12}H_{10}Cl_1F_5N_2O_4$: C, 38.26; H, 2.68; N, 7.44. Found: C, 38.29; H, 2.68; N, 7.43.

EXAMPLE 62

3-Ethyl 5-methyl 6-(chlorodifluoromethyl)-4-(N-ethyl-N-methylamino)-2-(trifluoromethyl)-3,5-pyridinedicarboxylate This compound was prepared as described in Example 37: 5.0 g (0.013 mol) of product of Example 28, 1.54 g (0.026 mol) of N-ethylmethylamine in 30 ml of DMF were reacted at room temperature for 16 hours affording a residue which was kugelrohr distilled at 80 Pa, pot temperature 104° C., to give 4.7 g of oil. Purification by HPLC using 5% ethyl acetate/cyclohexane as eluting solvent afforded 4.0 g of oil which was purified by kugelrohr distillation at 67 Pa, pot temperature 107° C., to give 3.85 g (70.7%) of product as a yellow solid; mp 33°–35° C.

Anal. Calc'd. for $C_{15}H_{16}Cl_1F_5N_2O_4$: C, 43.02; H, 3.85; N, 6.69. Found: C, 43.07; H, 3.87; N, 6.66.

EXAMPLE 63

3-Ethyl 5-methyl 6-(difluoromethyl)-4-isopropylamino-2-(trifluoromethyl)-3,5-pyridinedicarboxylate This compound was prepared as described in Example 54: 2.7 g (0.006 mol) of product of Example 60, 0.65 g (0.006 mol) of triethylamine and 0.12 g of Pd/C (10%) in 30 ml of ethanol were reacted affording an oil residue which was kugelrohr distilled at 80 Pa, pot temperature 104° C., to give 2.07 g (89.8%) of product as a white solid; mp 53°–55° C.

Anal. Calc'd. for $C_{15}H_{17}F_5N_2O_4$: C, 46.88; H, 4.46; N, 7.29. Found: C, 46.90; H, 4.48; N, 7.26.

EXAMPLE 64

3-Ethyl 5-methyl 4-amino-6-(difluoromethyl)-2-(trifluoromethyl)-3,5-pyridinedicarboxylate This compound was prepared as described in Example 54: 2.0 g (0.005 mol) of product of Example 61, 0.54 g (0.005 mol) of triethylamine and 0.12 g of Pd/C (10%) in 35 ml of ethanol were hydrogenated affording a residue which was recrystallized in hot hexane-ether to give 1.19 g (69.5%) of product as a white solid; mp 60°–69° C.

Anal. Calc'd. for $C_{12}H_{11}F_5N_2O_4$: C, 42.12; H, 3.24; N, 8.19. Found: C, 42.25; H, 3.26; N, 8.16.

This compound was prepared also by alkylation of the product of Example 101.

EXAMPLE 65

3-Ethyl 5-methyl 6-(chlorodifluoromethyl)-4-(N-cyclopropylmethylamino)-2-(trifluoromethyl)-3,5-pyridinedicarboxylate This compound was prepared as described in Example 37: 5.0 g (0.013 mol) of product of Example 28, 1.85 g (0.026 mol) of N-methylcyclopropylamine (60% pure) in 30 ml of DMF were reacted at room temperature affording 4.3 g of yellow semi-solid oil. Purification by HPLC using 5% ethyl acetate/cyclohexane as eluting solvent afforded an oil which was kugelrohr distilled at 93 Pa, pot temperature 103° C. to give 1.36 g (24.3%) of product as a yellow solid; mp 56°–58° C.

Anal. Calc'd. for $C_{16}H_{16}Cl_1F_5N_2O_4$: C, 44.61; H, 3.74; N, 6.50. Found: C, 44.52; H, 3.78; N, 6.49.

EXAMPLE 66

3-Etnhyl 5-methyl 6-(difluoromethyl)-4-(N-ethyl-N-methylamino)-2-(trifluoromethyl)-3,5-pyridinedicarboxylate This compound was prepared as described in Example 54: 2.0 g (0.005 mol) of product of Example 62, 0.48 g (0.005 mol) of triethylamine and 0.12 g of Pd/C (10%) in 30 ml of ethanol were reacted affording a yellow oil which was kugelrohr distilled at 67 Pa, pot temperature 107° C., to give 0.97 g (50.5%) of product as a yellow oil, $n_D^{25}$ 1.4706.

Anal. Calc'd. for $C_{15}H_{17}F_5N_2O_4$: C, 46.88; H, 4.46; N, 7.29. Found: C, 46.76; H, 4.50; N, 7.26.

EXAMPLE 67

3-Ethyl 5-methyl 6-(chlorodifluoromethyl)-4-[(2-ethoxy-2-oxoethyl)amino]-2-(trifluoromethyl)-3,5-pyridinedicarboxylate This compound was prepared as described in Example 37: 5.0 g (0.013 mol) of product of Example 28, 1.82 g (0.013 mol) of ethyl glycinate hydrochloride, 2.63 g (0.026 mol) of triethylamine in 30 ml of DMF were reacted at room temperature for 16 hours affording a residue which was kugelrohr distilled at 67 Pa, pot temperature 150° C., to give 4.96 g of solid. Recrystallization in hot hexane afforded 4.60 g (75.3%) of product as a beige solid; mp 60°–61.5° C.

Anal. Calc'd. for $C_{16}H_{16}Cl_1F_5N_2O_6$: C, 41.53; H, 3.48; N, 6.05. Found: C, 40.88; H, 3.47; N, 5.93.

EXAMPLE 68

3-Ethyl 5-methyl 6-(chlorodifluoromethyl)-4-(phenylamino)-2-(trifluoromethyl)-3,5-pyridine-dicarboxylate This compound was prepared as described in Example 37: 5.0 g (0.013 mol) of product of Example 28, 3.6 ml (0.039 mol) of aniline, 1.3 g (0.013 mol) of triethylamine in 30 ml of DMF were reacted at room temperature for 16 hours and heated to 35° C. for 20 minutes. The residue was recrystallized in hot hexane affording 4.0 g (68.0%) of product as a beige solid; mp 91°–92° C.

Anal. Calc'd. for $C_{18}H_{14}Cl_1F_5N_2O_4$: C, 47.75; H, 3.12; N, 6.19. Found: C, 47,62; H, 3.09; N, 6.16.

EXAMPLE 69

3-Ethyl 5-methyl 4-(1-azetidinyl)-6-(chloro-difluoromethyl)-2-(trifluoromethyl)-3,5-pyridinedicarboxylate This compound was prepared as described in Example 37: 5.0 g (0.013 mol) of product of Example 28, 1.32 g (0.013 mol) of triethylamine, 0.75 g (0.013 mol) of azetidine in 30 ml of DMF were reacted at room temperature for 16 hours affording 4.71 g of solid which was recrystallized in hot hexane to give 3.93 g (72.5%) of white solid. A portion of this solid, 1.93 g, was recrystallized a second time in hot hexane to give 1.43 g of product as a white solid; mp 74.5°–75.5° C.

Anal. Calc'd. for $C_{15}H_{14}Cl_1F_5N_2O_4$: C, 43.23; H, 3.39; N, 6.72. Found: C, 43.16; H. 3.39; N, 6.72.

Example 70

3-Ethyl 5-methyl 4-(1-azetidinyl)-6-(difluoromethyl)-2-(trifluoromethyl)-3,5-pyridinedicarboxylate This compound was prepared as described in Example 54: 2.0 g (0.0024 mol) of product of Example 69, 0.24 g (0.0024 mol) of triethylamine and 0.12 g of Pd/C (10%) in 30 ml of ethanol were hydrogenated affording a dark oil which was kugelrohr distilled at 80 Pa, pot temperature 146° C., to give 1.1 g of a of a clear oil which crystallized. Recrystallization in hot hexane-ether afforded 0.60 g (65.4%) of product as a white solid; mp 78.5°–80.5° C.

Anal. Calc'd. for $C_{15}H_{15}F_5N_2O_4$: C, 47.13; H, 3.96; N, 7.33. Found: C, 47.11; H, 3.99; N, 7.05.

EXAMPLE 71

3-Ethyl 5-methyl 6-(chlorodifluoromethyl)-4-(1-pyrrolidinyl)-2-(trifluoromethyl)-3,5-pyridine-dicarboxylate This compound was prepared as described in Example 37: 5.0 g (0.013 mol) of product of Example 28, 2.1 ml (0.026 mol) of pyrrolidine in 30 ml of DMF were reacted at room temperature for 16 hours affording 4.69 g of solid. Recrystallization in hot hexane-ether gave 4.36 g (77.9%) of product as a white solid; mp 72°–73.5° C.

Anal. Calc'd. for $C_{16}H_{16}Cl_1F_5N_2O_4$: C, 44.61; H, 3.74; N, 6.50. Found: C, 44.51; H, 3.77; N, 6.48.

EXAMPLE 72

3-Ethyl 5-methyl 6-(difluoromethyl)-4-(1-pyrrolidinyl)-2-(trifluoromethyl)-3,5-pyridine-dicarboxylate This compound was prepared as described in Example 54: 2.36 g (0.006 mol) of product of Example 71, 0.61 g (0.006 mol) of triethylamine, 0.22 g (0.006 mol) of magnesium oxide and 0.12 g of Pd/C (10%) in 30 ml of ethanol were hydrogenated affording 1.69 g of solid which was recrystallized in hot hexane to give 1.34 g (56.4%) of product as a white solid; mp 102°–103° C.

Anal. Calc'd. for $C_{16}H_{17}F_5N_2O_4$: C, 48.49; H, 4.32; N, 7.07. Found: C, 48.44; H, 4.35; N, 7.03.

EXAMPLE 73

3-Ethyl 5-methyl
6-(chlorodifluoromethyl)-4-[(2,2,2-trifluoroethyl)amino]-2-(trifluoromethyl)-3,5-pyridinedicarboxylate This compound was prepared as described in Example 37: 5.0 g (0.013 mol) of product of Example 28, 1.81 ml (0.013 mol) of triethylamine, 1.1 ml (0.013 mol) of 2,2,2-trifluoroethylamine in 30 ml of DMF were reacted at 40° C. for 48 hours affording 4.71 g of oil. This oil was kugelrohr distilled at 53 Pa, pot temperature 110°–120° C. to give 2.82 g (47.3%) of product as a yellow oil, $n_D^{25}$ 1.4496.

Anal. Calc'd. for $C_{14}H_{11}Cl_1F_8N_2O_4$: C, 36.66; H, 2.42; N, 6.11. Found: C, 36.80; H, 2.25; N, 6.08.

EXAMPLE 74

3-Ethyl 5-methyl
6-(difluoromethyl)-4-[(2,2,2-trifluoroethyl)amino]-2-(trifluoromethyl)-3,5- pyridinedicarboxylate This compound was prepared as described in Example 54: 1.73 g (0.004 mol) of product of Example 73, 0.40 g (0.004 mol) of triethylamine, 0.08 g (0.002mol) of magnesium oxide and 0.12 g of Pd/C (10%) in 35 ml of ethanol were reacted affording 1.20 g of yellow solid which was recrystallized in hot hexane affording 0.97 g. This solid was kugelrohr distilled at 53 Pa, pot temperature 105° C. and 0.86 g of solid was collected. This solid was purified on the chromatotron using 10% ethyl acetate/cyclohexane as eluting solvent and 0.75 g (44.2%) of product was collected as a light yellow solid; mp 64°–66° C.

Anal. Calc'd. for $C_{14}H_{12}F_8N_2O_4$: C, 39.64; H, 2.85; N, 6.60. Found: C, 39.64; H, 2.78; N, 6.55.

EXAMPLE 75

3-Ethyl 5-methyl
6-(chlorodifluoromethyl)-4-[(2,2,3,3,3-pentafluoropropyl)amino]-2-(trifluoromethyl)-3,5-pyridinedicarboxylate This compound was prepared as described in Example 37: 5.0 g (0.013 mol) of product of Example 28, 1.94 g (0.013 mol) of 2,2,3,3,3-pentafluoropropylamine, 1.81 ml (0.013 mol) of triethylamine in 30 ml of DMF were reacted at 50° C. for 64 hours, affording 5.36 g of oil. This oil was purified by HPLC using 1% ethyl acetate/cyclohexane as eluting solvent to give 1.82 g of oil which was kugelrohr distilled at 41 Pa, pot temperature 95° C., to give 1.55 g (23.4%) of product as a clear oil, $n_D^{25}$ 1.4351.

Anal. Calc'd. for $C_{15}H_{11}Cl_1F_{10}N_2O_4$: C, 35.42; H, 2.18; N, 5.51. Found: C, 35.23; H, 1.94; N, 5.44.

EXAMPLE 76

Dimethyl
6-(difluoromethyl)-4-(iso-propylamino)-2-(trifluoromethyl)-3,5-pyridine-dicarboxylate A mixture of 7.61 g (0.020 mol) of product of Example 63, 6.7 g (0.118 mol) of KOH and 30 ml of $H_2O$ in 200 ml of ethanol was refluxed for 16 hours. The reaction mixture was poured into 250 ml containing 50 ml of concentrated HCl, extracted with ether, dried (MgSO$_4$) and concentrated in vacuo to a dark oil. This oil, 5.53 g (0.040 mol) of $K_2CO_3$ and 3.75 ml (0.060 mol) of methyl iodide in 50 ml of DMF was stirred at room temperature for 19 hours. The reaction mixture was poured into water, extracted with ether, dried (MgSO$_4$) and concentrated in vacuo to 8.18 g of dark oil. This oil was chromatographed on the HPLC using 5% ethyl acetate/cyclohexane as eluting solvent affording 5.51 g (74.4%) of orange oil. A portion of this oil, 1.41 g, was kugelrohr distilled at 40 Pa, pot temperature 104° C., and 1.37 g of product was collected as a light yellow oil, $n_D^{25}$ 1.4765.

Anal. Calc'd. for $C_{14}H_{15}F_5N_2O_4$: C, 45.41; H, 4.08; N, 7.56. Found: C, 45.20; H, 4.07; N, 7.55.

EXAMPLE 77

5-Ethyl 3-methyl
6-(difluoromethyl)-4-(isopropylamino)-2-(trifluoromethyl)-3,5-pyridinedicarboxylate A mixture of 4.1 g (0.011 mol) of product of Example 76, 0.62 g (0.011 mol) of KOH and 5 ml of $H_2O$ in 50 ml of methanol was stirred at room temperature overnight. The reaction mixture was poured into 250 ml of $H_2O$ containing 50 ml of concentrated HCl, extracted with ether, dried (MgSO$_4$) and concentrated in vacuo to 3.76 g of yellow oil. This oil, 1.52 g (0.011 mol) of $K_2CO_3$ and 0.88 ml (0.011 mol) of ethyl iodide in 30 ml of DMF was stirred at room temperature overnight. The reaction mixture was poured into water, extracted with ether, dried (MgSO$_4$) and concentrated in vacuo to 3.64 g of yellow oil. Kugelrohr distillation at 53 Pa, pot temperature 103° C., afforded 2.98 g (70.5%) of product as a light yellow oil which solidified; mp 37°–39° C.

Anal. Calc'd for $C_{15}H_{17}F_5N_2O_4$: C, 46.88; H, 4.46; N, 7.29. Found: C, 46.78; H, 4.42; N, 7.22.

EXAMPLE 78

Diethyl
2-(chlorodifluoromethyl)-4-cyclopropylamino-6-(trifluoromethyl)-3,5-pyridinedicarboxylate This compound was prepared as described in Example 52: 3.0 g (0.0073 mol) of product of Example 30, 0.81 g (1.1 ml, 0.008 mol) of triethylamine and 0.46 g (0.6 ml, 0.008 mol) of cyclopropylamine in 10 ml of DMF were reacted affording after kugelrohr distillation 2.48 g (79%) of product as a light yellow oil, $n_D^{25}$ 1.4869.

Anal. Calc'd. for $C_{16}H_{16}Cl_1F_5N_2O_4$: C, 44.61; H, 3.74; N, 6.50. Found: C, 44.89; H, 3.88; N, 6.25.

EXAMPLE 79

Diethyl
4-cyclopropylamino-6-(difluoromethyl)-2-(trifluoromethyl)-3,5-pyridinedicarboxylate This compound was prepares as described for Example 54: 7.8 g (0.018 mol) of product of Example 78, 0.30 g of 5% Pd/C and 1.8 g (0.018 mol) of triethylamine in 35 ml of ethanol were hydrogenated affording 6.38 g (88%) of product after kugelrohr distillation at 155°–165° C./20 Pa as a light yellow solid; mp 63.5°–66° C.

Anal. Calc'd. for $C_{16}H_{17}F_5N_2O_4$: C, 48.49; H, 4.32; N, 7.07. Found: C, 48.33; H, 4.33; N, 7.02.

EXAMPLE 80

3-Ethyl 5-methyl
6-(difluoromethyl)-4-cyclobutylamino-2-(trifluoromethyl)-3,5-pyridinedicarboxylate This product was pepared as described for Example 54: 2.0 g (0.005 mol) of product of Example 47, 0.12 g of 10% Pd/C and 0.47 g (0.005 mol) of triethylamine in 30 ml of ethanol were hydrogenated affording 1.6 g of solid. Crude was recrystallized in hexane to give 1.31 g (66%) of product as a tan solid; mp 65°–67° C.

Anal. Calc'd. for $C_{16}H_{17}F_5N_2O_4$: C, 48.49; H, 4.32; N, 7.07. Found: C, 48.40; H, 4.36; N, 7.04.

EXAMPLE 81

3-Ethyl 5-methyl 6-(chlorodifluoromethyl)-4-(2-methylaziridinyl)-2-(trifluoromethyl)-3,5-pyridinedicarboxylate To 50 ml of DMF was added 5.0 g (0.0126 mol) of product of Example 28, followed by 1.27 g (0.01261 mol) of triethylamine and 1.74 g (0.0126 mol) of $K_2CO_3$. To this mixture was added 0.922 g (0.0161 mol) of propyleneimine. This reaction mixture was stirred under $N_2$ for 48 hours at room temperature. The reaction mixture was then poured into $H_2O$ and extracted with diethyl ether. The ether phase was then washed with $H_2O$, and dried over $MgSO_4$. The dry ether phase was then concentrated in vacuo to a crude yield of 4.8 g of a brown oil. This oil was kugelrohr distilled at 105° C./53 Pa, to yield 4.0 g of a yellow oil (76%), $n_D^{25}$ 1.4763.

Anal. Calc'd for $C_{15}H_{14}Cl_1F_5N_2O_4$: C, 43.23; H, 3.39; N, 6.72. Found: C, 43.21; H, 3.40; N, 6.71.

EXAMPLE 82

3-Ethyl 5-methyl 6-(difluoromethyl)-4-(aziridinyl)-2-(trifluoromethyl)-3,5-pyridinedicarboxylate A mixture of 3.5 g (0.00869 mol) of product of Example 45, 0.879 g (0.00869 mol) of triethylamine, and 0.35 g of 5% palladium on carbon (50% water coated) in 100 ml of ethanol was hydrogenated (446 kPa) at room temperature for 8 hours. The reaction mixture was then filtered through celite, and concentrated in vacuo to remove the ethanol. The residue was then stirred for 12 hours in a mixture of 1.20 g (0.0869 mol) of $K_2CO_3$ in 30 ml of DMF. This reaction mixture was then poured into $H_2O$ and extracted with diethyl ether. The ether phase was then washed with $H_2O$, dried over $MgSO_4$, and concentrated in vacuo to 1.8 g of a yellow crystalline material. This solid was recrystallized in ethyl acetate/hexane to give 0.5 g (15.6%) of a beige solid product; mp 92°–95° C.

Anal. Calc'd. for $C_{14}H_{13}F_5N_2O_4$: C, 45.66; H, 3.56; N, 7.61. Found: C, 45.58; H, 3.61; N, 7.50.

EXAMPLE 83

3-Ethyl 5-methyl 6-(difluoromethyl)-4-(2-methylaziridinyl)-2-(trifluoromethyl)-3,5-pyridinedicarboxylate A mixture of 2.5 g (0.0059 mol) of product of Example 81, 0.6 g (0.0059 mol) of triethylamine and 0.25 g of 5% Pd/C (50% water coated) in 100 ml of ethanol was hydrogenated (446 kPa for 18 hours at 50° C. The mixture was then filtered through celite and concentrated in vacuo to remove the ethyl alcohol. The residue was poured into water, and extracted with diethyl ether. The ether extract was washed with water, then dried over $MgSO_4$. The dry ether phase was then concentrated in vacuo to yield 2.00 g of a yellow solid. This solid was then recrystallized in hexane to yield 1.28 g (56%) of product as a tan solid; mp 61° C.

Anal. Calc'd. for $C_{15}H_{15}F_5N_2O_4$: C, 47.13; H, 3.96; N, 7.33. Found: C, 47.18; H, 3.98; N, 7.30.

EXAMPLE 84

3-Ethyl 5-hydrogen 4-cyclopropylamino-6-(difluoromethyl)-2-(trifluoromethyl)-3,5-pyridinedicarboxylate To a solution of 7.92 g (0.02 mol) of product of Example 79 in 70 ml of ethanol was added 8.4 ml (0.021 mol) of 10% NaOH and was left stirring at 25° C. for 1 hour. The reaction mixture was poured into 3.7% HCl, extracted with $CH_2Cl_2$ (2X), dried ($MgSO_4$) and solvent removed in vacuo affording 6.78 g (92%) of crude product as a yellow solid. A portion of this crude solid was recrystallized from hot ethyl acetate/hexane followed by drying at an oven temperature of 80° C./80 Pa affording pure product as a white solid; mp 120.5°–122.0° C.

Anal. Calc'd. for $C_{14}H_{13}F_3N_2O_4$: C, 45.66; H, 3.56; N, 7.61. Found: C, 45.76; H, 3.58; N, 7.59.

EXAMPLE 85

Diethyl 4-cyclopropylamino-6-methyl-2-(trifluoromethyl)-3,5-pyridinedicarboxylate A mechanically stirred mixture of 3.22 g (0.008 mol) of product of Example 79, 14 g (0.214 mol) of zinc dust and 14 ml of trifluoroacetic acid in 100 ml of $CH_2Cl_2$ was refluxed for 48 hours. The reaction mixture was cooled to room temperature, decanted into $H_2O$ and extracted with $CH_2Cl_2$. The $CH_2Cl_2$ phase was washed with a saturated solution of $NaHCO_3$ and dried ($MgSO_4$). Solvent was removed in vacuo affording 2.4 g of a thick yellow oil. This crude product was purified using the HPLC and 5% ethyl acetate/cyclohexane as eluting solvent, followed by kugelrohr distillation at 100°–130° C./67 Pa affording 1.29 g (48%) of product as a light yellow oil, $n_D^{25}$ 1.4978.

Anal. Calc'd. for $C_{16}H_{19}F_3N_2O_4$: C, 53.33; H, 5.31; N, 7.77. Found: C, 53.28; H, 5.34; N, 7.76.

EXAMPLE 86

4-Cyclopropylamino-6-(difluoromethyl)-2-(trifluoromethyl)-3,5-pyridinedicarboxylic acid A solution of 17.68 g (0.04 mol) of product of Example 79, 22.4 g (0.4 mol) of KOH and 30 ml of $H_2O$ in 100 ml of ethanol was refluxed for 18 hours. Ethanol was removed in vacuo, and the residue poured into 10% HCl and extracted twice with ethyl acetate. The combined ethyl acetate was washed with saturated NaCl, dried ($MgSO_4$) and concentrated in vacuo affording 15.12 g of a brown solid. A 2 g portion of this solid was recrystallized from ethyl acetate/hexane to give 1.7 g (94%) of product as a beige solid; mp 183°–184° C. (dec.).

Anal. Calc'd. for $C_{12}H_9F_5N_2O_4$: C, 42.36; H, 2.67; N, 8.23. Found: C, 42.45; H, 2.71; N, 8.23.

EXAMPLE 87

Dimethyl 4-cyclopropylamino-6-(difluoromethyl)-2-(trifluoromethyl)-3,5-pyridinedicarboxylate A mixture of 13 g (0.04 mol) of product of Example 86, 28.4 g (12.5 ml, 0.2 mol) of $CH_3I$ and 11.04 g (0.08 mol) of $K_2CO_3$ in 100 ml of DMF was stirred at room temperature for 19 hours. The reaction mixture was poured into $H_2O$, extracted with ether (2X), washed with $H_2O$ (2X), dried ($MgSO_4$) and concentrated in vacuo affording 14.54 g of a brown solid. This crude product was recrystallized in ether/hexane to give 11.31 g (77%) of product as a gold colored solid; mp 63°–64° C.

Anal. Calc'd. for $C_{14}H_{13}F_5N_2O_4$: C, 45.66; H, 3.56; N, 7.61. Found: C, 45.56; H, 3.58; N, 7.59.

EXAMPLE 88

3-Methyl 5-hydrogen 4-cyclopropylamino-6-(difluoromethyl)-2-(trifluoromethyl)-3,5-pyridinedicarboxylate monohydrate To a solution of 7.19 g (0.02 mol) of product of Example 87 in 70 ml of methanol was added 8.4 ml (0.021 mol) of 10% NaOH. The reaction mixture was stirred at 25° C. for 1 hour. The methanol was reduced in vacuo and residue was poured into 5% NaOH. This aqueous phase was washed with diethyl ether, acidified with concentrated HCl, extracted twice with $CH_2Cl_2$ and dried ($MgSO_4$). Solvent was removed in vacuo affording 6.17 g of a solid containing a mixture of diacid and monoacid. This solid was fractionally recrystallized affording 2.17 g (32%) of product as a beige solid; mp 83°–85° C.

Anal. Calc'd. for $C_{13}H_{11}F_5N_2O_4[H_2O]$: C, 41.94; H, 3.52; N, 7.53. Found: C, 41.66; H, 3.26; N, 7.45.

EXAMPLE 89

Diethyl 6-(chlorodifluoromethyl)-4-(isopropylamino)-2-(trifluoromethyl)-3,5-pyridinedicarboxylate To a solution of 3 g (0.0073 mol) of product of Example 30 and 0.81 g (1.1 ml, 0.008 mol) of triethylamine in 10 ml of DMF was added slowly 0.47 g (0.7 ml, 0.008 mol) of isopropylamine. An exotherm was observed raising the reaction temperature to 45° C. The reaction mixture was stirred at room temperature for 1 hour, poured into $H_2O$ and extracted with diethyl ether. The ether layer was washed with 10% HCl, twice with $H_2O$ and dried ($MgSO_4$). Solvent was removed in vacuo and residue was kugelrohr distilled at 110°–120° C.//47 Pa affording 2.47 g (78%) of product as a light yellow oil, $n_D^{25}$ 1.4713.

Anal. Calc'd. for $C_{16}H_{18}Cl_1F_5N_2O_4$: C, 44.40; H, 4.19; N, 6.47; Cl, 8.19. Found: C, 44.43; H, 4.19; N, 6.42; Cl, 8.22.

EXAMPLE 90

5-Ethyl 3-methyl 4-cyclopropylamino-6-(difluoromethyl)-2-(trifluoromethyl)-3,5-pyridinedicarboxylate This compound was prepared as described in Example 87: 1.5 g (0.0044 mol) of product of Example 88, 2.74 g (1.4 ml, 0.0176 mol) of ethyl iodide and 0.69 g (0.005 mol) of $K_2CO_3$ in 25 ml of DMF were reacted affording 1.5 g of an oil. Crude was kugelrohr distilled at 110°–130° C./60 Pa to give 1.22 g (73%) of product as a white solid; mp 52°–53° C.

Anal. Calc'd. for $C_{15}H_{15}F_5N_2O_4$: C, 47.13; H, 3.96; N, 7.33. Found: C, 47.09; H, 3.98; N, 7.29.

EXAMPLE 91

3-Ethyl 5-methyl 4-cyclopropylamino-6-methyl-2-(trifluoromethyl)-3,5-pyridinedicarboxylate This compound was prepared as described in Example 85: 17 g (0.264 mol) of zinc dust, 4.76 g (0.012 mol) of product of Example 56 and 17 ml of trifluoroacetic acid in 100 ml of $CH_2Cl_2$ were reacted affording 2.44 g (59%) of product after kugelrohr distillation at 100°–140° C./53 Pa as a light yellow oil, $n_D^{25}$ 1.5032.

Anal. Calc'd. for $C_{15}H_{17}F_3N_2O_4$: C, 52.02; H, 4.95; N, 8.09. Found: C, 51.88; H, 5.00; N, 8.01.

PREPARATION OF FURTHER 4-ALKOXY COMPOUNDS FROM 4-HALO COMPOUNDS

EXAMPLE 92

3-Ethyl 5-methyl 6-(chlorodifluoromethyl)-4-(2,2,2-trifluoroethoxy)-2-(trifluoromethyl)-3,5-pyridinedicarboxylate To 100 ml of dry THF was added 0.29 g (0.013 mol) of sodium metal. To this mixture 1.28 g (0.013 mol) of 2,2,2-trifluoroethanol was added dropwise. The solution was stirred under $N_2$ until all of the sodium metal had been consumed. Then 5.0 g (0.0126 mol) of product of Example 28 was added to the sodium salt solution and the reaction mixture was allowed to stir at room temperature for 4 hours. The reaction mixture was poured into 100 ml of $H_2O$, and extracted with diethyl ether. The ether phase was dried ($MgSO_4$) and concentrated in vacuo to yield 5.48 g of a gold crystalline solid. This solid was recrystallized in hexane to yield 4.2 g (72.4%) of product as a tan solid; mp 62°–63° C.

Anal. Calc'd. for $C_{14}H_{10}Cl_1F_8N_1O_5$: C, 36.58; H, 2.19; N, 3.05. Found: C, 36.21; H, 2.16; N, 2.99.

EXAMPLE 93

3-Ethyl 5-methyl 6-(difluoromethyl)-4-(2,2,2-trifluoroethoxy)-2-(trifluoromethyl)-3,5-pyridinedicarboxylate A 2.5 g (0.0054 mol) portion of product from Example 92, 1.09 g (0.011 mol) of triethylamine and 0.25 g of 5% Pd/C (50% water coated) in 75 ml of ethanol was hydrogenated under 446 kPa. of $H_2$ pressure for 18 hours at room temperature. The mixture was then filtered, and concentrated in vacuo to remove the ethyl alcohol. The residue was poured into water and extracted with diethyl ether. The ether extract was washed with $H_2O$, then dried ($MgSO_4$). The dry ether phase was then concentrated in vacuo to yield 2.21 g of the crude product as a tan solid. The crude product was then recrystallized in hexane to yield 2.00 g (86.5%) of product as a beige solid; mp 66°–67° C.

Anal. Calc'd. for $C_{14}H_{11}F_8N_1O_5$: C, 39.54; H, 2.61; N, 3.29. Found: C, 39.56; H, 2.73; N, 3.17.

PREPARATION OF PYRIDINE DICARBOXYLATES VIA ROUTE 2

The following Examples 94–173 illustrate the preparation of compounds of this invention using the enamine diester method designated above as Route 2. Examples 94 and 97 illustrate the preparation of the enamine diester compounds themselves from the acetonedicarboxylate starting material, and reaction of the enamine diester with a fluorinated or chlorofluorinated acetic anhydride. Examples 94, 97, and 99 show the preparation of 4-aminopyridinedicarboxylate compounds by reaction of the resulting 3-amino-2-halo-acetyl-2-pentenedioate intermediate with a fluorinated or chlorofluorinated acetonitrile.

EXAMPLE 94

Diethyl 4-cyclopropylamino-2,6-bis(chlorodifluoromethyl)-3,5-pyridinedicarboxylate Step A: Preparation of diethyl 3-cyclopropylamino-2-pentenedioate: To 30.33 g (0.15 mol) of diethyl acetonedicarboxylate was added dropwise 11.8 g (0.19 mol) of cyclopropylamine at such a rate that reaction temperature was kept below 48° C. The reaction mixture was stirred at room temperature for 18 hours. The reaction mixture was poured into $H_2O$, extracted twice with ether, dried ($MgSO_4$) and concentrated in vacuo affording 34.42 g of a light yellow oil. Crude was kugelrohr distilled at 53 Pa and collected at a pot temperature of 102°–104° C. to give 23.73 g (66%) of enamine diester as a light yellow oil, $n_D^{25}$1.5025.

Anal. Calc'd. for $C_{12}H_{19}N_1O_4$: C, 59.73; H, 7.94. Found: C, 59.57; H, 7.96.

Step B: Preparation of pyridine dicarboxylate product: To an ice-cooled solution of 24.1 g (0.1 mol) of the enamine diester from Step A, and 12.14 g (17 ml, 0.12 mol) of triethylamine in 75 ml of anhydrous ether was added dropwise 34.16 g (0.14 mol) of chlorodifluoroacetic anhydride in such rate that reaction temperature was kept below 10° C. After stirring at room temperature for 2 hours, the reaction mixture was poured into water, extracted with ether, dried ($MgSO_4$) and concentrated to give 35 g (99% yield, 74% pure) of a brown oil. A portion of this crude material was then reacted as follows:

To 65 ml of DME cooled to 5° C. in a magnetically stirred flask with thermometer and dry-ice condenser was added 14.5 g (0.13 mol) of $CF_2ClCN$ via subsurface tube. To this solution 21.21 g (0.06 mol) of the crude product of Step B was added, followed by 16.7 ml (0.12 mol) of triethylamine. The reaction mixture is warmed to 25° C., resulting in mild reflux of the nitrile. Dry ice was maintained in the condenser for 2 hours and the reaction mixture is stirred at 25° C. for 18 hours. The reaction mixture was poured into 2% HCl/3% NaCl solution, extracted with $CH_2Cl_2$ (3X). The combined extracts were washed with 1% HCl/3% NaCl, then twice with 1% NaOH/3% NaCl solution. After drying ($MgSO_4$), the extracts were filtered, concentrated and the residue (18.92 g of a dark brown oil) kugelrohr distilled at 110 –160° C./67 Pa affording 12.94 g (56%) of a thick amber oil. For elemental analysis a 2 g portion was subjected to HPLC using 10% ethyl acetate/cyclohexane as eluting solvent, followed by kugelrohr distillation at 130°–160° C./106 Pa affording 1.66 g of product as a yellow oil, $n_D^{25}$1.5350.

Anal. Calc'd. for $C_{16}H_{16}Cl_2F_4N_2O_4$: C, 42.97; H, 3.61; N, 6.26; Cl, 15.85. Found: C, 43.03; H, 3.65; N, 6.24; Cl, 15.79.

EXAMPLE 95

Diethyl 4-cyclopropylamino-2,6-bis(difluoromethyl)-3,5-pyridinedicarboxylate This compound was prepared as described in Example 22: 10.62 g (0.024 mol) of product of Example 94, 4.86 g (6.7 ml, 0.048 mol) of triethylamine, 0.53 g of 5% Pd/C and 100 ml ethanol were hydrogenated affording 6.51 g of a light yellow solid. Crude was recrystallized in ethyl acetate/hexane affording 3.12 g (34%) of product as a light beige solid; mp 84°–85° C.

Anal. Calc'd. for $C_{16}H_{18}F_4N_2O_4$: C, 50.80; H, 4.80; N, 7.40. Found: C, 50.96; H, 4.80; N, 7.39.

EXAMPLE 96

Dimethyl 4-cyclopropylamino-2,6-bis(difluoromethyl)-3,5-pyridinedicarboxylate ¼ hydrate To a solution of 2.1 g (0.0056 mol) of product of Example 95 in 70 ml of ethanol was added 8.4 mol (0.021 mol) of 10% aqueous NaOH and stirred at room temperature for 19 hours. Ethanol was removed in vacuo, and the residue poured into 3.7% HCl, extracted with ethyl acetate (3X), dried ($MgSO_4$) and solvent concentrated affording 1.6 g of the diacid as a white foamy solid. This solid was treated with 4.26 g (1.9 ml, 0.03 mol) of $CH_3I$ and 1.38 g (0.01 mol) of $K_2CO_3$ in 20 ml of DMF for 19 hours. The crude was poured into $H_2O$ and then extracted with ether. The ether layer was washed with saturated $Na_2CO_3$ and twice with $H_2O$. Organic layer was dried ($MgSO_4$) and solvent removed in vacuo affording 1.6 g of crude beige solid as a mixture of two products. This crude mixture was fractionally crystallized using ether to give 0.87 g (49%) of product as a white solid; mp 114°–115° C.

Anal. Calc'd. for $C_{14}H_{14}F_4N_2O_4[\frac{1}{4}H_2O]$: C, 47.40; H, 4.12; N, 7.90. Found: C, 47.35; H, 4.01; N, 7.73.

EXAMPLE 97

Diethyl 2,6-bis(trifluoromethyl)-4-benzylamino-3,5-pyridinedicarboxylate

Step A: Preparation of diethyl 3-benzylamino-2-pentenedioate: To 50.00 g (0.247 mol) of diethyl acetonedicarboxylate was added dropwise 31.79 g (0.297 mol) of benzylamine at such a rate that reaction temperature was kept below 50° C. The reaction mixture was stirred at room temperature for 12 hours and poured into $H_2O$, extracted twice with ether, dried ($MgSO_4$) and concentrated in vacuo affording 60.00 g of a yellow-green oil. Crude was purified by HPLC using 10% ethyl acetate/cyclohexane affording 46.2 g of a yellow semi solid. This was kugelrohr distilled at 53 Pa and collected at a pot temperature of 148°–150° C. to give 39.4 g (55%) of enamine diester as a beige crystalline solid; mp 34°–36° C.

Anal. Calc'd. for $C_{16}H_{21}N_1O_4$: C, 65.96; H, 7.27; N, 4.81. Found: C, 65.91; H, 7.32; N, 4.79.

Step B: Preparation of Diethyl 3-benzylamino-2-trifluoroacetyl-2-pentenedioate: To a 0° C. solution of 13.0 g (0.0446 mol) of product from Step A and 5.26 (7.3 ml, 0.052 mol) of triethylamine in 65 ml of anhydrous ether was added dropwise 10.93 g (7.45 ml, 0.052 mol) of trifluoroacetic anhydride at such a rate that the reaction temperature was kept below 10° C. Reaction mixture was stirred at 0° C. for 1 hour, then poured into $H_2O$, extracted twice with diethyl ether and dried ($MgSO_4$). Solvent was removed in vacuo affording 16.0 g of a yellow solid. This was recrystallized in hexane/ether to give 15.0 g (89.6%) of this intermediate as a yellow crystalline solid; mp 63°–65° C.

Anal. Calc'd. for $C_{18}H_{20}F_1O_5[\frac{1}{2}H_2O]$: C, 54.54; H, 5.34; N, 3.53. Found: C, 54.67; H, 5.11; N, 3.41.

Step C: Preparation of pyridine dicarboxylate product: To a 0° C. solution of 16.02 g (0.168 mol) of $CF_3CN$ in 60 ml of DME equipped with dry-ice condenser was added dropwise a solution of 30 g (0.080 mol) of product of Step B in 25 ml of DME. The reaction temperature was allowed to rise to 5° C. and 16.1 g (22.17 ml, 0.160 mol) of triethylamine was added in such a rate that the reaction temperature did not rise above 10° C. Reaction mixture was allowed to come to room temperature, and stirred for 2 hours. The reaction mixture was poured into 2% HCl and extracted with diethyl ether. The ether phase was washed with 2% NaOH, and dried (MgSO$_4$). The dry ether phase was concentrated in vacuo yielding 28.0 g of a gold crystalline material. This was kugelrohr distilled at 67 Pa and collected at a pot temperature of 154°–155° C. affording 16.0 g (44%) of a yellow-gold crystalline solid product; mp 58°–62° C.

Anal. Calc'd. for $C_{20}H_{18}F_6N_2O_4$: C, 51.73; H, 3.91; N, 6.03. Found: C, 51.74; H, 3.95; N, 6.00.

EXAMPLE 98

Diethyl 2,6-bis(trifluoromethyl)-4-amino-3,5-pyridinedicarboxylate

A mixture 1.75 g (0.0038 mol) of product from Example 97, 1 ml of 3.7% HCl, 0.175 g of 5% palladium on carbon (50% water coated) in 70 ml of ethanol was hydrogenated at 446 kPa and 55° C. for 72 hours. The mixture was filtered through celite, and concentrated in vacuo to remove the ethanol. The residue was taken up in H$_2$O, and extracted with diethyl ether. This was dried over MgSO$_4$, and concentrated in vacuo to 0.90 g of crude. This brown solid was kugelrohr distilled at 67 Pa and was collected at a pot temperature of 135° C. affording 0.6 g (42%) of product as a tan solid; mp 52°–58° C.

Anal. Calc'd. for $C_{13}H_{12}R_6N_2$: C, 41.72; H, 3.23; N, 7.49. Found: C, 41.83; H, 3.34; N, 7.19.

EXAMPLE 99

Diethyl 6-(chlorodifluoromethyl)-4-benzylamino-2-(trifluoromethyl)-3,5-pyridinedicarboxylate To a 0° C. solution of 183.97 g (1.65 mol) of CF$_2$ClCN in 690 ml of DME equipped with dry-ice condenser was added dropwise a solution of 296 g (0.764 mol) of the crude product of Step B in Example 97 in 250 ml of DME. The mixture was stirred at 0° C. for 10 minutes, at which time 159.47 g (1.576 mol) of triethylamine was dripped in at such a rate that the reaction temperature remained below 10° C. Reaction was allowed to warm to room temperature then poured into 2% HCl/2% NaCl and extracted with diethyl ether. The ether phase was washed with 2% NaOH, dried (MgSO$_4$), and concentrated in vacuo to 348 g of a black semi-solid oil. The crude product was kugelrohr distilled at 53 Pa and collected at a pot temperature of 154°–155° C. affording 140 g (37%) of product as a yellow solid; mp 49°–53° C.

Anal. Calc'd. for $C_{20}H_{18}Cl_1F_5N_2O_4$: C, 49.96; H, 3.77; N, 5.83; Cl, 7.37. Found: C, 50.02; H, 3.78; N, 5.76; Cl, 7.38.

EXAMPLE 100

Diethyl 6-(difluoromethyl)-4-amino-2-(trifluoromethyl)-3,5-pyridinedicarboxylate A mixture of 340 g (0.722 mol) of product from Example 99, 87.67 g (0.866 mol) of triethylamine and 10.00 g of 5% Pd/C (50% water coated) in 700 ml of ethanol was hydrogenated at 50° C. under 446 kPa of H$_2$ pressure for 18 hours. Then 150 ml of 18% HCl (0.722 mol) was added, and the mixture was hydrogenated at 50° C. under 446 of H$_2$ pressure for 2 hours. The reaction mixture was filtered through celite, and concentrated in vacuo to remove the ethanol. The residue was taken up in H$_2$O, and extracted with diethyl ether. The ether phase was dried (MgSO$_4$) and concentrated in vacuo to 161.7 g (65%) of a brown oil, 90% pure by GC analysis. Then 5.0 g were purified by HPLC in 5% ethyl acetate/cyclohexane affording 3.9 g of product as a yellow solid; mp 29°–30° C.

Anal. Calc'd. $C_{13}H_{13}F_5N_2O_4$: C, 43.83; H, 3.68; N, 7.86. Found: C, 43.91; H, 3.68; N, 7.83.

EXAMPLE 101

3-Ethyl 5-hydrogen 2-(trifluoromethyl)-4-amino-6-(difluoromethyl)-3,5-pyridinedicarboxylate To a stirred solution of 122.5 g (0.344 mol) of product of Example 100 in 125 ml of ethanol was added 137 ml of 10% NaOH (0.344 mol) slowly. After stirring at room temperature of 1 hour, reaction was complete ($^{19}$F-NMR). The solution was poured into 1 L of 10% HCl and extracted with 500 ml of ether. The ether layer was washed with one 500 ml portion of 10% HCl, dried (CaSO$_4$), filtered and concentrated to 100 g (87%) of off-white solid; mp 142.5°–151° C. Recrystallization from chloroform gave an analytical sample; mp 169.5°–171° C.

Anal. Calc'd. for $C_{11}H_9F_5N_2O_4$: C, 40.26; H, 2.76; N, 8.54. Found: C, 40.22; H, 2.69; N, 8.50.

EXAMPLE 102

3-Ethyl 5-methyl 6-(difluoromethyl)-4-(dimethylsulfilamino)-2-(trifluoromethyl)-3,5-pyridinecarboxylate To a mechanically stirred solution of 1.81 g (0.023 mol) of anhydroux dimethyl sulfoxide, in 35 ml of anhydrous methylene chloride under an N$_2$ atmosphere at −78° C. was added 4.44 g (0.016 mol) of trifluoromethanesulfonic anhydride at such a rate that the reaction temperature was maintined at −78° C. To this was added a solution of 4.5 g (0.013 mol) of product of Example 64 in 25 ml of dry CH$_2$Cl$_2$. The resulting yellow suspension was stirred at −78° C. for 2 hours. The reaction temperature was warmed to −55° C., and stirred for 1 hour, then warmed to 0° C. and stirred for 45 minutes. The reaction mixture was quenched with 5% aqueous NaOH. This was accomplished at such a rate that the reaction temperature did not rise above 5° C. To this mixture 50 ml of CH$_2$Cl$_2$ was added. This was stirred for 5 minutes then separated. The H$_2$O phase was extracted again with CH$_2$Cl$_2$. The combined CH$_2$Cl$_2$ phases were washed with H$_2$O, and dried (Na$_2$SO$_4$). The dry CH$_2$Cl$_2$ phase was concentrated in vacuo to 4.3 g of a yellow solid. The crude product was recrystallized in hexane/methylene chloride affording 1.8 g (34%) of a white solid product; mp 121°–122° C.

Anal. Calc'd. for $C_{14}H_{15}F_5N_2O_4$: C, 41.79; H, 3.76; N, 6.96; S, 7.97. Found: C, 41.70; H, 3.69; N, 6.94; S, 8.00.

EXAMPLE 103

3-Ethyl 5-methyl 6-(difluoromethyl)-4-chloro-2-(trifluoromethyl)-3,5-pyridinecarboxylate To a mechanically stirred solution of 25.93 g (0.195 mol) of copper (II) chloride, and 25.16 g (0.244 mol) of t-butylnitrite in 1 L of $CH_3CN$, was added a solution of 54 g (0.157 mol) of product of Example 64 in 400 ml of $CH_3CN$, at such a rate, that a slow evolution of $N_2$ gas was observed. After 16 hours the reaction mixture was refluxed for 6 hours, cooled to room temperature poured into 3.7% HCl, and extracted with diethyl ether. The ether phase was washed with $H_2O$, and dried ($MgSO_4$). The dry ether phase was concentrated in vacuo to 39.6 g (65%) of a yellow oil. HPLC in 2% ethyl acetate/cyclohexane afforded an analytical sample; mp 24°–25° C.

Anal. Calc'd. for $C_{12}H_9Cl_1F_5N_1O_4$: C, 39.85; H, 2.51; N, 3.87; Cl, 9.8. Found: C, 40.10; H, 2.54; N, 4.14; Cl, 10.26.

EXAMPLE 104

Diethyl 2,6-bis(trifluoromethyl)-4-bromo-3,5-pyridinedicarboxylate

To a mechanically stirred solution of 6.54 g (0.029 mol) of copper (II) bromide, and 3.77 g (0.037 mol) of t-butylnitrite in 100 ml of aceto-nitrile, was added a solution of 8.9 g (0.024 mol) of product of Example 98 in 30.0 ml of acetonitrile at such a rate that a slow evolution of $N_2$ observed. After 18 hours the mixture was poured into 3.7% HCl and extracted with diethyl ether. The ether phase was washed with $H_2O$ and dried ($MgSO_4$). The ether phase was concentrated in vacuo to 7.9 g of a tan solid. This crude was recrystallized in hexane affording 7.07 g (66%) of product as a green-brown solid; mp 56°–61° C.

Anal. Calc'd. for $C_{13}H_{10}Br_1F_6N_1O_4$: C, 35.64; H, 2.30; N, 3.20. Found: C, 35.75; H, 2.30; N, 3.18.

EXAMPLE 105

Diethyl 6-(difluoromethyl)-4-chloro-2-(trifluoromethyl)-3,5-pyridinedicarboxylate To a mechanically stirred mixture of 11.52 g (0.087 mol) of copper (II) chloride, and 11.18 g (0.108 mol) of t-butylnitrite in 350 ml of $CH_3CN$, was added a solution of 25.00 g (0.070 mol) of product of Example 100 in 25 ml of $CH_3CN$ in such a rate that a slow evolution of $N_2$ was observed. After 18 hours the mixture was poured into 3.7% HCl, and extracted with diethyl ether. The ether phase was washed with $H_2O$ and dried ($MgSO_4$). This was concentrated in vacuo to 24.03 g of a yellow oil. The crude product was purified by HPLC in 5% ethyl acetate/cyclohexane affording 13.2 g (50%) of product as a yellow solid; mp 35°–40° C.

Anal. Calc'd. for $C_{13}H_{11}Cl_1F_5N_1O_4$: C, 41.56; H, 2.95; N, 3.73. Found: C, 41.40; H, 2.96 N, 4.00.

EXAMPLE 106

Diethyl 6-(difluoromethyl)-4-bromo-2-(trifluoromethyl)-3,5-pyridinedicarboxylate To a mechanically stirred solution of 19.31 g (0.087 mol) of copper (II) bromide and 11.18 g (0.108 mol) of t-butylnitrite in 350 ml of $CH_3CN$ was added a solution of 25.0 g (0.070 mol) of product of Example 100 in 25 ml of $CH_3CN$. This was added at such a rate that a slow evolution of $N_2$ was observed. After 18 hours the mixture was poured into 3.7% HCl and extracted with diethyl ether. The ether phase was washed with $H_2O$, and dried ($MgSO_4$). The dry ether phase was concentrated in vacuo to 23.3 g of a brown oil. The crude product was purified by HPLC in 5% ethyl acetate/cyclohexane affording 11.59 g (39%) of product as a yellow crystalline solid; mp 37°–43° C.

Anal. Calc'd. for $C_{13}H_{11}Br_1F_5N_1O_4$: C, 37.16; H, 2.64; N, 3.33. Found: C, 37.54; H, 2.71; N, 3.72.

EXAMPLE 107

3-Ethyl 5-methyl 6-(difluoromethyl)-4-fluoro-2-(trifluoromethyl)-3,5-pyridinedicarboxylate The reagent was prepared by dissolving 0.37 g (0.001 mol) of 18-crown-6 in 30 ml of dry $CH_3CN$ (distilled over $CaH_2$) and then adding 3.25 g (0.056 mol) of dry KF (dried in an oven at 50° C./67 Pa). After the heterogeneous system was mechanically stirred for 30 minutes, 10 g (0.028 mol) of product of Example 103 was added and the resulting mixture was refluxed for 6 days. The reaction mixture was poured into $H_2O$, extracted with diethyl ether (2X), dried ($MgSO_4$) and solvent removed in vacuo affording 9.45 g of a brown oil. The crude product was purified by HPLC using 1% ethyl acetate/cyclohexane as eluting solvent affording 6.72 g (70%) of product as a white solid; mp 40°–41° C.

Anal. Calc'd. for $C_{12}H_9F_6N_1O_4$: C, 41.75; H, 2.63; N, 4.06. Found: C, 42.05; H, 2.70; N, 3.97.

EXAMPLE 108

Diethyl 4-(t-butylthio)-6-(difluoromethyl, 2-(trifluoromethyl)-3,5-pyridinecarboxylate A mixture of 0.44 g (0.011 mol) of 60% of NaH in mineral oil dispersion was washed twice with 10 ml portions of dry THF. To the resulting oil free NaH was added 30 ml of dry THF followed by 1.08 g (1.4 ml, 0.012 mol) of t-butylmercaptan. The resulting mixture was heated up to 50° C. for 20 minutes and a white precipitate was formed. This suspension was added dropwise at room temperture to a solution of 4.20 g (0.01 mol) of product of Example 106 in 40 ml of dry THF. The reaction temperature rose to 35° C. After stirring at room temperature for 3 hours, the reaction mixture was poured into 3.7% HCl. The aqueous layer was extracted twice with diethyl ether, dried ($MgSO_4$) and concentrated to give 4.23 g of a light yellow oil. The crude product was purified by HPLC using 2% EtOAC/cyclohexane as eluting solvent followed by kugelrohr distillation at 100°–110° C./100 Pa to give 2.86 g (67%) of product as a colorless oil, $n_D^{25}$ 1.4678.

Anal. Calc'd. for $C_{17}H_{20}F_5N_1O_4S_1$: C, 47.55; H, 4.69; N, 3.26; S, 7.47. Found: C, 47.69; H, 4.71; N, 3.20; S, 7.57.

EXAMPLE 109

Diethyl 4-cyclopentylthio-6-(difluoromethyl)-2-(trifluoromethyl)-3,5-pyridinedicarboxylate This compound was prepared as described in Example 108: 8.4 g (0.02 mol) of product of Example 106, 0.88 g (0.022 mol) of 60% NaH, and 2.45 g (0.024 mol) of cyclopentylmercaptan in 100 ml of dry THF were reacted affording 8.85 g of a light brown oil. The crude product mixture was kugelrohr distilled at 110°–130° C./67 Pa affording 8.44 g 96%) of product as a light yellow oil, $n_D^{25}$ 1.4808.

Anal. Calc'd. for $C_{18}H_{20}F_5N_1O_4S_1$: C, 48.98; H, 4.57; N, 3.17; S, 7.26. Found: C, 49.12; H, 4.60; N, 3.15; S, 7.35.

EXAMPLE 110

3-Ethyl 5-methyl 4-(t-butylthio)-6-(difluoromethyl)-2-(trifluoromethyl)-3,5-pyridinedicarboxylate This product was prepared as described in Example 108: 3 g (0.0083 mol) of product of Example 103, 0.90 g (1.13 ml, 0.01 mol) of t-butylmercaptan and 0.36 g (0.009 mol) of 60% NaH in 50 ml of dry THF were reacted affording 2.92 g (85%) of product after kugelrohr distillation at 100°–110° C./67 Pa as a light yellow oil, $n_D^{25}$ 1.4710.

Anal. Calc'd. for $C_{16}H_{18}F_5N_1O_4S_1$:: C, 46.26; H, 4.37; N, 3.37; S, 7. 2. Found: C, 46.46; H, 4.41; N, 3.34; S, 7.77.

EXAMPLE 111

3-Ethyl 5-methyl 4-(cyclopentylthio)-6-(difluoromethyl)-2-(trifluoromethyl)-3,5-pyridinedicarboxylate This compound was prepared as described in Example 108: 3 g (0.0083 mol) of product of Example 103, 1.02 g (0.01 mol) of cyclopentylmercaptan and 0.36 g (0.009 mol) of 60% NaH in 50 ml of dry THF were reacted affording 3.8 g of a red oil. Crude was purified by HPLC using 1 % ethyl acetate/cyclohexane as eluting solvent to give 2.5 g of a light yellow oil which gas chromatography showed to be 94% pure. This material was passed through a spinning plate preparative chromatograph in two different portions of 1.25 g each (eluting solvent: 40% $CH_2Cl_2$/cyclohexane) to give, after kugelrohr distillation at 105°–125° C./106 Pa, 1.95 g (55%) of product as a clear oil; $n_D^{25}$ 1.4831.

Anal. Calc'd. for $C_{17}H_{18}F_5N_1O_4S_1$: C, 47.77; H, 4.25; N, 3.28; S, 7.50. Found: C, 47.85; H, 4.28; N, 3.27; S, 7.54.

EXAMPLE 112

Diethyl 6-(difluoromethyl)-4-(N-methylcyclopropylamino)-2-(trifluoromethyl)-3,5-pyridinedicarboxylate To a mixture of 6.0 g (0.017 mol) of product from Example 105, 1.71 g (0.017 mol) of triethylamine in 30 ml of DMF was added 1.76 g (0.025 mol) of N-methylcyclopropylamine at such a rate that the temperature remained below 30° C. After 4 hours the reaction mixture was poured into 3.7% HCl and extracted with diethyl ether. The ether phase was washed with $H_2O$, and dried ($MgSO_4$). The dry ether phase was concentrated in vacuo to 5.8 g of a green oil. The crude product was purified by HPLC in 5% ethyl acetate/cyclohexane, followed by kugelrohr distillation at 67 Pa, oven temperature 150° C., affording 1.02 g (15.5%) of product as a green oil, $n_D^{25}$ 1.4758.

Anal. Calc'd for $C_{17}H_{19}F_5N_2O_4$: C, 49.76; H, 4.67; N, 6.83. Found: C, 49.89; H, 4.74; N, 6.83.

EXAMPLE 113

Diethyl 6-(difluoromethyl)-4-(t-butylamino)-2-(trifluoromethyl)-3,5-pyridinedicarboxylate A solution of 6.0 g (0.015 mol) of product from Example 106, 1.48 g (0.0147 mol) of triethylamine and 2.15 g (0.0244 mol) of t-butylamine in 30 ml of DMF was stirred at 50° C. for 12 hours. The reaction mixture was poured into $H_2O$, and extracted with diethyl ether. The ether phase was washed with $H_2O$, and dried ($MgSO_4$). The dry ether phase was concentrated in vacuo to 2.8 g of a brown oil. The crude product was kugelrohr distilled at 67 Pa and collected at a pot temperature of 154°–155° C. affording 2.5 g (42%) of product as a beige solid; mp 30°–31° C.

Anal. Calc'd. for $C_{17}H_{21}F_5N_2O_4$: C, 49.52; H, 5.13; N, 6.79. Found: C, 49.29; H, 5.13; N, 6.73.

EXAMPLE 114

3-Ethyl 5-methyl 6-(difluoromethyl)-4-(N-methylcyclopropylamino)-2-(trifluoromethyl)-3,5-pyridinedicarboxylate A solution of 5.0 g (0.008 mol) of product from Example 103, 0.83 g (0.0082 mol) of triethylamine and 0.875 g (0.012 mol) of N-methylcyclopropylamine in 100 ml of DMF was stirred at room temperature for 12 hours. The reaction mixture was poured into $H_2O$ and extracted with diethyl ether. The ether phase was washed with $H_2O$ and dried ($MgSO_4$). The dry ether phase was concentrated in vacuo to 2.4 g of a yellow oil. The crude product was purified by HPLC in 10% ethyl acetate/cyclohexane followed by kugelrohr distillation at 67 Pa and 125° C. pot temperature, affording 1.6 g (49%) of product as a yellow solids; mp 37°–40° C.

Anal. Calc'd. for $C_{16}H_{17}F_5N_2O_4$: C, 48.49; H, 4.32; N, 7.07. Found: C, 48.59; H, 4.34; N, 7.04.

EXAMPLE 115

3-Ethyl 5-methyl 6-(difluoromethyl)-4-(cyanomethylamino)-2-(trifluoromethyl)-3,5-pyridinedicarboxylate A solution of 3.0 g (0.008 mol) of product of Example 103, 1.72 g (0.017 mol) of triethylamine and 0.79 g (0.008 mol) of aminoacetonitrile hydrochloride in 30 ml of DMF was stirred at 50° C. for 24 hours. The reaction mixture was cooled to room temperature and poured into 3.7% HCl. This solution was extracted with diethyl ether. The ether phase was washed with $H_2O$, and dried ($MgSO_4$). The dry ether phase was concentrated in vacuo to 2.56 g of a brown semi-solid oil. The crude product was recrystallized in hexane/ethyl acetate to 0.9 g (28%) of product as a beige solid; mp 87°–89° C.

Anal. Calc'd. for $C_{14}H_{12}F_5N_3O_4$: C, 44.10; H, 3.17; N, 11.02. Found: C, 43.94; H, 3.19; N, 10.94.

EXAMPLE 116

3-Ethyl 5-methyl 6-(difluoromethyl)-4-(dimethylamino)-2-(trifluoromethyl)-3,5-pyridinedicarboxylate A solution of 3.46 g (0.010 mol) of the compound produced in Example 103, 0.97 g (0.010 mol) of triethylamine and 2.00 g (0.012 mol) of a 26% W/V solution of aqueous dimethylamine in 50 ml of DMF was stirred at room temperature for 18 hours. The reaction mixture was poured into 3.7% HCl and extracted with diethyl ether. The ether phase was washed with H₂O, and dried (MgSO₄). The dry ether phase was con-centrated in vacuo to 2.6 g of a yellow solid. This crude product was purified using the HPLC in 5% ethyl acetate/cyclohexane, affording 2.39 g (67%) of a yellow solid; mp 80°-81° C.

Anal. Calc'd. for $C_{14}H_{15}F_5N_2O_4$: C, 45.41; H, 4.08; N, 7.57. Found: C, 45.56; H, 4.12; N, 7.56.

EXAMPLE 117

3-Ethyl 5-methyl 2-(trifluoromethyl)-6-(difluoromethyl)-4-[1-(2,5-dimethyl-3-pyrrolyl)]-3,5-pyridinedicarboxylate To a solution of 5 g (0.014 mol) of product of Example 103, and 1.33 g (0.014 mol) of 2,5-dimethyl-3-pyrroline in 50 ml of DMF was added 1.4 g (0.013 mol) of triethylamine slowly. After 2½ hours at room temperature the reaction stopped at about ⅓ completion. (Starting pyridine was still present by gas chromatography.) An additional 2.4 g (0.026 mol) of 2,5-dimethyl-3-pyrroline was added. After stirring at room temperature for 24 hours, the reaction was 60% complete by gas chromatography. The starting pyrroline is a mixture of cis and trans isomers and only the cis isomer reacted. The solution was poured into a 50/50 mixture of ether/water. The ether layer was separated and washed with two 50 ml portions of water, dried (CaSO₄), filtered and concentrated to 3.7 g of red oil which is a 60:40 mixture of product and starting pyridine. Purification by HPLC (10% ethyl acetate/cyclohexane) gave 2.1 g (36%) of pure product, $n_D^{25}$ 1.4670.

Anal. Calc'd. for $C_{18}H_{19}F_5N_2O_4$: C, 51.19; H, 4.53; N, 6.63. Found: C, 50.98; H, 4.50; N, 6.41.

EXAMPLE 118

3-Ethyl 5-methyl 2-(trifluoromethyl)-6-(difluoromethyl)-4-[1-(2,5-dimethyl-pyrrolidinyl)]-3,5-pyridinedicarboxylate To a solution of 5 g (0.014 mol) of product of Example 103, and 1.4 g (0.014 mol) of 2,5-dimethylpyrrolidine in 60 ml of DMF was added 1.4 g (0.014 mol) of triethylamine slowly. After stirring for 6 hours at room temperature the reaction was complete, the mixture was poured into 200 ml of a 50/50 mixture of ether/water. The ether layer was separated and washed with two 100 ml portions of dilute saline solution, dried (CaSO₄), filtered and concentrated to 4.5 g of red oil which was about 90% pure product, but still wet with ether. HPLC (10% ethyl acetate/cyclohexane) gave 2.8 g (47%) of pure product, $n_D^{25}$ 1.4636.

Anal. Calc'd. for $C_{18}H_{21}F_5N_2O_4$: C, 50.94; H, 4.99; N, 6.60. Found: C, 51.03; H, 5.01; N, 6.53.

EXAMPLE 119

3-Ethyl 5-methyl 2-(trifluoromethyl)-6-(difluoromethyl)-4-(1-pyrazolyl)-3,5-pyridinedicarboxylate To a solution of 0.94 g (0.014 mol) of pyrazole in 25 ml of anhydrous tetrahydrofuran was added 0.9 g (0.014 mol) of n-butyllithium. This cloudy solution was then transferred to a solution of 5 g (0.014 mol) of product of Example 103 in 25 ml of anhydrous THF. The solution turned red upon addition of the pyrazole lithium salt. After 45 minutes at room temperature the reaction was complete. The mixture was poured into 100 ml of water and extracted with two 75 ml portions of ether. The combined ether layers were washed with two 100 ml portions of water, dried (CaSO₄), filtered and concentrated to 4.1 g of oil which was about 80% product. Trituration with petroleum ether gave 2.4 g (45%) of pure product; mp 42°-52° C. Recrystallization from cyclohexane afforded an analytical sample; mp 48.5°-50° C.

Anal. Calc'd. for $C_{15}H_{12}F_5N_3O_4$: C, 45.81; H, 3.08; N, 10.68. Found: C, 45.72; H, 3.11; N, 10.63.

EXAMPLE 120

3-Ethyl 5-methyl 6-(difluoromethyl)-4-(diethoxyphosphinyl)-2-(trifluoromethyl)-3,5-pyridinedicarboxylate To a mixture of 0.26 g (0.011 mol) of sodium metal in 35 ml of dry THF was added 3.14 g (0.023 mol) of diethyl phosphite. This solution was stirred at room temperature under a N₂ atmosphere for 18 hours. To this salt solution was added 2.0 g (0.006 mol) of product of Example 107. This mixture was stirred at reflux for 18 hours. The mixture was cooled to room temperature and poured into H₂O. The H₂0 mixture was extracted twice with diethyl ether. The combined ether phases were then washed with H₂O, dried (MgSO₄), and concentrated in vacuo affording 2.18 g of an orange oil. This oil was kugelrohr distilled at 80 Pa and collected at 150°-151° C. pot temperature yielding 1.68 g (63%) of a clear oil, $n_D^{25}$ 1.4536.

Anal. Calc'd. for $C_{16}H_{19}F_5N_1O_7P_1$: C, 41.48; H, 4.13; N, 3.02. Found: C, 41.76; H, 4.15; N, 3.03.

Using procedures similar to those set out in detail, other pyridinedicarboxylate compounds were prepared. The following Table 1 sets out the pyridinedicarboxylates so prepared, along with a physical property for each:

TABLE 1

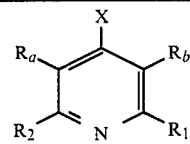

| Example | R₁ | R₂ | Rₐ | R_b | X | mp | $n_D^{25}$ |
|---|---|---|---|---|---|---|---|
| 121 | CF₂H | CF₃ | C(O)OEthyl | C(O)OMethyl | t-butylamino | 27-29 | |
| 122 | CF₂H | CF₃ | C(O)OEthyl | C(O)OMethyl | ethylamino | 79-81 | |
| 123 | CF₃ | CF₂H | C(O)OMethyl | C(O)OEthyl | cyclohexylamino | | 1.4881 |
| 124 | CF₂H | CF₃ | C(O)OEthyl | C(O)OMethyl | 2,2-dimethyl-propylamino | | 1.4694 |
| 125 | CF₂H | CF₃ | C(O)OEthyl | C(O)OMethyl | cyclopentyl-amino | 48-50 | |
| 126 | CF₃ | CF₂H | C(O)OMethyl | C(O)OEthyl | 1-methyl-propylamino | | 1.4732 |

TABLE 1-continued

Structure: pyridine with X at 4-position, $R_a$ at 3, $R_b$ at 5, $R_2$ at 2, $R_1$ at 6, N in ring.

| Example | $R_1$ | $R_2$ | $R_a$ | $R_b$ | X | mp | $n_D^{25}$ |
|---|---|---|---|---|---|---|---|
| 127 | CF$_2$H | CF$_3$ | C(O)OEthyl | C(O)OMethyl | methylamino | 49-51 | |
| 128 | CF$_2$H | CF$_3$ | C(O)OEthyl | C(O)OMethyl | 2-propenyl-amino | 105-107 | |
| 129 | CF$_2$H | CF$_3$ | C(O)OEthyl | C(O)ONa | cyclopropyl-amino | 189-191 | |
| 130 | CF$_2$H | CF$_3$ | C(O)OEthyl | C(O)SCH$_3$ | cyclopropyl-amino | | 1.5177 |
| 131 | CF$_2$H | CF$_3$ | C(O)OEthyl | C≡N | cyclopropyl-amino | 73-77 | |
| 132 | CF$_2$H | CF$_3$ | C(O)OMethyl | C(O)OMethyl | ethylamino | 85-87 | |
| 133 | CF$_2$H | CF$_3$ | C(O)OMethyl | C(O)OMethyl | 2,2-dimethyl-1-aziridinyl | | 1.4743 |
| 134 | CF$_2$H | -CF$_3$ | C(O)OEthyl | C(O)SEthyl | Cyclopropyl-amino | 48-51 | |
| 135 | CF$_2$H | CF$_3$ | C(O)OEthyl | C(O)N(Methyl)$_2$ | cyclopropyl-amino | 100-102 | |
| 136 | CF$_2$H | CF$_3$ | C(O)OEthyl | C(O)NHBenzyl | cyclopropyl-amino | 101-102 | |
| 137 | CF$_2$H | CF$_3$ | C(O)OEthyl | C(O)OMethyl | 1-piperidinyl | 43-44 | |
| 138 | CF$_2$H | CF$_3$ | C(O)OEthyl | C(O)OMethyl | trifluoroaceto-amino | 124-125 | |
| 139 | CF$_2$H | CF$_3$ | C(O)OEthyl | C(O)OMethyl | IH-1,2,4-tria-zol-1-yl | 83.5-85.0 | |
| 140 | CF$_2$Cl | CF H | C(O)OMethyl | C(O)OMethyl | cyclopropyl-amino | 70-74 | |
| 141 | CF$_2$Cl | CF$_2$Cl | C(O)OMethyl | C(O)OMethyl | cyclopropyl-amino | 91-92.5 | |
| 142 | CF$_3$ | CF$_2$H | C(O)OMethyl | C(O)OMethyl | hexamethylene-imine | | 1.4746 |
| 143 | CF$_2$H | CF$_3$ | C(O)OEthyl | C(O)OMethyl | diacetylamino | 60-62 | |
| 144 | CF$_2$H | CF$_3$ | C(O)OEthyl | C(O)OMethyl | 1-ethylpropyl-amino | | 1.4744 |
| 145 | CF$_3$ | CF$_2$Cl | C(O)OEthyl | C(O)OEthyl | cyclobutylamino | | 1.4873 |
| 146 | CF$_2$H | CF$_3$ | C(O)OEthyl | C(O)OMethyl | methoxyamino | | 1.4775 |
| 147 | CF$_2$H | CF$_3$ | C(O)OEthyl | C(O)OEthyl | cyclobutyl-amino | | 1.4882 |
| 148 | CF$_3$ | CF$_3$ | C(O)OMethyl | C(O)OMethyl | cyclopropyl-amino | 71-72 | |
| 149 | CF$_2$H | CF$_3$ | C(O)OEthyl | C(O)OMethyl | 2,4-dimethyl-6-oxa-3-azabicyclo[3.1.0] hexan-3-yl | | 1.4704 |
| 150 | CF$_2$H | CF$_3$ | C(O)OEthyl | C(O)OMethyl | octahydro-1-azocinyl | | 1.4828 |
| 151 | CF$_3$ | CFCl$_2$ | C(O)OMethyl | C(O)OMethyl | cyclopropylamino | | 1.5105 |
| 152 | CF$_3$ | CFH$_2$ | C(O)OMethyl | C(O)OMethyl | cyclopropylamino | | 1.5054 |
| 153 | CF$_3$ | CF$_2$H | C(O)OMethyl | C(O)OEthyl | 2,2,2-trifluoro-1-methoxyethylidene-amino | | 1.4391 |
| 154 | CF$_2$H | CF$_3$ | C(O)OEthyl | C(O)NHMethyl | cyclopropyl-amino | 119-121 | |
| 155 | CF$_2$H | CF$_3$ | C(O)OEthyl | C(O)OH | cyclobutyl-amino | 90-92 | |
| 156 | CF$_2$H | CF$_3$ | C(O)OEthyl | C(O)Cl | cyclobutyl-amino | 68-69 | |
| 157 | CF$_2$H | CF$_3$ | C(O)OEthyl | C(O)NH$_2$ | cyclobutyl-amino | 127-129 | |
| 158 | CF$_2$H | CF$_3$ | C(O)OEthyl | C(O)N(Methyl)$_2$ | cyclobutylamino | 100-102 | |
| 159 | CF$_2$H | CF$_3$ | C(O)OEthyl | C(O)NHMethyl | cyclobutylamino | 132-133 | |
| 160 | CF$_2$H | CF$_3$ | C(O)OEthyl | C≡N | cyclobutylamino | 67-68 | |
| 161 | CF$_2$H | CF$_3$ | C(O)OEthyl | C(O)S isopropyl | cyclopropyl-amino | | 1.518 |
| 162 | CF$_2$H | CF$_3$ | C(O)OEthyl | C(O)Cl | cyclopropylamino | 39-45 | |
| 163 | CF$_2$H | CF$_3$ | C(O)OEthyl | C(O)SMethyl | cyclobutylamino | 51-53 | |
| 164 | CF$_2$Cl | CF$_3$ | C(O)OMethyl | C(O)OMethyl | benzylamino | 68.0-69.5 | |
| 165 | CF$_2$H | CF$_3$ | C(O)OMethyl | C(O)OMethyl | cyclobutoxy | 59.5-60.5 | |
| 166 | CF$_2$H | CF$_3$ | C(O)OEthyl | C(O)OMethyl | 2,2,2-trifluoro-1-methylethoxy | 30-31 | |
| 167 | CF$_2$H | CF$_3$ | C(O)OEthyl | C(O)OMethyl | 2,2,2-trifluoro-1,1,-dimethyl-ethoxy | | 1.435 |
| 168 | CF$_2$H | CF$_3$ | C(O)OEthyl | C(O)OMethyl | 2,2,2-trifluoro- | 52-55 | |

TABLE 1-continued

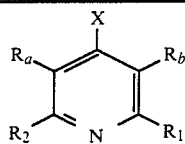

| Example | $R_1$ | $R_2$ | $R_a$ | $R_b$ | X | mp | $n_D^{25}$ |
|---|---|---|---|---|---|---|---|
| 169 | $CF_2H$ | $CF_3$ | C(O)OEthyl | C(O)OMethyl | 1-(trifluoromethyl)ethoxy 4,5-dihydro-2-thiazolylthio | | 1.5026 |
| 170 | $CF_2H$ | $CF_3$ | C(O)OEthyl | C(O)OMethyl | cyanothio | 38.5–39.5 | |
| 171 | $CF_2H$ | $CF_3$ | C(O)OEthyl | C(O)OMethyl | 1-methyl-1H-imidazol-2-ylthio | | 1.5117 |
| 172 | $CF_2H$ | $CF_3$ | C(O)OEthyl | C(O)OMethyl | 2,2-dimethylaziridinyl | | 1.4758 |
| 173 | $CF_2H$ | $CF_3$ | C(O)OEthyl | $C(O)NH_2$ | cyclobutylamino | 127–129 | |

EXAMPLE 174

Dimethyl 4-(cyclopropylamino)-2-(pentafluoroethyl)-6-(trifluoromethyl)-3,5-pyridinedicarboxylate Step A: Preparation of dimethyl 3-(cyclopropylamino)-2-pentenedioate This compound was prepared as described in Step A of Example 94: 190.6 g (1.09 mol) of dimethyl acetonedicarboxylate and .75 g (1.3 mol) of cyclopropylamine in 200 ml of ether were reacted affording 194 g of clear oil. Trituration with petroleum ether gave 171.5 g (74%) of the enamine diester as a white solid: mp 64°–70° C. Crystallization from cyclohexane afforded an analytical sample; mp 73°–75° C.

| Analysis calculated for $C_{10}H_{15}N_1O_4$ | | | |
|---|---|---|---|
| Elemental Analysis: | C | H | N |
| Calculated | 56.33 | 7.09 | 6.57 |
| Found | 56.49 | 7.12 | 6.54 |

Step B: Preparation of dimethyl 3-(cyclopropylamino)-2-(trifluoroacetyl)-2-pentenedioate This compound was prepared as described in Step B of Example 97: 40 g (0.19 mol) of product of Step A and 39.9 g (27 ml, 0.19 mol) of trifluoroacetic anhydride in 300 ml of anhydrous ether were reacted affording 52.59 g of a light yellow solid. This solid was recrystallized in $Et_2O$/hexane affording 49.46 g (84%) of a white solid; mp 51.5°–52.5° C.

| Analysis calculated for $C_{12}H_{14}F_3N_1O_5$ | | | |
|---|---|---|---|
| Elemental Analysis: | C | H | N |
| Calculated | 46.73 | 4.57 | 4.52 |
| Found | 46.73 | 4.57 | 4.52 |

Step C: Preparation of pyridine dicarboxylate product:

This compound was prepared as described in Step C of Example 97: 10 g (0.032 mol) of product of Step B, 9.28 g (0.064 mol) of $CF_3CF_2CN$ and 6.08 g (6 ml, 0.04 mol) of DBU in 150 ml of DME were reacted affording 18.5 g of a yellow oil. Crude was purified by HPLC using 30% $CH_2Cl_2$/cyclohexane as eluting solvent followed by kugelrohr distillation at 100°–120° C. (0.6 mm Hg°) affording 7.38 g (53%) of product as a yellow oil, $n_D^{25}$ 1.4541.

| Analysis calculated for $C_{15}H_{12}F_8N_2O_4$ | | | |
|---|---|---|---|
| Elemental Analysis: | C | H | N |
| Calculated | 41.30 | 2.77 | 6.42 |
| Found | 41.62 | 2.82 | 6.50 |

EXAMPLE 175

Dimethyl 2-(chlorodifluoromethyl)-4-(isopropylamino)-6-(trifluoromethyl)-3,5-pyridinedicarboxylate This compound was prepared by reacting the corresponding trifluoroacetylated enamine diester with $CF_2ClCN$ as described in Example 174; mp 34°–36° C.

| Analysis calculated for $C_{14}H_{14}Cl_1F_5N_2O_4$ | | | | |
|---|---|---|---|---|
| Elemental Analysis: | C | H | N | Cl |
| Calculated | 41.55 | 3.49 | 6.92 | 8.76 |
| Found | 41.42 | 3.49 | 7.02 | 8.98 |

EXAMPLE 176

Dimethyl 2-(chlorodifluoromethyl)-4-(cyclopropylamino)-6-(trifluoromethyl)-3,5-pyridinedicarboxylate This compound was prepared by reacting the corresponding trifluoroacetylated enamine diester with $CF_2ClCN$ as described in Example 174; mp 77°–78° C.

| Analysis calculated for $C_{14}H_{12}Cl_1F_5N_2O_4$ | | | | |
|---|---|---|---|---|
| Elemental Analysis: | C | H | N | Cl |
| Calculated | 41.76 | 3.00 | 6.96 | 8.80 |
| Found | 41.64 | 3.01 | 6.94 | 8.80 |

Using procedures similar to those set out in detail, other pyridinedicarboxylate compounds were prepared. The following Table 2 sets out the pyridinedicarboxylates so prepared, along with a physical property for each.

TABLE 2

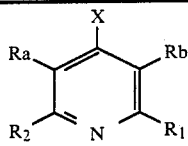

| Example | $R_1$ | $R_2$ | Ra | Rb | X | mp °C. | $n_D^{25}$ |
|---|---|---|---|---|---|---|---|
| 177 | $CF_2H$ | $CF_3$ | $CO_2CH_2Ph$ | $CO_2CH_2Ph$ | cyclopropylamino | 88–89 | |
| 178 | $CF_2H$ | $CF_3$ | $CO_2Et$ | $CO_2Me$ | N-methyl-N-isopropylamino | 42–44 | |
| 179 | $CF_2H$ | $CF_3$ | $CO_2CH_2Ph$ | $CO_2CH_2Ph$ | isopropylamino | | 1.5355 |
| 180 | $CF_2H$ | $CF_3$ | $CO_2Et$ | $CO_2Me$ | (1-methylcyclopropyl)amino | 61–63 | |
| 181 | $CF_2H$ | $CF_3$ | $CO_2CH_2Ph$ | $CO_2Me$ | isopropylamino | 56–57 | |
| 182 | $CF_2H$ | $CF_3$ | $CO_2H$ | $CO_2H$ | cyclobutylamino | 183–184 | |
| 183 | $CF_2H$ | $CF_3$ | CO(SMe) | CO(SMe) | cyclobutylamino | 88–89 | |
| 184 | $CF_2H$ | $CF_3$ | $CO_2Me$ | $CO_2Me$ | amino | 77–79 | |
| 185 | $CF_3$ | $CH_3$ | $CO_2Me$ | $CO_2Me$ | cyclopropylamino | | 1.5008 |
| 186 | $CF_2H$ | $CF_3$ | $CO_2Me$ | $CO_2H$ | amino | 181.5–183.0 | |
| 187 | $CF_2H$ | $CF_3$ | $CO_2H$ | $CO_2H$ | amino | 222 (dec) | |

EXAMPLE 188

S,S-Dimethyl 2-(difluoromethyl)-4-(isopropylamino)-6-(trifluoromethyl)-3,5-pyridinedicarbothioate To a solution of 87.13 g (0.235 mol) of product of Example 76 in 600 ml of 30% aqueous ethanol was added 188 ml (2.35 mol) of 50% aqueous NaOH and refluxed for 18 hours. The ethanol was removed in vacuo and the residue was poured into 3% HCl, extracted with EtOAc and dried ($MgSO_4$). Solvent was removed affording 74.64 g (93%) of diacid as a beige solid. A portion of this solid (21.38 g, 0.063 mol) was treated with 26 g (0.125 mol) of $PCl_5$ in 250 ml of $CCl_4$ at 25° C. for 18 hours. The solvent was removed in vacuo affording 26.6 g (99%) of the diacid chloride. A solution of this diacid chloride in 100 ml of anhydrous THF was treated with 13.1 g (0.19 mol) of $CH_3SNa$ and heated at 60° C. for 2 hours. The reaction was cooled to 25° C., poured into 3% HCl, extracted with $Et_2O$. $Et_2O$ layer was washed with saturated NaCl and dried ($MgSO_4$). Solvent was removed in vacuo affording 23.16 g of crude product as a dark brown oil. Crude was purified by HPLC using 4% EtOAc/cyclohexane affording 10.94 g (44%) of product as a yellow solid; mp 92°–94° C.

| Analysis calculated for $C_{14}H_{15}F_5N_2O_2S_2$ | | | | |
|---|---|---|---|---|
| Elemental Analysis: | C | H | N | S |
| Calculated | 41.79 | 3.76 | 6.96 | 15.94 |
| Found | 42.15 | 3.72 | 7.01 | 16.03 |

EXAMPLE 189

Methyl 3-[(methylthio)carbonyl]-6-(difluoromethyl)-4-amino-2-(trifluoromethyl)-5-pyridinecarboxylate Step A: Preparation of diacid chloride To a mechanically stirred suspension of 8.2 g (0.027 mol) of product of Example 187 in 100 ml of $CCl_4$ at 25° C. was added 11.94 g (0.057 mol) of $PCl_5$. This suspension was heated at 50° C. for 3 hours, then cooled to 25° C. filtered and concentrated in vacuo to 8.5 g (93%) of the diacid chloride as a white powder.

Step B: Preparation of Pyridine Product

To 7.25 g (0.022 mol) of product of Step A in 100 ml of anhydrous THF at 0° C. was added 0.69 g (0.022 mole) of anhydrous $CH_3OH$. This mixture was warmed to 25° C. and stirred for 18 hours. The mixture was then concentrated in vacuo to 6.75 g (0.02 mol) of the monoacid chloride as a beige solid. To a 0° C. solution of 6.7 g (0.02 mol) of this beige solid in 80 ml of anhydrous THF was added 1.4 g (0.02 mol) of $NaSCH_3$. This mixture was allowed to warm to 25° C. and stirred for 18 hours. The reaction mixture was poured into $H_2O$, and extracted with diethyl ether. The ether phase was washed with $H_2O$, and dried ($MgSO_4$). The dry ether phase was concentrated in vacuo to 5.7 g of an orange oil. Crude was purified by HPLC in 55% $CH_2Cl_2$/cyclohexane affording 2.8 g (40%) of product as a white solid; mp 96°–98° C.

| Analysis Calculated for $C_{11}H_9F_5N_2O_3S_1$ | | | | |
|---|---|---|---|---|
| Elemental Analysis: | C | H | N | S |
| Calculated | 38.38 | 2.69 | 8.14 | 9.31 |
| Found | 38.49 | 2.67 | 8.07 | 9.35 |

EXAMPLE 190

Methyl 3-[(methylthio)carbonyl]-6-(difluoromethyl)-4-(cyclopropylamino)-2-(trifluoromethyl)-5-pyridinecarboxylate To a mechanically stirred mixture of 0.99 g (0.007 mol) of $CuCl_2$ and 1.03 g (0.01 mol) of t-butyl nitrite in 40 ml of $CH_3CN$ was added dropwise a solution of 2.00 g (0.07 mol) of product of Example 189 in 10 ml of $CH_3CN$. Evolution of $N_2(g)$ was observed and reaction mixture was stirred at 25° C. for 18 hours. Crude mixture was poured into 3.7% HCl, extracted twice with diethyl ether, washed with $H_2O$, dried ($MgSO_4$) and concentrated in vacuo to 2.19 g of the 4-chloropyridine as a white solid. To a magnetically stirred solution of 2.19 g (0.006 mol) of this white solid and 0.73 g (0.007 mol) of triethylamine in 40 ml of DMF at 25° C. was added dropwise 0.40 g (0.007 mol) of cyclopropylamine. After 18 hours the reaction mixture was poured into $H_2O$, and extracted with diethyl ether. The ether phase was washed with $H_2O$, and dried ($MgSO_4$). The dry ether phase was concentrated in vacuo to 1.7 g of a beige solid. Crude was recrystallized from hexane/EtOAc affording 1.2 g (52%) of product as a white solid; mp 180°–109° C.

| Analysis calculated for $C_{14}H_{13}F_5S_1N_2O_3$ | | | |
|---|---|---|---|
| Elemental Analysis: | C | H | N |
| Calculated | 43.75 | 3.41 | 7.29 |
| Found | 43.76 | 3.44 | 7.26 |

EXAMPLE 191

S,S-Dimethyl 6-(difluoromethyl)-4-amino-2-(trifluoromethyl)-3,5-pyridinedicarbothioate To a magnetically stirred solution of 10.0 g (0.03 mol) of product of Step A in Example 189 in 100 ml of anhydrous THF at 25° C. was added 4.2 g (0.06 mol) of NaSCH$_3$. This mixture was stirred for 18 hours. The reaction mixture was poured into 3.7% HCl(aq), and extracted with diethyl ether. The ether phase was washed with H$_2$O, and dried (MgSO$_4$). The dry ether phase was filtered and concentrated in vacuo to 9.4 g (87%) of a beige solid. A portion of this solid was recrystallized from hexane/EtOAc affording the product as a beige solid; mp 160°–161° C.

| Analysis calculated for $C_{11}H_9F_5N_2O_2S_2$ | | | | |
|---|---|---|---|---|
| Elemental Analysis: | C | H | N | S |
| Calculated | 36.67 | 2.52 | 7.77 | 17.80 |
| Found | 36.68 | 2.54 | 7.77 | 17.72 |

EXAMPLE 192

S,S-Dimethyl 6-(difluoromethyl)-4-(cyclopropylamino)-2-(trifluoromethyl)-3,5-pyridinedicarbothioate To a mechanically stirred mixture of 0.78 g (0.006 mol) of CuCl$_2$, and 0.75 g (0.007 mol) of t-butylnitrite in 40 ml of CH$_3$CN at 25° C. was added dropwise a solution of 1.7 g (0.0047 mol) of product of Example 191 in 10 ml of CH$_3$CN. Evolution of N$_2$ was observed and reaction mixture was stirred for 18 hours. The crude mixture was poured into 3.7% HCl(aq), and extracted with diethyl ether. The ether phase was washed with H$_2$O and dried (MgSO$_4$). The dry ether phase was concentrated in vacuo to 1.55 g (0.004 mol) of the 4-chloropyridine as a yellow solid. To a magnetically stirred solution of 1.55 g (0.004 mol) of this yellow solid, and 0.50 g (0.005 mol) of triethylamine in 40 ml of DMF at 25° C. was added dropwise 0.28 g (0.005 mol) of cyclopropylamine. After 18 hours the reaction mixture was poured into H$_2$O, and extracted with diethyl ether. The ether phase was washed with H$_2$O, dried (MgSO$_4$), and concentrated in vacuo affording 1.2 g of a brown solid. The crude was purified by preparatory centrifugally-accelerated radical thin-layer chromatography in 10% EtOAc/cyclohexane yielding 0.4 g (25%) of product as a yellow solid; mp 85°–86° C.

| Analysis calculated for $C_{14}H_{13}F_5N_2O_2S_2$ | | | | |
|---|---|---|---|---|
| Elemental Analysis: | C | H | N | S |
| Calculated | 42.00 | 3.27 | 7.00 | 16.02 |
| Found | 42.07 | 3.31 | 7.00 | 16.18 |

EXAMPLE 193

Methyl 3-[(ethylthio)carbonyl]-6-(difluoromethyl)-4-amino-2-(trifluoromethyl)-5-pyridinecarboxylate To a solution of 10 g (0.03 mol) of product of Step A in Example 189 in 100 ml of anhydrous THF at 25° C. was added 0.95 g (0.03 mol) of CH$_3$OH. This solution was stirred for 18 hours at 25° C. The solution was concentrated in vacuo to 9.85 g (0.03 mol) of the monoacid chloride as a brown solid. To a room temperature suspension of 0.031 mol of sodium hyride in 50 ml of anhydrous THF was added 2.08 g (0.034 mol) of ethanethiol. This suspension was stirred for 45 minutes at 25° C. To this suspension was added dropwise a solution of 9.4 g (0.03 mol) of the monoacid chloride in 30 ml of THF. This mixture was stirred at 25° C. for 1 hour. The reaction mixture was poured into 3.7% HCl (aq), and extracted with diethyl ether. The ether phase was washed with 3.7% HCl, and dried (MgSO$_4$). The dry organic phase was concentrated in vacuo to 11.1 g of a brown solid. The crude was recrystallized from hexane/EtOAc affording 6.00 g (60%) of product as a beige solid; mp 72°–74° C.

| Analysis calculated for $C_{12}H_{11}F_5N_2O_3S_1$ | | | | |
|---|---|---|---|---|
| Elemental Analysis: | C | H | N | S |
| Calculated | 40.23 | 3.09 | 7.82 | 8.95 |
| Found | 40.37 | 3.14 | 7.71 | 8.83 |

EXAMPLE 194

Methyl 3-[(ethylthio)carbonyl]-6-(difluoromethyl)-4-(cyclopropylamino)-2-(trifluoromethyl)-5-pyridinecarboxylate Step A: Preparation of 4-chloropyridine To a mechanically stirred mixture of 2.3 g (0.02 mol) of CuCl$_2$ and 2.3 g (0.02 mol) of t-butylnitrite in 100 ml of CH$_3$CN was added dropwise a solution of 5.0 g (0.014 mol) of product of Example 193 in 40.0 ml of CH$_3$CN. Evolution of N$_2$(g) was observed, and the reaction mixture was stirred at 25° C. for 18 hours. The crude mixture was poured into 3.7% HCl (aq), extracted twice with diethyl ether, washed with 3.7% HCl(aq), dried (MgSO$_4$), and concentrated in vacuo to 4.8 g (0.01 mol) of the 4-chloropyridine as a yellow solid.

Step B: Preparation of 4-cyclopropylaminopyridine

To a magnetically stirred, 25° C. solution of 2.3 g (0.006 mol) of product of Step A and 0.71 g (0.007 mol) of triethylamine in 40 ml of DMF was added dropwise 0.38 g (0.007 mol) of cyclopropylamine. After 18 hours the reaction mixture was poured into H$_2$O and extracted with diethyl ether. The ether phase was washed with H$_2$O, and dried (MgSO$_4$). The dry ether phase was concentrated in vacuo to 1.95 g of a brown solid. The crude was recrystallized from hexane/EtOAc affording 1.2 g (50%) of product as a beige solid; mp 111°–112° C.

| Analysis calculated for $C_{15}H_{15}F_5N_2O_3S_1$ | | | | |
|---|---|---|---|---|
| Elemental Analysis: | C | H | N | S |
| Calculated | 45.23 | 3.80 | 7.03 | 8.05 |

-continued

| Analysis calculated for $C_{15}H_{15}F_5N_2O_3S_1$ | | | | |
|---|---|---|---|---|
| Elemental Analysis: | C | H | N | S |
| Found | 45.30 | 3.83 | 6.96 | 8.01 |

EXAMPLE 195

Methyl 3-[(ethylthio)carbonyl]-6-(difluoromethyl)-4-(isopropylamino)-2-(trifluoromethyl)-5-pyridinecarboxylate To a magnetically stirred solution of 2.3 g (0.006 mol) of product of Step A of Example 194 and 0.71 g (0.007 mol) of triethylamine in 40 ml of DMF at 25° C. was added dropwise 0.41 g (0.007 mol) of isopropylamine. After 18 hours the crude reaction mixture was poured into $H_2O$, and extracted with diethyl ether. The ether phase was washed with $H_2O$ and dried ($MgSO_4$). The dry ether phase was concentrated in vacuo to 3.6 g of a brown semi-solid. The crude was recrystallized from hexane/EtOAc affording 0.85 g (34%) of product as a beige solid; mp 56°–59° C.

| Analysis calculated for $C_{15}H_{17}F_5N_2O_3S_1$ | | | | |
|---|---|---|---|---|
| Elemental Analysis: | C | H | N | S |
| Calculated | 45.00 | 4.28 | 7.00 | 8.01 |
| Found | 44.92 | 4.33 | 6.97 | 7.95 |

EXAMPLE 196

4-Amino-6-(difluoromethyl)-3-[(methylthio)carbonyl]-2-(trifluoromethyl)-5-pyridinecarboxylic acid A solution of 40.8 g (0.113 mol) of product of Example 191, 400 ml of ethanol and 4.5 g (0.113 mol) of 10% aqueous sodium hydroxide was stirred at 25° C. for 5 days. Another 2 g (0.05 mol) of sodium hydroxide was added and stirring continued for 24 hours. The reaction mixture was then diluted with ethyl acetate and washed with three 500 ml portions of 5% HCl, dried ($CaSO_4$), filtered and concentrated to 31.4 g (84%) of product as a yellow solid; mp 219° C. (dec).

| Analysis calculated for $C_{10}H_7F_5N_2O_3S_1$ | | | |
|---|---|---|---|
| Elemental Analysis: | C | H | N |
| Calculated | 36.37 | 2.14 | 8.48 |
| Found | 36.40 | 2.23 | 8.29 |

EXAMPLE 197

5-Methyl 3-ethyl 4-[(1-chloro-2,2,2-trifluoroethylidene)amino]-6-(difluoromethyl)-2-(trifluoromethyl)-3,5-pyridinedicarboxylate Into a 25 ml flask was placed 10 g (0.023 mol) of product of Example 138 and 4.8 g (0.023 mol) of $PCl_5$. This was heated at 140° C. for 3 hours. Kugelrohr distillation of the reaction mixture gave 6.2 g (59%) of product as a clear oil that turns to a white semi-solid upon standing.

| Analysis calculated for $C_{14}H_9Cl_1F_8N_2O_4$ | | | |
|---|---|---|---|
| Elemental Analysis: | C | H | N |
| Calculated | 36.82 | 1.99 | 6.13 |
| Found | 36.91 | 1.99 | 6.12 |

EXAMPLE 198

Dimethyl 2-(difluoromethyl)-4-hydroxy-6-(trifluoromethyl)-3,5-pyridinedicarboxylate Product of Example 18 (23.34 g, 0.032 mol), 9.0 ml (0.064 mol) of triethylamine and 0.62 g of Pd/C (10%) in 100 ml of EtOH were reacted as described by the preparation of product of Example 22 affording 9.99 g of dark orange oil. A portion of this oil (5.0 g, 0.014 mol), 4.51 g (0.070 mol) of 87% KOH, 1 ml of $H_2O$ in 30 ml of EtOH was stirred at reflux for 5 days. Reaction mixture was concentrated and the residue was poured into water and washed with ether. The aqueous layer was acidified with conc HCl, extracted with ether, dried ($MgSO_4$) and concentrated in vacuo to 4.26 g of foamy oil. This oil was treated as described in Example 19: 4.26 g (0.013 mol) of this foamy oil, 25 ml of thionyl chloride and 25 ml of MeOH were reacted affording a dark solid residue which was taken up in ether and extracted with 15% $K_2CO_3$ and water, acidified with concentrated HCl, extracted with ether, dried ($MgSO_4$) and concentrated in vacuo in 2.7 g of solid. Recrystallization from hexane-ether afforded 1.37 g (32.0%) of product as a tan solid: mp 83°–84.5° C.

| Analysis calculated for $C_{11}H_8F_5N_1O_5$ | | | |
|---|---|---|---|
| Elemental Analysis: | C | H | N |
| Calculated | 40.14 | 2.45 | 4.26 |
| Found | 40.00 | 2.47 | 4.23 |

EXAMPLE 199

3-Ethyl 5-methyl 4-[(α-bromocyclopropylcarbonyl)amino]-2-(trifluoromethyl)-6-(difluoromethyl)-3,5-pyridinedicarboxylate To a mixture of 0.264 g (0.011 mol) of sodium hydride in 25 ml of anhydrous THF was added, dropwise, 2 g (0.0046 mol) of product of Example 138 in 10 ml of anhydrous THF. This mixture was heated at 45° C. until gas evolution ceased. The mixture was then cooled to 25° C. and 2 g (0.011 mol) of α-bromocyclopropyl carboxylicacid chloride was added. This was then heated to reflux for 4 hours. The reaction mixture was then diluted with ether and washed with three 100 ml portions of 5% HCl, dried ($CaSO_4$), filtered and concentrated to 4.1 g of yellow oil which is about 60% product. Chromatography (10% EtoAC/cyclohexane) gave 1.2 g (53%) of product as a white solid. Trituration with petroleum ether gave an analytical sample; mp 83°–85° C.

| Analysis calculated for $C_{16}H_{14}Br_1F_5N_2O_5$ | | | |
|---|---|---|---|
| Elemental Analysis: | C | H | N |
| Calculated | 39.28 | 2.88 | 5.73 |
| Found | 39.37 | 2.90 | 5.75 |

EXAMPLE 200

Methyl 6-(trifluoromethyl)-4-isopropylamino-5-(1H-pyrazol-1-ylcarbonyl)-2-(difluoromethyl)-3-pyridinecarboxylate To a solution of 46.27 g (0.1 mol) of product of Example 181 in 200 ml of THF and 1 liter of CH$_3$OH was added 6 g of 5% Pd/C (50% H$_2$O), and the mixture was hydrogenated at 50 psi of H$_2$ for 48 hours. The crude was passed through celite and the solvent was removed in vacuo affording 35 g of crude monoacid. This crude acid was then treated with 23 g of PCl$_5$ in 400 ml of CCl$_4$. The resulting mixture was refluxed for one-half hour, cooled and reduced in vacuo affording 38.04 g of crude acid chloride as a yellow oil. A portion of this oil (3.75 g, 0.01 mol) was treated with 1.36 g (0.02 mol) of pyrazole in 25 ml of anhydrous ether for 18 hours. The crude mixture was poured into 3.7% HCl and extracted twice with EtOAc. The organic layer was dried (MgSO$_4$) and reduced in vacuo to a light yellow solid. The crude was washed with hexane affording 3.49 g (86%) of product as a white solid: mp 80°–81° C.

| Analysis calculated for C$_{16}$H$_{15}$F$_5$N$_4$O$_3$ | | | |
|---|---|---|---|
| Elemental Analysis: | C | H | N |
| Calculated | 47.30 | 3.72 | 13.79 |
| Found | 47.37 | 3.75 | 13.35 |

EXAMPLE 201

Methyl 6-(difluoromethyl)-4-(isopropylamino)-2-(trifluoromethyl)-3-[(methylamino)carbonyl]-5-pyridinecarboxylate To a mixture of 10 g (0.03 mol) of the acid chloride prepared in Example 200 in 500 mL of Et$_2$O was added an excess of anhydrous methyl amine and the mixture was stirred at 30° C. for 4 hours. The reaction mixture was cooled to 25° C., and concentrated in vacuo to a white powder which was extracted with CHCl$_3$ using a soxhlet apparatus. The CHCl$_3$ was concentrated in vacuo to 8.8 g (88%) of product as a white solid: mp 128°–130° C.

| Analysis calculated for C$_{14}$H$_{16}$F$_5$N$_3$O$_3$ | | | |
|---|---|---|---|
| Elemental Analysis: | C | H | N |
| Calculated | 45.53 | 4.37 | 11.38 |
| Found | 45.51 | 4.36 | 11.58 |

EXAMPLE 202

Dimethyl 2-(trifluoromethyl)-4-{[2,2,2-trifluoro-1-(methylthio)ethylidene]amino}-6-(difluoromethyl)-3,5-pyridinedicarboxylate(⅓ hydrate).

A mixture of 5 g (0.012 mol) of product of Example 211 and 2.7 g (0.013 mol) of PCl$_5$ was heated at 170° C. in an oil bath for an hour. This was cooled to 25° C., concentrated under vacuum to afford 5.2 g of dimethyl 6-(difluoromethyl)-2(trifluoromethyl)-4-[(1-chloro-2,2,2-trifluoroethylidene)amino]-3,5-pyridine dicarbolate as an oil. To a solution of 1.5 g (0.0034 mol) the above oil in 40 ml of anhydrous ether was added 0.3 g (0.0041 mol) of sodium methanethiolate. This mixture was stirred at reflux for 2 hours. The reaction mixture was then diluted with ether, washed with two 100 ml portions of water, dried (CaSO$_4$), filtered and concentrated to give 1.1 g (71%) of product as a clear oil; n$_D$≈1.4639.

| Analysis calculated for C$_{14}$H$_{10}$F$_8$N$_2$O$_4$S$_1$ | | | |
|---|---|---|---|
| Elemental Analysis | C | H | N |
| Calculated | 36.54 | 2.33 | 6.09 |
| Found | 36.53 | 2.01 | 6.08 |

EXAMPLE 203

Methyl 6-(difluoromethyl)-4-(isopropylamino)-2-(trifluoromethyl)-3-[(methylamino)thioxomethyl]-5-pyridinecarboxylate A mixture of 3 g (0.009 mol) of product of Example 201 and 7.28 g (0.018 mol) of Lawesson's reagent in 100 ml of toluene was refluxed for 16 days. The reaction mixture was cooled to 25° C., poured into H$_2$O, and extracted with ethyl acetate. The organic phase was dried (MgSO$_4$), and concentrated in vacuo to 1.4 g of a brown oil. Chromatography using 10% ethyl acetate/cyclohexane as an eluting solvent afforded 0.35 g (11%) of product as a beige solid: mp 129°–131° C.

| Analysis calculated for C$_{14}$H$_{16}$F$_5$N$_3$O$_2$S$_1$ | | | | |
|---|---|---|---|---|
| Elemental Analysis | C | H | N | S |
| Calculated | 43.63 | 4.19 | 10.90 | 8.32 |
| Found | 43.73 | 4.20 | 10.83 | 8.49 |

EXAMPLE 204

3-Ethyl 5-methyl 6-difluoromethyl)-4-hydroxy-2-(trifluoromethyl)-3,5-pyridinedicarboxylate A solution of 3.62 g (0.01 mol) of Example 103, 2.2 g (2.5 ml, 0.015 mol) of N,N-isopropylbenzylamine and 1 g (1.4 ml, 0.01 mol) of triethylamine in 40 ml of DMF was heated to 80° C. for 2 hours. Crude was poured into 3.7% HCl and extracted with Et$_2$O. The Et$_2$O layer was extracted with K$_2$CO$_3$ (aq.) and H$_2$O. Combined aqueous layers were made acidic with concentrated HCl, extracted with Et$_2$O and dried (MgSO$_4$). Solvent was removed in vacuo, affording 0.5 g of a dark brown oil. The crude was kugelrohr distilled at 100°–120° C./0.5 mm Hg° affording 0.38 g (11%) of product as a white solid; mp 38°–40°

| Analysis calculated for C$_{12}$H$_{10}$F$_5$N$_1$O$_5$ | | | |
|---|---|---|---|
| Elemental Analysis | C | H | N |
| Calculated | 41.99 | 2.94 | 4.08 |
| Found | 42.14 | 2.96 | 4.03 |

PREPARATION OF 4-HYDROXYPRIDINEDICARBOXYLATES AND COMPOUNDS DERIVED FROM ROUTE 3

The following Examples illustrate the preparation of compounds of this invention via the previously-discussed Route 3, i.e. the acetone dicarboxylate-magnesium chelate route.

EXAMPLE 205

Diethyl 2,6-bis(trifluoromethyl)-4-hydroxy-3,5-pyridinedicarboxylate ammonia salt Step A: Preparation of Diethyl 3-hydroxy-2-pentenedioate, magnesium complex dihydrate To a mechanically stirred mixture of 202 g (182 ml, 1 mol) of diethyl acetonedicarboxylate and 203 g (1 mol) of $MgCl_2 \cdot 6H_2O$ in 2 liter in $H_2O$ was added 72 g (4.2 mol) of $NH_3(g)$. A white precipitate was formed at pH 8-10. Then, the reaction mixture was stirred at 25° C. for 24 hours, the solid was filtered, washed several times with $H_2O$, then 500 ml of 0° C. methanol. The resulting solid was dried in vacuo affording 205.06 g (95%) of product as a white solid; mp 109°-111° C.

| Analysis calculated for $C_{18}H_{26}Mg_1O_{10}[2H_2O]$ | | |
|---|---|---|
| Elemental Analysis | C | H |
| Calculated | 46.72 | 6.54 |
| Found | 46.38 | 6.38 |

Step B: Preparation of diethyl 4-oxo-2,6-bis(trifluoromethyl)-4H-pyran-3,5-dicarboxylate To a 0° C. mechanically stirred mixture of 43 g (0.1 mol) of product of Step A in 50 ml of anhydrous $Et_2O$ was added dropwise 74.4 g (50 ml, 0.35 mol) of trifluoroacetic anhydride. At this point the ice-bath was removed and an additional 74.4 g (50 ml, 0.35 mol) of trifluoroacetic anhydride was added at such a rate that the reaction mixture refluxed gently. The resulting light orange solution was stirred at 25° C. for 1 hour, solvent was removed in vacuo and residue was poured slowly into a saturated solution of $NaHCO_3$ and extracted with EtOAc. The EtOAC layer was washed with $H_2O$, dried ($MgSO_4$) and concentrated in vacuo. The resulting solid was dissolved in minimum amount of $Et_2O$ and passed through silica gel using $Et_2O$ as eluting solvent. The $Et_2O$ solution was dried ($MgSO_4$), and concentrated in vacuo affording 61.63 g (82% crude yield) of product as a beige solid. For elemental analysis, a portion of this solid was recrystallized in $Et_2O$/hexane affording a white solid, mp 90°-91° C.

| Analysis calculated for $C_{13}H_{10}F_6O_6$ | | |
|---|---|---|
| Elemental Analysis | C | H |
| Calculated | 41.50 | 2.68 |
| Found | 41.40 | 2.65 |

Step C: Preparation of pyridinedicarboxylate product

To a 0° C. solution of 5 g (0.013 mol) of product of Step B in 20 ml $CH_2Cl_2$ was added 20 ml of 15% solution of $NH_4OH$ and stirred for ½ hour at 0° C. The white solid formed was filtered, washed with 30% $Et_2O$/hexane solution and dried affording 2.68 g of a solid. This solid was recrystallized in EtOAc/hexane to give 1.31 g (26%) of product as a white solid, mp 193°-195° C.

| Analysis calculated for $C_{13}H_{14}F_6N_2O_5$ | | | |
|---|---|---|---|
| Elemental Analysis | C | H | N |
| Calculated | 39.81 | 3.60 | 7.14 |
| Found | 39.76 | 3.62 | 7.11 |

EXAMPLE 206

Diethyl 2,6-bis(trifluoromethyl)-4-hydroxy-3,5-pyridinedicarboxylate

Two grams (0.005 mol) of product of Example 205 were dissolved in 2.5N NaOH and then acidified with concentrated HCl. This aqueous layer was extracted with $Et_2O$ (2X), dried ($MgSO_4$) and concentrated in vacuo affording 1.85 g. The crude was purified by kugelrohr distillation at 0.6 mm Hg and pot temperature of 90°-100° C. to give 1.65 g (88%) of product as a colorless oil: $n_D^{25}$ 1.4372.

| Analysis calculated for $C_{13}H_{11}F_6N_1O_5$ | | | |
|---|---|---|---|
| Elemental Analysis | C | H | N |
| Calculated | 41.61 | 2.95 | 3.73 |
| Found | 41.67 | 2.98 | 3.72 |

EXAMPLE 207

Diethyl 2,6-bis(pentafluoroethyl)-4-hydroxy-3,5-pyridinedicarboxylate

Step A: Preparation of diethyl 4-oxo-2,6-bis(pentafluoroethyl)-4-H-pyran-3,5-dicarboxylate This compound was prepared as described in Step B of Example 205: 21.5 g (0.05 mol) of product of Step A of Example 205 and 108.5 g (0.35 mol) of pentafluoropropionic anhydride in 100 ml of anhydrous $Et_2O$ were reacted affording 54.38 g of a yellow foamy thick oil. The crude was purified by HPLC using 7% EtOAc/cyclohexane as eluting solvent to give 9.87 g (21%) of product as a white solid: mp 49.5°-51° C.

| Analysis calculated for $C_{15}H_{10}F_{10}O_6$ | | |
|---|---|---|
| Elemental Analysis | C | H |
| Calculated | 37.83 | 2.12 |
| Found | 37.90 | 2.05 |

Step B: Preparation of pyridinedicarboxylate product

To a solution of 4.76 g (0.01 mol) of product of Step A in 50 ml of dry THF was passed 2.9 g (0.17 mol) of $NH_3$. Solvent was then reduced in vacuo, affording 5.78 g of a light yellow solid. A portion of this solid, 2.3 g, was treated with 0.7 g of $K_2CO_3$ in 20 ml of DMF for 18 hours at room temperature. The resulting mixture was poured into 10% HCl and extracted twice with $Et_2O$. The $Et_2O$ layer was washed with $H_2O$ and dried ($MgSO_4$) to give 2.12 g of a thick orange oil. The crude was purified via preparative, centrifugally-accelerated, radial thin-layer chromatography using 15% EtOAc/75% cyclohexane/10% glacial acetic acid followed by kugelrohr distillation at 80°-90° C./0.4 mm Hg affording 1.2 g (52%) of product as a colorless oil: $n_D^{25}$ 1.4139.

| Analysis calculated for $C_{15}H_{11}F_{10}N_1O_5$ | | | |
|---|---|---|---|
| Elemental Analysis | C | H | N |
| Calculated | 37.91 | 2.33 | 2.95 |
| Found | 38.21 | 2.42 | 2.78 |

EXAMPLE 208

Dimethyl 4-hydroxy-2-isopropyl-6-trifluoromethyl-3,5-pyridinedicarboxylate

Step A: Preparation of dimethyl 3-hydroxy-2-pentenedioate magnesium complex hydrate A mixture of 10 g (0.01 mol) of product of Step A of Example 205 and 50 ml of $CH_3OH$ was refluxed for 2 hours, cooled to room temperature and white solid filtered affording 6.7 g of crude material. Filtrate was recrystallized in $CH_3OH$ affording 4.46 g (58%) of product as a white solid: mp 54°–57° C.

| Analysis calculated for $C_{14}H_{18}Mg_1O_{10}[H_2O]$ | | |
|---|---|---|
| Elemental Analysis | C | H |
| Calculated | 43.38 | 5.20 |
| Found | 43.49 | 4.86 |

This compound can be prepared as described in Step A of Example 205, in 69% yield by using dimethyl acetonedicarboxylate as starting material.

Step B: Preparation of dimethyl 4-oxo-2-(trifluoromethyl)-6-(isopropyl)-4-H-pyran-3,5-dicarboxylate A mixture of 12.15 g (0.03 mol) of product of Step A in 50 ml of toluene was refluxed using a Dean-Stark trap for 1 hour. The resulting clear solution was cooled to room temperature and 50 ml of anhydrous THF were added. To this solution 6.4 g (6.3 ml, 0.06 mol) of isobutyryl chloride was added and stirred for 18 hours. Crude was poured into 3.7% HCl, extracted with EtOAc, the EtOAc layer was washed again with 3.7% HCl and saturated NaCl. Organic layer was dried (MgSO$_4$) and removed in vacuo affording 12.3 g of crude dimethyl 2-(isobutyryl)-3-oxo-1,5-pentenedioate. The crude was purified by HPLC using 10% EtOAc/cyclohexane as eluting solvent affording 8.87 g (61%) of this intermediate as a light yellow oil; $n_D^{25}$ 1.4783.

| Analysis calculated for $C_{11}H_{16}O_6$ | | |
|---|---|---|
| Elemental Analysis | C | H |
| Calculated | 54.09 | 6.60 |
| Found | 54.09 | 6.62 |

To a solution of 5 g (0.02 mol) of the above intermediate compound in 50 ml of anhydrous THF was added 13 ml (0.16 mol) of pyridine. Then the solution was cooled to 10° C. and 8.4 g (5.6 ml, 0.04 mol) of trifluoroacetic anhydride was added. During the addition an exotherm and an orange-red color was observed. The solution was then warmed to 25° C., poured into 3.7% HCl, and extracted with Et$_2$O. The Et$_2$O layer was then washed with H$_2$O and saturated NaHCO$_3$. The Et$_2$O phase was dried (MgSO$_4$) and concentrated in vacuo affording 5.29 g of crude product as an orange-yellowish solid. Product was purified by HPLC using 8% EtOAc/cyclohexane as eluting solvent affording 3.39 g (53%) of product as a yellow solid. For elemental analysis, a portion of this solid was recrystallized in hexane affording a white crystalline solid: mp 80.0°–81.5° C.

| Analysis calculated for $C_{13}H_{13}F_3O_6$ | | |
|---|---|---|
| Elemental Analysis | C | H |
| Calculated | 48.45 | 4.07 |
| Found | 48.81 | 4.14 |

This product can be prepared in one step without isolating the dimethyl 2-(isobutyryl)-3-oxo-1,5-pentenedioate in 48% overall yield.

Step C: Preparation of pyridine dicarboxylate product

To a solution of 15.59 g (0.048 mol) of product of Step B in a 1:1 solvent mixture of 120 ml of MeOH:Et$_2$O was passed 2 g (0.12 mol) of NH$_3$ gas and the reaction was stirred for 18 hours. Solvent was removed in vacuo affording 16 g of a foamy yellow solid. The crude was dissolved in 5% NaOH, washed with Et$_2$O and then the Et$_2$O was extracted with H$_2$O. The combined aqueous layers were acidified with concentrated HCl, extracted twice with Et$_2$O and the Et$_2$O layer dried (MgSO$_4$). The solvent was concentrated in vacuo affording 12.67 g of a thick amber oil. The crude was purified by HPLC using 82% cyclohexane/17% EtOAc/1% HOAc solvent mixture as eluting solvent affording 8.61 g (56%) of product as a beige solid: mp 70°–72° C.

| Analysis calculated for $C_{13}H_{14}F_3N_1O_5$ | | | |
|---|---|---|---|
| Elemental Analysis | C | H | N |
| Calculated | 48.60 | 4.39 | 4.36 |
| Found | 48.60 | 4.40 | 4.35 |

EXAMPLE 209

Dimethyl 4-isopropoxy-2-isopropyl-6-(trifluoromethyl)-3,5-pyridinedicarboxylate A mixture of 3 g (0.009 mol) of product of Example 208, 3.4 g (2 ml, 0.02 mol) of isopropyl iodide and 1.24 g (0.009 mol) of K$_2$CO$_3$ in 25 ml of DMF was stirred at 25° C. overnight. Crude was poured into H$_2$O, extracted with Et$_2$O, Et$_2$O layer was washed twice with saturated NaCl and dried (MgSO$_4$). Solvent was removed in vacuo affording 2.67 g of a light yellow oil. The crude was purified by kugelrohr distillation at 70°–85° C./0.6 mm Hg affording 2.25 g (69%) of product as a colorless oil, $n_D^{25}$ 1.4546.

| Analysis calculated for $C_{16}H_{20}F_3N_1O_5$ | | | |
|---|---|---|---|
| Elemental Analysis | C | H | N |
| Calculated | 52.89 | 5.55 | 3.89 |
| Found | 52.99 | 5.59 | 3.82 |

EXAMPLE 210

Dimethyl 4-methoxy-2-isopropyl-6-(trifluoromethyl)-3,5-pyridinedicarboxylate This compound was prepared as described in Example 209, but using CH$_3$I as the alkylating agent, affording 1.31 g (83%) of product as a colorless oil, $n_D^{25}$ 1.4571.

| Analysis calculated for $C_{14}H_{16}F_3N_1O_5$ | | | |
|---|---|---|---|
| Elemental Analysis | C | H | N |
| Calculated | 50.15 | 4.81 | 4.18 |
| Found | 50.16 | 4.84 | 4.09 |

EXAMPLE 211

Dimethyl 4-hydroxy-2-isopropyl-6-(trifluoromethyl)-3,5-pyridinedicarboxylate compound with diisopropylamine (1:1)

To a solution of 1.5 g (0.0047 mol) of Example 208 in 25 ml of anhydrous $Et_2O$ was added 0.48 g (0.66 ml, 0.0047 mol) of diisopropylamine and left stirred for 15 minutes. The white precipitate was filtered and washed with $Et_2O$ affording 1.71 g (86%) of product as a white solid; mp 148°–150° C.

| Analysis calculated for $C_{19}H_{29}F_3N_2O_5$ | | | |
|---|---|---|---|
| Elemental Analysis | C | H | N |
| Calculated | 54.02 | 6.92 | 6.63 |
| Found | 53.67 | 7.00 | 6.50 |

Using techniques similar to those described above in detail, the following compounds were prepared. These compounds are shown in Table 3, along with a physical property for each.

mol) of DBU. The reaction was warmed up to 25° C., poured into 3.7% HCl, and extracted twice with EtOAc. The EtOAc extract was washed again with 3.7% HCl, saturated NaCl and dried ($MgSO_4$). The solvent was removed in vacuo to give 25.88 g of a dark brown solid. The crude was purified by HPLC using 2% HOAc/16% EtOAc/82% cyclohexane as eluting solvent, affording 21 g (81%) of product as a beige solid. For elemental analysis a portion of this solid was washed with hexane affording the product as a white solid: mp 75°–76° C.

| Anal. Calc'd. for $C_{13}H_{14}Cl_2F_1N_1O_5 \cdot \frac{1}{4}H_2O$: | | | | |
|---|---|---|---|---|
| Elemental Analysis | C | H | N | Cl |
| Calculated | 43.53 | 4.08 | 3.91 | 19.77 |
| Found | 43.43 | 3.93 | 3.88 | 19.64 |

PRE-EMERGENT HERBICIDE EXAMPLES

As noted above, many of the compounds of this invention have been found to be effective as herbicides, usually as pre-emergent herbicides. Tables 4 and 5 summarize results of tests conducted to determine the pre-emergent herbicidal activity of the compounds of this invention.

The pre-emergent tests are conducted as follows:

Top soil is placed in aluminum pans and compacted to a depth of 0.95 to 1.27 cm from the top of the pan. On the top of the soil is placed a predetermined number of

TABLE 3

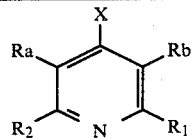

| Example | $R_1$ | $R_2$ | Ra | Rb | X | mp | $n_D^{25}$ |
|---|---|---|---|---|---|---|---|
| 212 | $CF_3$ | $CF_2H$ | $CO_2CH_3$ | $CO(NHCH_3)$ | amino | 151–153 | |
| 213 | $CF_3$ | $CF_2H$ | $CO(NHCH_3)$ | $CO(SCH_3)$ | amino | 162–164 | |
| 214 | $CH(CH_3)_2$ | $CFH_2$ | $CO_2CH_3$ | $CO_2CH_3$ | isopropoxy | | 1.4830 |
| 215 | $CF_3$ | $CF_2H$ | $CO_2CH_3$ | CO(imidazolyl) | isopropylamino | 130–133 | |
| 216 | $CF_3$ | $CF_2H$ | $CO_2CH_3$ | $CO_2CH_3$ | cyclobutylamino | 60–62 | |
| 217 | $CF_3$ | $CF_2H$ | $CO_2CH_3$ | $CO_2CH_3$ | trifluoroacetoamino | 138–139 | |
| 218 | $CF_3$ | $CF_2H$ | $CO_2CH_3$ | $CO_2CH_3$ | trifluoroacetylamino, salt with diisopropylamine (1:1) | 90–91 | |
| 219 | $CF_3CF_2$ | $CF_3CF_2$ | $CO_2CH_3$ | $CO_2CH_3$ | cyclopropylamino | 49–50 | |
| 220 | $CF_3$ | $CF_3$ | $CO_2Et$ | $CO_2Et$ | hydroxy, salt with diisopropylamine (1:1) | 99–101 | |
| 221 | $CF_3$ | $CF_2H$ | $CO_2CH_3$ | $CO_2CH_3$ | (2,2,2-trifluoro-1-propylidene)amino | | 1.4456 |
| 222 | $CF_3$ | $CF_2H$ | $CO_2CH_3$ | $CO_2Et$ | ethylthio | | 1.4676 |
| 223 | $CH(CH_3)_2$ | $CF_2H$ | $CO_2CH_3$ | $CO_2CH_3$ | isopropoxy | | 1.4725 |
| 224 | $CH(CH_3)_2$ | $CFCl_2$ | $CO_2CH_3$ | $CO_2CH_3$ | isopropoxy | 46–48 | |
| 225 | $CF_3$ | $CF_2H$ | $CO_2CH_3$ | Methylimino (methylthio) methyl | isopropylamino | | 1.5575 |
| 226 | $CF_2Cl$ | isopropyl | $CO_2CH_3$ | $CO_2CH_3$ | methoxy | 40–41 | |
| 227 | $CF_2Cl$ | isopropyl | $CO_2CH_3$ | $CO_2CH_3$ | isopropoxy | | 1.4731 |
| 228 | $CF_2Cl$ | isopropyl | $CO_2CH_3$ | $CO_2CH_3$ | ethoxy | | 1.4726 |

EXAMPLE 229

Dimethyl 2-(dichlorofluoromethyl)-4-hydroxy-6-(isopropyl)-3,5-pyridinedicarboxylate To a solution of 17.80 g (0.073 mol) of dimethyl 2-(isobutyryl)-3-oxo-1,5-pentendioate (Step B of Example 208) in 300 mL of DME at −78° C. was added 18 g (0.14 mol) of $CFCl_2CN$ followed by 11.1 g (11 ml, 0.073 seeds or vegetative propagules of various plant species. The soil required to level fill the pans after seeding or adding vegetative propagules is weighed into a pan. A known amount of the active ingredient applied in acetone as a solvent is thoroughly mixed with the soil, and the herbicide/soil mixture is used as a cover layer for prepared pans. In Table 4 below the amount of active ingredient is equal to the rate of 11.2 kg/ha. After treatment, the pans are moved into a greenhouse bench where they are watered from below as needed to give adequate moisture for germination and growth.

Approximately 10-14 days (usually 11 days) after treating, the plants are observed and the results recorded. In some instances an additional observation was made 24-28 days (usually 25 days) after treating, and these observations are denoted in the Tables by an asterisk (*) following the "Example No." column. Table 4 below summarizes such results. The herbicidal rating is obtained by means of a fixed scale based on the percent of each plant species inhibited. The ratings are defined as follows:

| % Inhibition | Rating |
| --- | --- |
| 0-24 | 0 |
| 24-49 | 1 |
| 50-74 | 2 |
| 75-100 | 3 |
| Species Not Planted | — |
| No Data, Species Planted | N |

WEED PLANT HERBICIDE ACTIVITY

The plant species usually regarded as weeds which are utilized in one set of tests, the data for which are shown in Table 4, are identified by letter headings above the columns in accordance with the following legend:

A—Canada Thistle*
B—Cocklebur
C—Velvetleaf
D—Morningglory
E—Common Lambsquarters
F—Pennsylvania Smartweed
G—Yellow Nutsedge*
H—Quackgrass*
I—Johnsongrass*
J—Downy Brome
K—Barnyardgrass.
*Grown from vegetative propagules.

TABLE 4

PRE-EMERGENCE HERBICIDE ACTIVITY FOR WEEDS

| Example No. | A | B | C | D | E | F | G | H | I | J | K |
| --- | --- | --- | --- | --- | --- | --- | --- | --- | --- | --- | --- |
| 12 | 3 | 2 | 3 | 3 | 3 | 3 | 2 | 3 | 3 | 3 | 3 |
| 13 | 3 | 3 | 3 | 3 | 3 | 3 | 3 | 3 | 3 | 3 | 3 |
| 14 | — | 0 | 0 | 0 | 0 | — | 0 | 3 | 0 | 0 | 0 |
| 14 | — | 0 | 0 | 0 | 0 | N | 0 | 0 | 0 | 0 | 0 |
| 15 | 2 | 0 | 2 | 2 | 3 | 3 | 0 | 1 | 0 | 3 | 3 |
| 16 | — | 2 | 3 | 3 | 3 | 3 | 3 | 3 | 3 | 3 | 3 |
| 16* | — | 2 | 3 | 3 | 3 | 2 | 2 | 3 | 3 | 3 | 3 |
| 17 | — | 1 | 3 | 3 | 3 | N | 2 | 3 | 3 | 3 | 3 |
| 19 | 3 | 1 | 3 | 3 | 3 | 3 | 1 | 3 | 3 | 3 | 3 |
| 20 | — | 0 | 0 | 0 | 0 | — | 0 | 0 | 0 | 0 | 0 |
| 21 | — | 0 | 3 | 3 | 3 | 3 | 0 | 3 | 2 | 3 | 3 |
| 22 | 3 | 1 | 3 | 3 | 3 | 3 | 3 | 3 | 3 | 3 | 3 |
| 23 | 3 | 3 | 3 | 3 | 3 | 3 | 3 | 3 | 3 | 3 | 3 |
| 24 | 0 | 0 | 0 | 2 | 0 | 0 | 0 | 0 | 0 | 0 | 0 |
| 25 | — | 0 | 0 | 0 | 3 | 1 | 0 | 0 | 0 | 3 | 1 |
| 31 | 3 | 0 | 1 | 3 | 3 | 3 | 0 | 1 | 0 | 3 | 3 |
| 33 | 0 | 0 | 2 | 3 | 3 | 3 | 0 | 3 | 0 | 3 | 3 |
| 34 | 0 | 0 | 0 | 0 | 3 | 3 | 0 | 0 | 0 | 0 | 1 |
| 35 | 2 | 1 | 0 | 0 | 3 | 0 | 0 | 0 | 0 | 0 | 0 |
| 36 | 0 | 0 | 0 | 0 | 0 | 0 | 0 | 0 | 0 | 0 | 0 |
| 37 | 0 | 0 | 0 | 0 | 3 | 1 | 0 | 0 | 0 | 0 | 3 |
| 38 | 1 | 0 | 3 | 3 | 3 | 3 | 1 | 3 | 0 | 3 | 3 |
| 39 | 0 | 0 | 0 | 0 | 0 | 0 | 0 | 0 | 0 | 0 | 0 |
| 40 | 0 | 0 | 0 | 0 | 3 | 0 | 0 | 0 | 0 | 0 | 0 |
| 41 | 0 | 0 | 1 | 0 | 3 | 2 | 0 | 1 | 3 | 3 | 3 |
| 42 | 0 | 0 | 1 | 0 | 3 | 1 | 0 | 0 | 0 | 3 | 3 |
| 43 | 3 | 0 | 3 | 3 | 3 | 3 | 1 | 2 | 0 | 3 | 3 |
| 44 | 0 | 0 | 0 | 0 | 0 | 0 | 0 | 0 | 0 | 0 | 1 |
| 45 | 2 | 0 | 3 | 3 | 3 | 3 | 0 | 3 | 2 | 3 | 3 |
| 46 | 0 | 0 | 2 | 3 | 3 | 3 | 0 | 2 | 0 | 3 | 3 |
| 47 | 2 | 0 | 3 | 2 | 3 | 3 | 0 | 2 | 3 | 3 | 3 |
| 48 | 0 | 0 | 0 | 0 | 2 | 0 | 0 | 0 | 0 | 0 | 3 |
| 49 | 3 | 3 | 3 | 3 | 3 | 3 | 2 | 3 | 2 | 3 | 3 |
| 50 | 0 | 0 | 0 | 0 | 2 | 0 | 0 | 0 | 0 | 0 | 3 |
| 51 | 3 | 0 | 3 | 3 | 3 | 3 | 0 | 1 | 0 | 3 | 3 |
| 52 | 3 | 3 | 3 | 3 | 3 | 3 | 2 | 2 | 0 | 3 | 3 |
| 53 | 3 | 3 | 2 | 1 | 3 | 3 | 0 | 3 | 1 | 3 | 3 |
| 54 | 3 | 1 | 3 | 3 | 3 | 3 | 3 | 3 | 3 | 3 | 3 |
| 55 | 3 | 3 | 3 | 3 | 3 | 3 | 0 | 3 | 2 | 3 | 3 |
| 56 | 3 | 3 | 3 | 3 | 3 | 3 | 2 | 3 | 3 | 3 | 3 |
| 57 | 0 | N | 3 | 3 | 3 | 3 | 0 | 1 | 0 | 3 | 3 |
| 58 | 0 | 0 | 3 | 1 | 3 | 3 | 0 | 2 | 2 | 3 | 3 |
| 59 | 0 | N | 3 | 3 | 3 | 3 | 0 | 0 | 0 | 1 | 3 |
| 60 | 3 | 2 | 3 | 3 | 3 | 3 | 2 | 3 | 3 | 3 | 3 |
| 61 | 0 | 0 | 0 | 1 | 3 | 3 | 0 | 0 | 0 | 3 | 3 |
| 62 | 3 | 1 | 3 | 3 | 3 | 3 | 1 | 3 | 1 | 3 | 3 |
| 63 | 3 | 3 | 3 | 3 | 3 | 3 | 3 | 3 | 3 | 3 | 3 |
| 64 | 0 | 0 | 3 | 1 | 3 | 3 | 0 | 0 | 0 | 2 | 3 |
| 65 | 3 | 0 | 3 | 3 | 3 | 3 | 2 | 3 | 1 | 3 | 3 |
| 66 | 3 | 3 | 3 | 3 | 3 | 3 | 3 | 3 | 3 | 3 | 3 |
| 67 | 1 | 0 | 0 | 0 | 1 | 0 | 0 | 0 | 0 | 0 | 0 |
| 68 | 0 | 0 | 0 | 0 | 1 | 0 | 0 | 0 | 0 | 0 | 1 |
| 69 | 1 | 0 | 2 | 3 | 3 | 0 | 0 | 1 | 3 | 3 | 3 |
| 70 | 1 | 0 | 3 | 3 | 3 | 3 | 3 | 3 | 3 | 3 | 3 |
| 71 | 1 | 0 | 3 | 3 | 3 | 1 | 3 | 3 | 3 | 3 | 3 |
| 72 | 1 | 0 | 3 | 3 | 3 | 1 | 3 | 2 | 3 | 3 | 3 |
| 73 | 3 | 2 | 3 | 3 | 3 | 3 | 1 | 2 | 0 | 3 | 3 |
| 74 | 3 | 0 | 3 | 3 | 3 | 3 | 2 | 3 | 3 | 3 | 3 |
| 75 | 1 | 0 | 2 | 2 | 3 | 3 | 1 | 1 | 0 | 1 | 3 |
| 76 | 3 | 3 | 3 | 3 | 3 | 3 | 3 | 3 | 3 | 3 | 3 |
| 77 | 3 | 1 | 3 | 3 | 3 | 3 | 1 | 3 | 3 | 3 | 3 |
| 78 | 0 | 0 | 2 | 2 | 3 | 2 | 0 | 0 | 3 | 0 | 3 |
| 79 | 3 | 0 | 2 | 3 | 3 | 3 | 0 | 1 | — | 3 | 3 |
| 80 | 3 | 2 | 3 | 3 | 3 | 3 | 0 | 3 | 3 | 3 | 3 |
| 81 | 3 | 0 | 3 | 3 | 3 | 3 | 0 | 3 | 0 | 3 | 3 |
| 82 | 3 | 0 | 3 | 3 | 3 | 3 | 1 | 3 | 3 | 3 | 3 |
| 83 | 3 | 2 | 3 | 3 | 3 | 3 | 3 | 3 | 3 | 3 | 3 |
| 84 | 0 | 0 | 0 | 0 | 0 | 0 | 0 | 0 | — | 2 | 0 |
| 85 | 3 | 1 | 2 | 3 | 3 | 3 | 0 | 2 | 3 | 3 | 3 |
| 86 | 0 | 0 | 0 | 0 | 0 | 0 | 0 | 0 | N | 0 | 0 |
| 87 | 3 | 0 | 3 | 3 | 3 | 3 | 1 | 3 | 3 | 3 | 3 |
| 88 | 0 | 0 | 0 | 0 | 1 | 0 | 0 | 0 | 0 | 0 | 0 |
| 89 | 3 | 0 | 3 | 3 | 3 | 3 | 0 | 3 | 3 | 3 | 3 |
| 90 | 2 | 0 | 3 | 3 | 3 | 2 | 0 | 3 | 3 | 3 | 3 |
| 91 | 2 | 1 | 3 | 3 | 3 | 3 | 0 | 3 | — | 3 | 3 |
| 92 | 0 | 0 | 2 | 2 | 3 | 2 | 0 | 3 | 3 | 3 | 3 |
| 93 | 3 | 1 | 3 | 3 | 3 | 3 | 1 | 3 | 3 | 3 | 3 |
| 94 | 3 | 0 | 0 | 1 | 3 | 3 | 0 | 0 | N | 2 | 3 |
| 95 | 0 | 1 | 2 | 0 | 3 | 3 | 0 | 0 | 3 | 2 | 3 |
| 96 | 0 | 1 | 3 | 3 | 3 | 3 | 1 | 2 | 3 | 3 | 3 |
| 97 | 1 | 0 | 0 | 0 | 1 | 0 | 0 | 0 | N | 0 | 0 |
| 98 | 0 | 1 | 1 | 2 | 3 | 2 | 0 | 0 | — | 3 | 3 |
| 99 | 0 | 0 | 0 | 0 | 0 | 0 | 0 | 0 | — | 0 | 0 |
| 100 | 3 | 3 | 2 | 3 | 3 | 2 | 1 | 0 | 0 | 1 | 3 |
| 101 | 0 | N | 0 | 0 | 1 | 0 | 0 | 0 | 0 | 0 | 0 |
| 102 | N | 0 | 1 | 0 | 2 | 3 | 0 | 0 | 0 | 1 | 3 |
| 103 | 1 | N | 0 | 0 | 0 | 0 | 0 | 0 | 0 | 0 | 0 |
| 104 | N | 0 | 0 | 0 | 1 | 1 | 0 | 0 | 0 | 2 | 2 |
| 105 | 0 | 1 | 0 | 0 | 1 | 0 | 0 | 0 | — | 0 | 0 |
| 106 | 0 | 0 | 0 | 0 | 0 | 0 | 0 | 0 | — | 1 | 1 |
| 107 | 0 | 0 | 0 | 0 | 0 | 0 | 0 | 0 | N | 0 | 1 |
| 108 | 0 | N | 1 | 0 | 0 | 0 | 0 | 0 | N | 3 | 3 |
| 109 | 3 | N | 2 | 1 | 2 | 1 | 0 | 0 | 3 | 3 | 3 |
| 110 | 0 | N | 0 | 0 | 1 | 3 | 0 | 0 | 0 | 3 | 3 |
| 111 | N | N | 1 | 0 | 2 | 3 | 0 | 0 | 0 | 3 | 3 |
| 112 | 3 | 0 | 3 | 3 | 3 | 3 | 0 | 1 | 3 | 3 | 3 |
| 113 | 1 | 0 | 3 | 3 | 3 | 3 | 0 | 1 | 3 | 3 | 3 |
| 114 | 3 | 3 | 3 | 3 | 3 | 3 | 1 | 3 | 0 | 3 | 3 |
| 115 | 3 | N | 1 | 0 | 3 | 3 | 0 | 0 | 0 | 3 | 3 |
| 116 | 3 | 3 | 3 | 3 | 3 | 3 | 1 | 3 | 3 | 3 | 3 |
| 117 | 3 | N | 3 | 3 | 3 | 3 | 1 | 2 | 0 | 3 | 3 |
| 118 | 3 | N | 3 | 3 | 3 | 3 | 1 | 3 | 3 | 3 | 3 |
| 119 | 3 | 3 | 3 | 3 | 3 | 3 | 2 | 3 | 3 | 3 | 3 |
| 120 | 2 | 0 | 1 | 1 | 1 | 0 | 0 | 0 | 0 | 0 | 3 |
| 121 | 3 | 3 | 3 | 3 | 3 | 3 | 1 | 3 | 3 | 3 | 3 |
| 122 | 3 | 0 | 3 | 3 | 3 | 3 | 1 | 3 | 3 | 3 | 3 |

TABLE 4-continued
PRE-EMERGENCE HERBICIDE ACTIVITY FOR WEEDS

| Example No. | A | B | C | D | E | F | G | H | I | J | K |
|---|---|---|---|---|---|---|---|---|---|---|---|
| 123 | 0 | 0 | 0 | 0 | 0 | 0 | 0 | 0 | 0 | 0 | 3 |
| 124 | 3 | 0 | 2 | 3 | 3 | 3 | 0 | 1 | 0 | 3 | 3 |
| 125 | 0 | 0 | 3 | 3 | 3 | 3 | 0 | 3 | 0 | 3 | 3 |
| 126 | 3 | 3 | 3 | 3 | 3 | 3 | 1 | 3 | 3 | 3 | 3 |
| 127 | 3 | 0 | 3 | 3 | 3 | 3 | 0 | 2 | 0 | 3 | 3 |
| 128 | 0 | 0 | 0 | 0 | 3 | 3 | 0 | 0 | 0 | 0 | 3 |
| 129 | 1 | 0 | 0 | 0 | 0 | 0 | 0 | 1 | 0 | 0 | 0 |
| 130 | — | 0 | 3 | 3 | 3 | 3 | 0 | 3 | 3 | 2 | 3 |
| 131 | — | 0 | 1 | 3 | N | 3 | 0 | 0 | 0 | 0 | 3 |
| 132 | — | 0 | 3 | 3 | 3 | 3 | 3 | 3 | 3 | 3 | 3 |
| 133 | — | 0 | 3 | 3 | 3 | 3 | 0 | 3 | 3 | 3 | 3 |
| 134 | — | 0 | 3 | 3 | 3 | 3 | 0 | 3 | 0 | 3 | 3 |
| 135 | — | 0 | 0 | 0 | 1 | 1 | 0 | 2 | 1 | 1 | 3 |
| 136 | — | 0 | 0 | 0 | 2 | 1 | 0 | 0 | 0 | 1 | 3 |
| 137 | 3 | 3 | 3 | 3 | 3 | 3 | 1 | 3 | 1 | 3 | 3 |
| 138 | N | 3 | 0 | 3 | 3 | 0 | 0 | 0 | 0 | 0 | 0 |
| 139 | 3 | 0 | 3 | 3 | 3 | 3 | 0 | 0 | 0 | 3 | 3 |
| 140 | — | 0 | 3 | 3 | 3 | 3 | 0 | 3 | 3 | 2 | 3 |
| 141 | — | 1 | 3 | 3 | 3 | 3 | 0 | 1 | 0 | 3 | 3 |
| 142 | — | 0 | 0 | 3 | 3 | 3 | 0 | 1 | 0 | 3 | 3 |
| 143 | — | 0 | 1 | 1 | 0 | 0 | 0 | 0 | 3 | 0 | 0 |
| 144 | 0 | 0 | 3 | 3 | 3 | 3 | 0 | 0 | 0 | 3 | 3 |
| 145 | — | 0 | 1 | 1 | N | 3 | 0 | 0 | 0 | 2 | 3 |
| 146 | — | 0 | 1 | 1 | 0 | 0 | 0 | 0 | 0 | 0 | 3 |
| 147 | — | 3 | 3 | 3 | 3 | 3 | 2 | 3 | 0 | 3 | 3 |
| 148 | — | 1 | 3 | 3 | 3 | 3 | 1 | 3 | 0 | 3 | 3 |
| 149 | — | 0 | 3 | 3 | 3 | 3 | 1 | 3 | 0 | 3 | 3 |
| 150 | — | 0 | 0 | 0 | 2 | 2 | 0 | 0 | 0 | 2 | 2 |
| 151 | — | 0 | 3 | 3 | 3 | 3 | 1 | 3 | 0 | 3 | 3 |
| 152 | — | 0 | 3 | 3 | 3 | 3 | 1 | 3 | 3 | 3 | 3 |
| 153 | — | 0 | 1 | 3 | 3 | 2 | 0 | 1 | 3 | 3 | 3 |
| 154 | — | 0 | 0 | 0 | 0 | 0 | 0 | 1 | 0 | 0 | 3 |
| 155 | — | 0 | 0 | 0 | 0 | 0 | 0 | 0 | 0 | 0 | 0 |
| 156 | — | 0 | 1 | 2 | 3 | 3 | 0 | 2 | 0 | 2 | 3 |
| 157 | — | 0 | 0 | 0 | 0 | 1 | 1 | 0 | 0 | 0 | 0 |
| 158 | — | 0 | 0 | 0 | 0 | 0 | 0 | 0 | 0 | 0 | 1 |
| 159 | — | 0 | 0 | 0 | 1 | 1 | 0 | 1 | 0 | 1 | 0 |
| 160 | — | 0 | 1 | 1 | 3 | 3 | 0 | 0 | 0 | 3 | 3 |
| 161 | — | 1 | 1 | 0 | 3 | 1 | 0 | 0 | 0 | 0 | 3 |
| 162 | — | 0 | 0 | 0 | 1 | 0 | 0 | 0 | 0 | 0 | 0 |
| 163 | — | 0 | 3 | 3 | 3 | 3 | 0 | 3 | 3 | 3 | 3 |
| 164 | — | 0 | 1 | 0 | 1 | 0 | 0 | 1 | 1 | 0 | 0 |
| 165 | 3 | 1 | 3 | 3 | 3 | 3 | 1 | 3 | 3 | 3 | 3 |
| 166 | 3 | 3 | 3 | 3 | 3 | 3 | 3 | 3 | 3 | 3 | 3 |
| 167 | 0 | 3 | 3 | 3 | 3 | 3 | 1 | 3 | 3 | 3 | 3 |
| 168 | — | 0 | 0 | 0 | N | 1 | 0 | 0 | 0 | 1 | 3 |
| 169 | 3 | 3 | 0 | 0 | 0 | 0 | 0 | 0 | 0 | 0 | 0 |
| 170 | — | 0 | 0 | 3 | N | 1 | 0 | 0 | 0 | 0 | 3 |
| 171 | — | 0 | 0 | 0 | 1 | 2 | 0 | 0 | 0 | 2 | 2 |
| 172 | 3 | 2 | 3 | 3 | 3 | 3 | 3 | 3 | 3 | 3 | 3 |
| 173 | — | 0 | 0 | 0 | 0 | 1 | 1 | 0 | 0 | 0 | 0 |
| 174 | — | 0 | 3 | 3 | 3 | 3 | 0 | 3 | 3 | 3 | 3 |
| 175 | 3 | 2 | 3 | 3 | 3 | 3 | 3 | 3 | 3 | 3 | 3 |
| 176 | 1 | 0 | 3 | 2 | 3 | 3 | 0 | 3 | 0 | 3 | 3 |
| 177 | 0 | 0 | 0 | 0 | 0 | 0 | 0 | 0 | 0 | 0 | 0 |
| 178 | 3 | 3 | 3 | 3 | 3 | 3 | 3 | 3 | 3 | 3 | 3 |
| 179 | 0 | 0 | 0 | 0 | 0 | 0 | 0 | 0 | N | 0 | 0 |
| 180 | 1 | 0 | 3 | 3 | 3 | 0 | 0 | 3 | 0 | 3 | 3 |
| 181 | 1 | 0 | 3 | 3 | 3 | 3 | 0 | 3 | 0 | 3 | 3 |
| 182 | — | 0 | 0 | 0 | 0 | 0 | 0 | 0 | 0 | 0 | 0 |
| 183 | 0 | 0 | 2 | 3 | 3 | 3 | 0 | 1 | 0 | 3 | 3 |
| 184 | 0 | 0 | 0 | 0 | 1 | 0 | 0 | 0 | 0 | 1 | 2 |
| 185 | — | 0 | 3 | 3 | 3 | 3 | 0 | 0 | 0 | 3 | 3 |
| 186 | 0 | 0 | 0 | 0 | 3 | 0 | 0 | 0 | 0 | 0 | 0 |
| 187 | 0 | 0 | 0 | 0 | 3 | 0 | 0 | 0 | 0 | 0 | 3 |
| 188 | 3 | 1 | 3 | 3 | 3 | 3 | 2 | 3 | 3 | 3 | 3 |
| 189 | 0 | 0 | 0 | 1 | 3 | 3 | 0 | 1 | 0 | 0 | 3 |
| 190 | 3 | 0 | 3 | 3 | 3 | 3 | 3 | 3 | 3 | 3 | 3 |
| 191 | 0 | 0 | 0 | 3 | 3 | 0 | 0 | 0 | 0 | 0 | 3 |
| 192 | 3 | 0 | 3 | 3 | 3 | 3 | 0 | 2 | 0 | 3 | 3 |
| 193 | 1 | 0 | 3 | 3 | 3 | 2 | 0 | 0 | 3 | 1 | 3 |
| 194 | 3 | 0 | 3 | 3 | 3 | 3 | 1 | 2 | 0 | 3 | 3 |
| 195 | 3 | 3 | 3 | 3 | 3 | 3 | 2 | 3 | 3 | 3 | 3 |
| 196 | 0 | 0 | 0 | 0 | 0 | 0 | 0 | 0 | N | 0 | 0 |
| 197 | — | 0 | 0 | 1 | 2 | 0 | 0 | 0 | 1 | 1 | 1 |
| 198 | 0 | 0 | 0 | 2 | 0 | 0 | 0 | 0 | 0 | 0 | 0 |
| 199 | 0 | 0 | 0 | 1 | 3 | 0 | 0 | 0 | N | 0 | 0 |
| 200 | 3 | 2 | 3 | 3 | 3 | 3 | 3 | 3 | 3 | 3 | 3 |
| 201 | 0 | 0 | 0 | 0 | 0 | 0 | 0 | 0 | 0 | 0 | 1 |
| 202 | 0 | 0 | 0 | 0 | 0 | 0 | 0 | 0 | 0 | 0 | 1 |
| 203 | 1 | 0 | 2 | 1 | 3 | 2 | 0 | 2 | 0 | 3 | 3 |
| 204 | 0 | 0 | 1 | N | 0 | 0 | 0 | 0 | 0 | 0 | 0 |
| 205 | 0 | 0 | 0 | 0 | 0 | 0 | 0 | 0 | 0 | 0 | 0 |
| 206 | 0 | 0 | 0 | 1 | 1 | 0 | 0 | 0 | 0 | 0 | 1 |
| 207 | 0 | 1 | 0 | 0 | 0 | 1 | 0 | 0 | — | 0 | 0 |
| 208 | 0 | 0 | 0 | 0 | 3 | 1 | 0 | 0 | 0 | 0 | 0 |
| 209 | 3 | 3 | 3 | 3 | 3 | 3 | 3 | 3 | 3 | 3 | 3 |
| 210 | 3 | 3 | 3 | 3 | 3 | 3 | 3 | 3 | 1 | 3 | 3 |
| 211 | 0 | 0 | 0 | 0 | 2 | 0 | 0 | 0 | 0 | 0 | 0 |
| 212 | 0 | 0 | 0 | 0 | N | 0 | 0 | 0 | 0 | 0 | 0 |
| 213 | 0 | 0 | 0 | 0 | 3 | 0 | 0 | 0 | 0 | 0 | 0 |
| 214 | 3 | 0 | 3 | 3 | 3 | 2 | 0 | 3 | 3 | 3 | 3 |
| 215 | 2 | 0 | 3 | 3 | 3 | 3 | 0 | 3 | 3 | 3 | 3 |
| 216 | — | 0 | 3 | 3 | 3 | 3 | 1 | 3 | 3 | 3 | 3 |
| 217 | 0 | 1 | 0 | 0 | 2 | 1 | 0 | 0 | N | 0 | 0 |
| 218 | 0 | 0 | 0 | 3 | 3 | 2 | 0 | 0 | 3 | 0 | 0 |
| 218* | 0 | 0 | 0 | 0 | 0 | 0 | 0 | 0 | 0 | 0 | 0 |
| 219 | 0 | 0 | 2 | N | 0 | 0 | 0 | 0 | 0 | 3 | 2 |
| 220 | 0 | 0 | 0 | 0 | 1 | 0 | 0 | 0 | 0 | 0 | 0 |
| 221 | 0 | 0 | 0 | 2 | 3 | 1 | 0 | 3 | 0 | 3 | 3 |
| 222 | 3 | 1 | 3 | 3 | 3 | 3 | 1 | 3 | 2 | 3 | 3 |
| 223 | 1 | 0 | 3 | 3 | 3 | 3 | 1 | 3 | 3 | 3 | 3 |
| 224 | 0 | 0 | 2 | 2 | 3 | 2 | 0 | 2 | 0 | 3 | 3 |
| 225 | 3 | 2 | 3 | 3 | 3 | 3 | 3 | 3 | 1 | 3 | 3 |
| 226 | 3 | 0 | 3 | 3 | 3 | 3 | 1 | 3 | 0 | 3 | 3 |
| 227 | 3 | 1 | 3 | 3 | 3 | 3 | 1 | 3 | 3 | 3 | 3 |
| 228 | 3 | 0 | 3 | 3 | 3 | 3 | 0 | 3 | 3 | 3 | 3 |
| 229 | 0 | 0 | 0 | 0 | 3 | 0 | 0 | 0 | 0 | 0 | 0 |

*Retest

POST-EMERGENCE HERBICIDE EXAMPLES

The post-emergence herbicidal activity of some of the various compounds of this invention was demonstrated by greenhouse testing in the following manner. Top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, except for the control pans, is removed individually to a spraying chamber and sprayed by means of an atomizer at the rated noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of 11.2 kg/ha of active ingredient. The pans were returned to the greenhouse and watered as before and the injury to the plants as compared to the control is observed at approximately 10-14 days (usually 11 days) and in some instances observed again at 24-28 (usually 25 days) after spraying.

The post-emergence herbicidal activity index used in Table 5 is as follows:

| Plant Response | Index |
|---|---|
| 0-24% Inhibition | 0 |
| 25-49% Inhibition | 1 |
| 50-74% Inhibition | 2 |
| 75-99% Inhibition | 3 |

| Plant Response | Index |
| --- | --- |
| 100% Inhibition | 4 |
| Species Not Planted | — |
| No Data | N |

The letters identifying plants used in the following tests are identical to those used for corresponding tests in the pre-emergence tests in Table 4 above.

TABLE 5

POST-EMERGENCE HERBICIDE ACTIVITY FOR WEEDS

| Example No. | A | B | C | D | E | F | G | H | I | J | K |
| --- | --- | --- | --- | --- | --- | --- | --- | --- | --- | --- | --- |
| 12 | 0 | 0 | 1 | 1 | 0 | 0 | 0 | 0 | 0 | 0 | 0 |
| 13 | 0 | 0 | 1 | 1 | 0 | 0 | 0 | 0 | 0 | 0 | 2 |
| 14 | — | 1 | 1 | 1 | 3 | — | 0 | 0 | 0 | 0 | 0 |
| 15 | 0 | 0 | 0 | 0 | 0 | 0 | 0 | 0 | 1 | 0 | 0 |
| 16 | — | 0 | 0 | 0 | 0 | 0 | 0 | 0 | 0 | 0 | 0 |
| 17 | — | 0 | 0 | 0 | 0 | — | 0 | 0 | 0 | 0 | 0 |
| 19 | 0 | 0 | 0 | 0 | 0 | 0 | 0 | 0 | 0 | 0 | 0 |
| 20 | — | 0 | 0 | 0 | 0 | 0 | 0 | 0 | 0 | 0 | 0 |
| 21 | — | 0 | 0 | 0 | 0 | 0 | 0 | 0 | 0 | 0 | 0 |
| 22 | 0 | 0 | 0 | 0 | 0 | 0 | 0 | 0 | 0 | 0 | 0 |
| 23 | 1 | 0 | 1 | 1 | 0 | 0 | 1 | 1 | 0 | 0 | 1 |
| 24 | 4 | 2 | 1 | 2 | 4 | 0 | 0 | 0 | 0 | 0 | 0 |
| 25 | — | 0 | 0 | 0 | 0 | — | 0 | 0 | 0 | 0 | 0 |
| 31 | 0 | 1 | 0 | 1 | 0 | 0 | 0 | 0 | 0 | 0 | 0 |
| 33 | 0 | 0 | 0 | 0 | 0 | 0 | 0 | 0 | 0 | 0 | 1 |
| 34 | 0 | 0 | 0 | 0 | 0 | 0 | 0 | 0 | 0 | 0 | 2 |
| 35 | 0 | 0 | 0 | 0 | 0 | 0 | 0 | 0 | 0 | 0 | 0 |
| 36 | 0 | 1 | 0 | 0 | 0 | 0 | 0 | 0 | 0 | 0 | 0 |
| 37 | 0 | 0 | 0 | 0 | 0 | 0 | 0 | 0 | 0 | 0 | 0 |
| 38 | 0 | 0 | 1 | 2 | 1 | 0 | 0 | 0 | 0 | 0 | 0 |
| 39 | 0 | 0 | 0 | 0 | 0 | 0 | 0 | 0 | 0 | 0 | 0 |
| 40 | 0 | 0 | 0 | 1 | 0 | 0 | 0 | 0 | 0 | 0 | 0 |
| 41 | 0 | 0 | 0 | 0 | 0 | 0 | 0 | 0 | 0 | 0 | 0 |
| 42 | 0 | 1 | 1 | 1 | 0 | 0 | 0 | 0 | 0 | 0 | 0 |
| 43 | 0 | 0 | 0 | 0 | 0 | 0 | 0 | 0 | 0 | 0 | 0 |
| 44 | 0 | 1 | 0 | 1 | 0 | 0 | 0 | 0 | 0 | 0 | 0 |
| 45 | 0 | 1 | 0 | 1 | N | 0 | 0 | 0 | 0 | 0 | 0 |
| 46 | 0 | 1 | 1 | 1 | 1 | 0 | 0 | 0 | 0 | 0 | 0 |
| 47 | 0 | 1 | 0 | 1 | N | 0 | 0 | 0 | 0 | 0 | 0 |
| 48 | 0 | 0 | 0 | 0 | 0 | 0 | 0 | 0 | 0 | 0 | 0 |
| 49 | 0 | 1 | 0 | 0 | 0 | 0 | 0 | 0 | 0 | 0 | 1 |
| 50 | 0 | 1 | 0 | 0 | 0 | 0 | 0 | 0 | 0 | 0 | 0 |
| 51 | 0 | 0 | 0 | 0 | 0 | 0 | 0 | 0 | 0 | 0 | 0 |
| 52 | N | 1 | 0 | 0 | 0 | 0 | 0 | 0 | 0 | 0 | 1 |
| 53 | 0 | 0 | 0 | 0 | 0 | 0 | 0 | 0 | 0 | 0 | 0 |
| 54 | 0 | 0 | 1 | 1 | 0 | 0 | 0 | 0 | 0 | 0 | 0 |
| 55 | 0 | 1 | 1 | 1 | 0 | 0 | 0 | 0 | 0 | 0 | 0 |
| 56 | 0 | 0 | 0 | 0 | 0 | 0 | 0 | N | 0 | 0 | 0 |
| 57 | 0 | 0 | 0 | 1 | N | 0 | 0 | 0 | 0 | 0 | 0 |
| 58 | N | 0 | 0 | 0 | 0 | 0 | 0 | 1 | 0 | 0 | 0 |
| 59 | 0 | 0 | 1 | 1 | 0 | N | 0 | 0 | 0 | 0 | 0 |
| 60 | 0 | 0 | 1 | 1 | N | 0 | 0 | 0 | 0 | 0 | 1 |
| 61 | 0 | N | 0 | 0 | 0 | 0 | 0 | 0 | 0 | 0 | 0 |
| 62 | 0 | 0 | 0 | 0 | N | 0 | 0 | 0 | 0 | 0 | 0 |
| 63 | 1 | 1 | 0 | 2 | 0 | 0 | 0 | 0 | 0 | 0 | 0 |
| 64 | 0 | 0 | 0 | 0 | 0 | 0 | 0 | 0 | 0 | 0 | 0 |
| 65 | 0 | 1 | 0 | 1 | N | 0 | 0 | 0 | 0 | 0 | 0 |
| 66 | 0 | 0 | 0 | 2 | 0 | 0 | 0 | 0 | 0 | 0 | 1 |
| 67 | 0 | N | 0 | 0 | 0 | 0 | 0 | 0 | 0 | 0 | 0 |
| 68 | 0 | N | 0 | 0 | 0 | 0 | 0 | 0 | 0 | 0 | 0 |
| 69 | 1 | 1 | 1 | 1 | 0 | 0 | 0 | 0 | 0 | 0 | 0 |
| 70 | 0 | 1 | 1 | 2 | 0 | 1 | 0 | 0 | 0 | 0 | 2 |
| 71 | 0 | 2 | 2 | 2 | 1 | 1 | 0 | 0 | 0 | 0 | 2 |
| 72 | 2 | 1 | 1 | 2 | 0 | 1 | 0 | 0 | 0 | 0 | 2 |
| 73 | 0 | 1 | 0 | 1 | 0 | 0 | 0 | 0 | 0 | 0 | 0 |
| 74 | 0 | 1 | 0 | 1 | 0 | 0 | 0 | 0 | 0 | 0 | 0 |
| 75 | 0 | 0 | 0 | 0 | 0 | 0 | 0 | 0 | 0 | 0 | 0 |
| 76 | 0 | 1 | 0 | 2 | 0 | 0 | 0 | 0 | 0 | 0 | 0 |
| 77 | 0 | 2 | 1 | 2 | N | 0 | 0 | 0 | 1 | 0 | 0 |
| 78 | 0 | 0 | 0 | 0 | 0 | 0 | 0 | 0 | 0 | 0 | 0 |
| 79 | 0 | 0 | 0 | 0 | 0 | 0 | 0 | 0 | — | 0 | 0 |
| 80 | 0 | 1 | 1 | 0 | 0 | 0 | 0 | 0 | 0 | 0 | 0 |
| 81 | 0 | 0 | 0 | 0 | 0 | 0 | 0 | 0 | 0 | 0 | 0 |
| 82 | 0 | 0 | 0 | 0 | 0 | 0 | 0 | 0 | 0 | 0 | 0 |
| 83 | 0 | 0 | 0 | 0 | 0 | 0 | 0 | 0 | 0 | 0 | 0 |
| 84 | 0 | 0 | 0 | 0 | 0 | 0 | 0 | 0 | 0 | 0 | 0 |
| 85 | 0 | 0 | 1 | 1 | 0 | 0 | 0 | 0 | 0 | 0 | 0 |
| 86 | 0 | 0 | 0 | 0 | 0 | 0 | 0 | 0 | 0 | 0 | 0 |
| 87 | 0 | 0 | 0 | 0 | 0 | 0 | 0 | 0 | 0 | 0 | 0 |
| 88 | 0 | 0 | 0 | 0 | 0 | 0 | 0 | 0 | 0 | 0 | 0 |
| 89 | 1 | 1 | 0 | 1 | 0 | 0 | 0 | 0 | 0 | 0 | 0 |
| 90 | 0 | 0 | 0 | 0 | 0 | 0 | 0 | 0 | 0 | 0 | 0 |
| 91 | 0 | 0 | 1 | 1 | 1 | 0 | 0 | 0 | — | 0 | 1 |
| 92 | 0 | 0 | 0 | 0 | 0 | 0 | 0 | 0 | 0 | 0 | 0 |
| 93 | 0 | 0 | 0 | 0 | 0 | 0 | 0 | 0 | 0 | 0 | 0 |
| 94 | 0 | 0 | 0 | 1 | 0 | 0 | 0 | 0 | 0 | 0 | 0 |
| 95 | 0 | 0 | 0 | 0 | 0 | 0 | 0 | 0 | 0 | 0 | 0 |
| 96 | 0 | 1 | 0 | 1 | 0 | 0 | 0 | 1 | N | 0 | 0 |
| 97 | N | 1 | 0 | 0 | 1 | 0 | 0 | 0 | N | 0 | 0 |
| 98 | 0 | 0 | 0 | 0 | 0 | 0 | 0 | 0 | — | 0 | 0 |
| 99 | 0 | 0 | 0 | 0 | 0 | 0 | 0 | 0 | — | 0 | 0 |
| 100 | 0 | 0 | 1 | 1 | 1 | 0 | 0 | 0 | 0 | 0 | 0 |
| 101 | 0 | 0 | 1 | 1 | 1 | 0 | 0 | 0 | 0 | 0 | 0 |
| 102 | 0 | N | 0 | 0 | 0 | 0 | 0 | 0 | 0 | 0 | 0 |
| 103 | 0 | N | 0 | 0 | 0 | 0 | 0 | 0 | 0 | 0 | 0 |
| 104 | 0 | N | 0 | 0 | 0 | 0 | 0 | 0 | 0 | 0 | 0 |
| 105 | 0 | 0 | 0 | 0 | 0 | 0 | 0 | 0 | — | 0 | 0 |
| 106 | 0 | 0 | 0 | 0 | 0 | 0 | 0 | 0 | — | 0 | 0 |
| 107 | N | 0 | 0 | 1 | 0 | 0 | 0 | 0 | 0 | 0 | 2 |
| 108 | 0 | 0 | 0 | 0 | 0 | 0 | 0 | 0 | 0 | 0 | 0 |
| 109 | 0 | 0 | 0 | 0 | 0 | 0 | 0 | 0 | 0 | 0 | 0 |
| 110 | 0 | 0 | 0 | 0 | 0 | 0 | 0 | 0 | N | 0 | 0 |
| 111 | 0 | 0 | 0 | 0 | 0 | 0 | 0 | 0 | N | 0 | 0 |
| 112 | N | 0 | 0 | 0 | 0 | 0 | 0 | 0 | N | 0 | 0 |
| 113 | 0 | 1 | 1 | 0 | 0 | 0 | 0 | 0 | 0 | 0 | 0 |
| 114 | N | 0 | 1 | 0 | 0 | 0 | 0 | 0 | 0 | 0 | 0 |
| 115 | 0 | 0 | 0 | 0 | 0 | 0 | 0 | 0 | N | 0 | 1 |
| 116 | 0 | N | 1 | 1 | 0 | 0 | 0 | 0 | 0 | 0 | 1 |
| 117 | 0 | N | 0 | 0 | 0 | 0 | 0 | 0 | 0 | 0 | 0 |
| 118 | 0 | 0 | 0 | 0 | 0 | 0 | 0 | 0 | N | 0 | 0 |
| 119 | N | N | 1 | 1 | 1 | 0 | 0 | 0 | 0 | 0 | 0 |
| 120 | N | 0 | 0 | 1 | 0 | 0 | 0 | 0 | 0 | 0 | 0 |
| 121 | 0 | 0 | 1 | 1 | 0 | 0 | 0 | 0 | 0 | 0 | 1 |
| 122 | 0 | 1 | 1 | 2 | 1 | 0 | 0 | 1 | N | 0 | 1 |
| 123 | N | 0 | 0 | 0 | 0 | 0 | 0 | 0 | 0 | 0 | 0 |
| 124 | 0 | 1 | 0 | 0 | 0 | 0 | 0 | 0 | 0 | 0 | 0 |
| 125 | N | 1 | 1 | 1 | 0 | 0 | 0 | 0 | 0 | 0 | 0 |
| 126 | N | 0 | 1 | 0 | 0 | 0 | 0 | 0 | 0 | 0 | 0 |
| 127 | 0 | N | 0 | 1 | 0 | 0 | 0 | 0 | 0 | 0 | 0 |
| 128 | N | 0 | 1 | 1 | 0 | 0 | 0 | 0 | 0 | 0 | 0 |
| 129 | 0 | 0 | 0 | 0 | 0 | 0 | 0 | 0 | 0 | 0 | 0 |
| 130 | — | 1 | 2 | 1 | 0 | 0 | 0 | 0 | 0 | 0 | 0 |
| 131 | — | 0 | 0 | 0 | 0 | 0 | 0 | 0 | 0 | 0 | 0 |
| 132 | — | 2 | 1 | 1 | N | 0 | 0 | 0 | 0 | 1 | 0 |
| 133 | — | 0 | 1 | 1 | 0 | 0 | 0 | 0 | 0 | 0 | 0 |
| 134 | — | 1 | 1 | 1 | 0 | 0 | 0 | 0 | 0 | 0 | 0 |
| 135 | — | N | 0 | 0 | 1 | 0 | 0 | 0 | 0 | 0 | 0 |
| 136 | — | 0 | 0 | 0 | 0 | 0 | 0 | 0 | 0 | 0 | 0 |
| 137 | 1 | 0 | 1 | 2 | 1 | 0 | 0 | 0 | 0 | 0 | 0 |
| 138 | 0 | 0 | 0 | 2 | N | 1 | 0 | 0 | 0 | 1 | 0 |
| 139 | 0 | N | 0 | 2 | 1 | 0 | 0 | 0 | 1 | 0 | 0 |
| 140 | 0 | 0 | 0 | 1 | 0 | 0 | 0 | 0 | 0 | 0 | 0 |
| 141 | 0 | 0 | 0 | 0 | 0 | 0 | 0 | 0 | 0 | 0 | 0 |
| 142 | — | 1 | 1 | 0 | 0 | 0 | 0 | 0 | 0 | 0 | 0 |
| 143 | — | 0 | 0 | 0 | 0 | 0 | 0 | 0 | 0 | 0 | 0 |
| 144 | 0 | 0 | 1 | 1 | 1 | 0 | 0 | 0 | 0 | 0 | 0 |
| 145 | — | 0 | 1 | 1 | 0 | 0 | 0 | 0 | 0 | 0 | 0 |
| 146 | — | 0 | 0 | 0 | 0 | 0 | 0 | 0 | 0 | 0 | 0 |
| 147 | — | 0 | 1 | 1 | 0 | 0 | 0 | 0 | 0 | 0 | 0 |
| 148 | — | 0 | 0 | 0 | 0 | 0 | 0 | 0 | 0 | 0 | 0 |
| 149 | — | 0 | 0 | 0 | 0 | 0 | 0 | 0 | 0 | 0 | 0 |
| 150 | — | 0 | 0 | 0 | 0 | 0 | 0 | 0 | 0 | 0 | 0 |
| 151 | — | 0 | 0 | 0 | 0 | 0 | 0 | 0 | 0 | 0 | 0 |
| 152 | — | 0 | 0 | 0 | 0 | 0 | 0 | 0 | 0 | 0 | 0 |
| 153 | — | 0 | 0 | 0 | 0 | 0 | 0 | 0 | 0 | 0 | 0 |
| 154 | — | 0 | 0 | 0 | 0 | 0 | 0 | 0 | 0 | 0 | 0 |
| 155 | — | 0 | 0 | 0 | 0 | 0 | 0 | 0 | 0 | 0 | 0 |
| 156 | — | 0 | 0 | 0 | 0 | 0 | 0 | 0 | 0 | 0 | 0 |
| 157 | — | 0 | 0 | 0 | 0 | 0 | 0 | 0 | 0 | 0 | 0 |
| 158 | — | 0 | 0 | 0 | 0 | 0 | 0 | 0 | 0 | 0 | 0 |
| 159 | — | 0 | 0 | 0 | 0 | 0 | 0 | 0 | 0 | 0 | 0 |
| 160 | — | 0 | 0 | 0 | 0 | 0 | 0 | 0 | 0 | 0 | 0 |
| 161 | — | 0 | 0 | 0 | 0 | 0 | 0 | 0 | 0 | 0 | 0 |
| 162 | — | 0 | 1 | 0 | 0 | 0 | 0 | 0 | 0 | 0 | 0 |

TABLE 5-continued

POST-EMERGENCE HERBICIDE ACTIVITY FOR WEEDS

| Example No. | A | B | C | D | E | F | G | H | I | J | K |
|---|---|---|---|---|---|---|---|---|---|---|---|
| 163 | — | 0 | 0 | 0 | 0 | 0 | 0 | 0 | 0 | 0 | 0 |
| 164 | — | 0 | 0 | 0 | 0 | 0 | 0 | 0 | 0 | 0 | 0 |
| 165 | N | 0 | 1 | 1 | 1 | 0 | 0 | 0 | 0 | 0 | 0 |
| 166 | N | 0 | 0 | 0 | 0 | 0 | 0 | 0 | 0 | 0 | 0 |
| 167 | N | 0 | 0 | 0 | 0 | 0 | 0 | 0 | 0 | 0 | 0 |
| 168 | — | 0 | 0 | 0 | 0 | 0 | 0 | 0 | 0 | 0 | 0 |
| 169 | 3 | 3 | 0 | 0 | 0 | 0 | 0 | 0 | 0 | 0 | 0 |
| 169* | 0 | 0 | 0 | 0 | 0 | 0 | 0 | 0 | 0 | 0 | 0 |
| 170 | — | 0 | 0 | 0 | 0 | 0 | 0 | 0 | 0 | 0 | 0 |
| 171 | — | 0 | 0 | 0 | 0 | 0 | 0 | 0 | 0 | 2 | 0 |
| 172 | 0 | N | 1 | 1 | 0 | 0 | 0 | 0 | 0 | 0 | 0 |
| 173 | 0 | 0 | 0 | 0 | 0 | 0 | 0 | 0 | 0 | 0 | 0 |
| 174 | — | 0 | 0 | 0 | 0 | 0 | 0 | 0 | 0 | 0 | 0 |
| 175 | 0 | 1 | 2 | 1 | 1 | 0 | 0 | 0 | 0 | 0 | 0 |
| 176 | 0 | 0 | 0 | 0 | N | 0 | 0 | 0 | 0 | 0 | 0 |
| 177 | 0 | 0 | 0 | 0 | N | 0 | 0 | 0 | 0 | 0 | 0 |
| 178 | — | 1 | 1 | N | 0 | 0 | 0 | 0 | 0 | 0 | 1 |
| 179 | 0 | 0 | 0 | 0 | 0 | 0 | 0 | 0 | 0 | 0 | 0 |
| 180 | 1 | 1 | 1 | 1 | 1 | 0 | 0 | 0 | N | 0 | 0 |
| 181 | 0 | 0 | 0 | 0 | 3 | 0 | 0 | 0 | 0 | 0 | 0 |
| 182 | — | 0 | 0 | 0 | 0 | 0 | 0 | 0 | 1 | 0 | 0 |
| 183 | 0 | 1 | 1 | 1 | 0 | 0 | 0 | 0 | 0 | 0 | 0 |
| 184 | N | 0 | 0 | 0 | N | 0 | 0 | 0 | 0 | 0 | 0 |
| 185 | — | 0 | 1 | 0 | 0 | 0 | 0 | 0 | 0 | 0 | 0 |
| 186 | 0 | 0 | 0 | 0 | 0 | 0 | 0 | 0 | 0 | 0 | 0 |
| 187 | 0 | 0 | 0 | 0 | 0 | 0 | 0 | 0 | 0 | 0 | 0 |
| 188 | 1 | 1 | 1 | 1 | 0 | 0 | 0 | 0 | 0 | 0 | 1 |
| 189 | 0 | 0 | 0 | 0 | 2 | 0 | 0 | 0 | 0 | 0 | 0 |
| 190 | 0 | 0 | 0 | 0 | 1 | 0 | 0 | 0 | 0 | 0 | 1 |
| 191 | 0 | 0 | 1 | 1 | 0 | 0 | 0 | 0 | 0 | 0 | 0 |
| 192 | 0 | 0 | 1 | 0 | 0 | 0 | 0 | 0 | 0 | 0 | 0 |
| 193 | 0 | 0 | 0 | 0 | 0 | 0 | 0 | 0 | 0 | 0 | 0 |
| 194 | 0 | 1 | 0 | 1 | 1 | 0 | 0 | 0 | 0 | 0 | 0 |
| 195 | 0 | 1 | 0 | 1 | 1 | 0 | 0 | 0 | 0 | 0 | 1 |
| 196 | 0 | 0 | 0 | 0 | 0 | 0 | 0 | 0 | 0 | 0 | 0 |
| 197 | — | 1 | 0 | 1 | 0 | 0 | 0 | 0 | 0 | 0 | 0 |
| 198 | 4 | 2 | 1 | 2 | 4 | 0 | 0 | 0 | 0 | 0 | 0 |
| 199 | 0 | 0 | 0 | 0 | 0 | 0 | 0 | 0 | 0 | 0 | 0 |
| 200 | 0 | 0 | 1 | 0 | 0 | 0 | 0 | 0 | 0 | 0 | 0 |
| 201 | 0 | 0 | 0 | 0 | N | 0 | 0 | 0 | 0 | 0 | 0 |
| 202 | 0 | 0 | 0 | 0 | 0 | 0 | 0 | 0 | 0 | 0 | 0 |
| 203 | 0 | 0 | 0 | 0 | 0 | 0 | 0 | 0 | 0 | 0 | 0 |
| 204 | 0 | 0 | 0 | 0 | 0 | 0 | 0 | 0 | 0 | 0 | 0 |
| 205 | 0 | 0 | 0 | 0 | 0 | 0 | 0 | 0 | 0 | 0 | 0 |
| 206 | 0 | 1 | 0 | 0 | 0 | 0 | 0 | 0 | 0 | 0 | 0 |
| 207 | N | 0 | 0 | 0 | 0 | 0 | 0 | 0 | 0 | 0 | 0 |
| 208 | 0 | 1 | 0 | 0 | 3 | 1 | 0 | 0 | 0 | 0 | 1 |
| 209 | 0 | 1 | 1 | 1 | 0 | 0 | 0 | 0 | 0 | 0 | 2 |
| 210 | 0 | 0 | 1 | 1 | 0 | 0 | 0 | 0 | 0 | 0 | 1 |
| 211 | 0 | 0 | 0 | 0 | 3 | 0 | 0 | 0 | 0 | 0 | 0 |
| 212 | 0 | 0 | 0 | 0 | 0 | 0 | 0 | 0 | 0 | 0 | 0 |
| 213 | N | 0 | 0 | 0 | 0 | 0 | 0 | 0 | 0 | 0 | 0 |
| 214 | 0 | 0 | 0 | 0 | 0 | 0 | 0 | 0 | — | 0 | 0 |
| 215 | 0 | 1 | 0 | 0 | 0 | 0 | 0 | 0 | 0 | 0 | 0 |
| 216 | — | 0 | 1 | 1 | 1 | 0 | 0 | 0 | 0 | 1 | 0 |
| 217 | 0 | 0 | 0 | 0 | 0 | 0 | 0 | 0 | 0 | 0 | 0 |
| 218 | 0 | 1 | 1 | 0 | 0 | 0 | 0 | 0 | 0 | 0 | 0 |
| 219 | 0 | 0 | 0 | 0 | N | 0 | 0 | 0 | 0 | 0 | 0 |
| 220 | 0 | 1 | 0 | 1 | 3 | 0 | 0 | 0 | 0 | 0 | 0 |
| 221 | 0 | 0 | 0 | 0 | 0 | 0 | 0 | 0 | 0 | 0 | 0 |
| 222 | 0 | 3 | 0 | 2 | 3 | 1 | 1 | 0 | 1 | 0 | 2 |
| 223 | 0 | 0 | 0 | 0 | 0 | 0 | 0 | 0 | — | 0 | 0 |
| 224 | 0 | 0 | 0 | 0 | 0 | 0 | 0 | 0 | 0 | 0 | 0 |
| 225 | 0 | 0 | 1 | 0 | 0 | 0 | 0 | 0 | 0 | 0 | 1 |
| 226 | 1 | 0 | 0 | 1 | 0 | 0 | 0 | 0 | 0 | 0 | 1 |
| 227 | 0 | 0 | 0 | 0 | 0 | 0 | 0 | 0 | 0 | 0 | 0 |
| 228 | 0 | 0 | 0 | 1 | 0 | 0 | 0 | 0 | 0 | 0 | 0 |
| 229 | 0 | 1 | 0 | 0 | 4 | 0 | 0 | 0 | 0 | 0 | 1 |

*Retest

The compounds of this invention were further tested at the application rates shown in the following Table 6 by utilizing the above planting or spraying procedures on the following plant species, which include several useful crop plants to determine the relative preemergence herbicidal activity to plants usually regarded as crops relative to those usually regarded as weeds:

L—Soybean
M—Sugarbeet
N—Wheat
O—Rice
P—Sorghum
B—Cocklebur
Q—Wild Buckwheat
D—Morningglory
R—Hemp Sesbania
E—Common Lambsquarters
F—Pennsylvania Smartweed
C—Velvetleaf
J—Downy Brome
S—Panicum spp.
K—Barnyardgrass
T—Large Crabgrass.

The results are summarized in Table 6.
The asterisk (*) denotes a retest.

TABLE 6

PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 12 | 5.6 | 3 | 3 | 3 | 3 | 3 | 3 | 3 | 3 | 3 | 3 | 3 | 3 | 3 | 3 | 3 | 3 |
|  | 1.12 | 0 | 3 | 3 | 3 | 3 | 0 | 3 | 2 | 1 | 3 | 2 | 1 | 3 | 3 | 3 | 3 |
|  | 0.28 | 0 | 1 | 0 | 0 | 3 | 0 | 0 | 0 | 0 | 0 | 0 | 0 | 2 | 2 | 3 | 3 |
|  | 0.056 | 0 | 0 | 0 | 0 | 0 | 0 | 0 | 0 | 0 | 0 | 0 | 0 | 0 | 0 | 0 | 0 |
| 13 | 5.6 | 3 | 3 | 3 | 3 | 3 | 1 | 3 | 3 | 3 | 3 | 3 | 3 | 3 | 3 | 3 | 3 |
|  | 1.12 | 2 | 3 | 3 | 3 | 3 | 0 | 3 | 3 | 3 | 3 | 3 | 3 | 3 | 3 | 3 | 3 |
|  | 0.28 | 0 | 3 | 3 | 3 | 3 | 0 | 3 | 1 | 2 | 3 | 3 | 2 | 3 | 3 | 3 | 3 |
|  | 0.056 | 0 | 2 | 0 | 1 | 3 | 0 | 0 | 0 | 0 | 2 | 1 | 1 | 1 | 1 | 3 | 3 |
|  | 0.0112 | 0 | 0 | 0 | 0 | 0 | 0 | 0 | 0 | 0 | 0 | 0 | 0 | 0 | 0 | 0 | 0 |
| 15 | 5.6 | 1 | 3 | 1 | 3 | 1 | 0 | 2 | 1 | 2 | 3 | 3 | 1 | 2 | 3 | 3 | 3 |
|  | 1.12 | 0 | 1 | 1 | 2 | 0 | 0 | 0 | 0 | 1 | 1 | 1 | 0 | 0 | 0 | 1 | 2 |
|  | 0.28 | 0 | 1 | 0 | 0 | 0 | 0 | 0 | 0 | 0 | 0 | 1 | 0 | 0 | 0 | 0 | 0 |
|  | 0.056 | 0 | 1 | 0 | 0 | 0 | 0 | 0 | 0 | 0 | 3 | 1 | 0 | 0 | 0 | 0 | 2 |
| 16 | 5.6 | 3 | 3 | 3 | 3 | 3 | 1 | 3 | 3 | 3 | 3 | 3 | 3 | 3 | 3 | 3 | 3 |
|  | 1.12 | 1 | 3 | 3 | 3 | 3 | 0 | 2 | 2 | 1 | 3 | 2 | 1 | 3 | 3 | 3 | 3 |
|  | 0.28 | 0 | 1 | 0 | 0 | 0 | 0 | 0 | 0 | 0 | 0 | 0 | 0 | 0 | 0 | 1 | 2 |
|  | 0.056 | 0 | 0 | 0 | 0 | 0 | 0 | 0 | 0 | 0 | 0 | 0 | 0 | 0 | 0 | 0 | 0 |
| 17 | 5.6 | 3 | 3 | 3 | 3 | 3 | 2 | 2 | 1 | 2 | 3 | 2 | 2 | 3 | 3 | 3 | 3 |
|  | 1.12 | 0 | 2 | 3 | 1 | 3 | 0 | 1 | 0 | 1 | 2 | 1 | 0 | 3 | 3 | 3 | 3 |
|  | 0.28 | 0 | 0 | 0 | 0 | 0 | 0 | 0 | 0 | 0 | 0 | 0 | 0 | 1 | 0 | 1 | 1 |
|  | 0.056 | 0 | 0 | 0 | 0 | 0 | 0 | 0 | 0 | 0 | 0 | 0 | 0 | 0 | 0 | 0 | 0 |
|  | 0.0112 | 0 | 0 | 0 | 0 | 0 | 0 | 0 | 0 | 0 | 0 | 0 | 0 | 0 | 0 | 0 | 0 |

TABLE 6-continued
PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 19 | 5.6 | 1 | 3 | 3 | 3 | 3 | 1 | 3 | 3 | 2 | 3 | 3 | 1 | 3 | 3 | 3 | 3 |
|  | 1.12 | 1 | 3 | 3 | 1 | 2 | 1 | 3 | 1 | 2 | 2 | 2 | 1 | 2 | 3 | 3 | 3 |
|  | 0.28 | 0 | 2 | 1 | 0 | 0 | 0 | 1 | 0 | 2 | 2 | 1 | 1 | 1 | 1 | 2 | 2 |
|  | 0.056 | 0 | 0 | 0 | 0 | 0 | 0 | 0 | 0 | 0 | 0 | 0 | 0 | 0 | 0 | 0 | 0 |
| 21 | 5.6 | 2 | 3 | 3 | 3 | 3 | 1 | 2 | 3. | 2 | 3 | 3 | 0 | 3 | 3 | 3 | 3 |
|  | 1.12 | 1 | 1 | 2 | 1 | 0 | 0 | 0 | 0 | 1 | 2 | 1 | 0 | 0 | 2 | 3 | 3 |
|  | 0.28 | 0 | 1 | 0 | 0 | 0 | 0 | 0 | 0 | 0 | 0 | 0 | 0 | 0 | 0 | 2 | 1 |
|  | 0.056 | 0 | 0 | 0 | 0 | 0 | 0 | 0 | 0 | 0 | 0 | 0 | 0 | 0 | 0 | 0 | 0 |
| 22 | 5.6 | 3 | 3 | 3 | 3 | 3 | 3 | 3 | 3 | 3 | 3 | 3 | 3 | 3 | 3 | 3 | 3 |
|  | 1.12 | 1 | 3 | 3 | 3 | 3 | 0 | 3 | 0 | 1 | 3 | 2 | 1 | 3 | 3 | 3 | 3 |
|  | 0.28 | 1 | 2 | 1 | 1 | 0 | 0 | 2 | 1 | 1 | 2 | 2 | 1 | 1 | 1 | 1 | 3 |
|  | 0.056 | 0 | 0 | 0 | 0 | 0 | 0 | 0 | 0 | 0 | 0 | 0 | 0 | 0 | 0 | 0 | 0 |
| 23 | 5.6 | 3 | 3 | 3 | 3 | 3 | 0 | 3 | 3 | 3 | 3 | 3 | 3 | 3 | 3 | 3 | 3 |
|  | 1.12 | 3 | 3 | 3 | 3 | 3 | 0 | 3 | 3 | 3 | 3 | 3 | 3 | 3 | 3 | 3 | 3 |
|  | 0.28 | 1 | 2 | 3 | 3 | 3 | 0 | 2 | 2 | 2 | 3 | 3 | 2 | 3 | 3 | 3 | 3 |
|  | 0.056 | 0 | 1 | 0 | 0 | 3 | 0 | 0 | 0 | 0 | 0 | 0 | 0 | 1 | 2 | 3 | 2 |
|  | 0.0112 | 0 | 0 | 0 | 0 | 0 | 0 | 0 | 0 | 0 | 0 | 0 | 0 | 0 | 0 | 0 | 0 |
| 25 | 5.6 | 0 | 1 | 0 | 0 | 0 | 0 | 0 | 0 | 0 | 1 | 0 | 0 | 0 | 0 | 1 | 1 |
|  | 1.12 | 0 | 0 | 0 | 0 | 0 | 0 | 0 | 0 | 0 | 0 | 0 | 0 | 0 | 0 | 0 | 0 |
| 31 | 5.6 | 0 | 2 | 3 | 1 | 3 | 0 | 2 | 1 | 2 | 2 | 2 | 2 | 3 | 3 | 3 | 3 |
|  | 1.12 | 0 | 1 | 0 | 0 | 0 | 0 | 0 | 0 | 0 | 0 | 0 | 1 | 0 | 2 | 2 | 2 |
|  | 0.28 | 0 | 0 | 0 | 0 | 0 | 0 | 0 | 0 | 0 | 0 | 0 | 0 | 0 | 0 | 0 | 0 |
| 33 | 5.6 | 2 | 3 | 3 | 3 | 3 | 1 | 3 | 3 | 3 | 3 | 3 | 0 | 3 | 3 | 3 | 3 |
|  | 1.12 | 0 | 1 | 0 | 2 | 2 | 0 | 0 | 0 | 0 | 2 | 2 | 1 | 3 | 3 | 3 | 3 |
|  | 0.28 | 0 | 0 | 0 | 0 | 0 | 0 | 0 | 0 | 0 | 0 | 0 | 0 | 0 | 0 | 0 | 0 |
| 34 | 5.6 | 0 | 0 | 0 | 0 | 0 | 0 | 0 | 0 | 0 | 0 | 0 | 0 | 0 | 0 | 0 | 0 |
|  | 1.12 | 0 | 0 | 0 | 0 | 0 | N | 0 | 0 | 0 | 0 | 0 | 0 | 0 | 0 | 0 | 0 |
| 37 | 5.6 | 0 | 0 | 0 | 0 | 0 | 0 | 0 | 0 | 0 | 0 | 0 | 0 | 0 | 0 | 0 | 0 |
|  | 1.12 | 0 | 0 | 0 | 0 | 0 | 0 | 0 | 0 | 0 | 0 | 0 | 0 | 0 | 0 | 0 | 0 |
| 38 | 5.6 | 0 | 3 | 3 | 2 | 3 | 0 | 3 | 1 | 3 | 3 | 3 | 2 | 3 | 3 | 3 | 3 |
|  | 1.12 | 0 | 2 | 0 | 1 | 3 | 0 | 2 | 0 | 1 | 3 | 2 | 1 | 3 | 3 | 3 | 3 |
|  | 0.28 | 0 | 1 | 0 | 0 | 0 | 0 | 0 | 0 | 0 | 1 | 0 | 0 | 0 | 1 | 2 | 2 |
| 41 | 5.6 | 0 | 1 | 1 | 1 | 2 | 0 | 2 | 2 | 1 | 3 | 2 | 1 | 3 | 3 | 3 | 3 |
|  | 1.12 | 0 | 0 | 0 | 0 | 0 | 0 | 0 | 0 | 0 | 0 | 0 | 0 | 2 | 0 | 0 | 2 |
|  | 0.28 | 0 | 0 | 0 | 0 | 0 | 0 | 0 | 0 | 0 | 0 | 0 | 0 | 0 | 0 | 0 | 0 |
| 42 | 5.6 | 0 | 0 | 0 | 1 | 2 | 1 | 1 | 1 | 2 | 3 | 2 | 1 | 1 | 1 | 2 | 3 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 43 | 5.6 | 1 | 3 | 3 | 3 | 3 | 1 | 3 | 3 | 3 | 3 | 3 | 2 | 3 | 3 | 3 | 3 |
|  | 1.12 | 0 | 3 | 3 | 1 | 3 | 0 | 2 | 2 | 2 | 3 | 3 | 2 | 3 | 3 | 3 | 3 |
|  | 0.28 | 0 | 0 | 0 | 0 | 2 | 0 | 0 | 0 | 0 | 0 | 0 | 1 | 2 | 2 | 1 | 1 |
|  | 0.056 | 0 | 0 | 0 | 0 | 0 | 0 | 0 | 0 | 0 | 0 | 0 | 0 | 0 | 0 | 0 | 0 |
| 45 | 5.6 | 2 | 3 | 3 | 3 | 3 | 0 | 3 | 3 | 3 | 3 | 3 | 3 | 3 | 3 | 3 | 3 |
|  | 1.12 | 0 | 3 | 1 | 1 | 3 | 0 | 2 | 2 | 2 | 3 | 3 | 2 | 3 | 3 | 3 | 3 |
|  | 0.28 | 0 | 0 | 0 | 0 | 0 | 0 | 0 | 0 | 0 | 0 | 0 | 0 | 0 | 0 | 1 | 1 |
|  | 0.056 | 0 | 0 | 0 | 0 | 0 | 0 | 0 | 0 | 0 | 0 | 0 | 0 | 0 | 0 | 0 | 0 |
| 46 | 5.6 | 3 | 3 | 1 | 3 | 3 | 0 | 3 | 3 | 2 | 3 | 3 | 1 | 3 | 3 | 3 | 3 |
|  | 1.12 | 0 | 3 | 1 | 0 | 0 | 0 | 0 | 0 | 0 | 2 | 1 | 0 | 3 | 3 | 3 | 3 |
|  | 0.28 | 0 | 2 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 47 | 5.6 | 0 | 3 | 3 | 3 | 3 | 0 | 3 | 3 | 3 | 3 | 3 | 2 | 3 | 3 | 3 | 3 |
|  | 1.12 | 0 | 2 | 0 | 0 | 3 | 0 | 2 | 0 | 0 | 1 | 0 | 0 | 3 | 3 | 3 | 3 |
|  | 0.28 | 0 | 0 | 0 | 0 | 0 | 0 | 0 | 0 | 0 | 0 | 0 | 0 | 0 | 0 | 0 | 2 |
|  | 0.056 | 0 | 0 | 0 | 0 | 0 | 0 | 0 | 0 | 0 | 0 | 0 | 0 | 0 | 0 | 0 | 0 |
| 48 | 5.6 | 0 | 2 | 0 | 0 | 0 | 0 | 0 | 0 | 0 | 0 | 0 | 0 | 0 | 0 | 1 | 3 |
|  | 1.12 | 0 | 0 | 0 | 0 | 0 | 0 | 0 | 0 | 0 | 0 | 0 | 0 | 0 | 0 | 0 | 0 |
| 49 | 5.6 | 2 | 3 | 3 | 3 | 3 | 0 | 3 | 3 | 3 | 3 | 3 | 2 | 3 | 3 | 3 | 3 |
|  | 1.12 | 0 | 3 | 3 | 3 | 3 | 0 | 3 | 2 | 2 | 3 | 3 | 2 | 3 | 3 | 3 | 3 |
|  | 0.28 | 0 | 2 | 3 | 3 | 0 | 0 | 0 | 0 | 1 | 1 | 1 | 1 | 3 | 3 | 3 | 3 |
|  | 0.056 | 0 | 0 | 0 | 0 | 0 | 0 | 0 | 0 | 0 | 0 | 0 | 0 | 0 | 0 | 0 | 0 |
|  | 0.0112 | 0 | 0 | 0 | 0 | 0 | 0 | 0 | 0 | 0 | 0 | 0 | 0 | 0 | 0 | 0 | 0 |
| 50 | 5.6 | 0 | 2 | 1 | 1 | 1 | 0 | 0 | 0 | 0 | 2 | 0 | 0 | 2 | 2 | 2 | 3 |
|  | 1.12 | 0 | 1 | 1 | 1 | 0 | 0 | 0 | 0 | 0 | 0 | 0 | 0 | 0 | 0 | 2 | 2 |
| 51 | 5.6 | 1 | 3 | 3 | 3 | 3 | 3 | 3 | 2 | 3 | 3 | 3 | 3 | 3 | 3 | 3 | 3 |
|  | 1.12 | 0 | 3 | 3 | 3 | 3 | 3 | 3 | 1 | 2 | 3 | 3 | 1 | 3 | 3 | 3 | 3 |
|  | 0.28 | 0 | 1 | 0 | 0 | 0 | 3 | 0 | 0 | 0 | 0 | 0 | 0 | 0 | 2 | 2 | 3 |
| 52 | 5.6 | 2 | 3 | 3 | 3 | 3 | 2 | 3 | 2 | 2 | 3 | 3 | 3 | 3 | 3 | 3 | 3 |
|  | 1.12 | 0 | 3 | 3 | 2 | 2 | 0 | 3 | 1 | 1 | 3 | 3 | -2 | 3 | 3 | 3 | 3 |
|  | 0.28 | 0 | 2 | 1 | 0 | 0 | 0 | 0 | 0 | 1 | 0 | 0 | 1 | 2 | 3 | 3 | 3 |
|  | 0.056 | 0 | 0 | 0 | 0 | 0 | 0 | 0 | 0 | 0 | 0 | 0 | 0 | 0 | 0 | 0 | 1 |
| 53 | 5.6 | 2 | 3 | 3 | 3 | 3 | 1 | 3 | 3 | 3 | 3 | 3 | 3 | 3 | 3 | 3 | 3 |
|  | 1.12 | 1 | 2 | 3 | 2 | 3 | 0 | 3 | 3 | 2 | 2 | 2 | 3 | 3 | 3 | 3 | 3 |
|  | 0.28 | 0 | 2 | 1 | 2 | 3 | 0 | 2 | 1 | 1 | 3 | 2 | 1 | 2 | 3 | 3 | 3 |
|  | 0.056 | 0 | 0 | 0 | 0 | 0 | 0 | 0 | 0 | 0 | 0 | 0 | 0 | 0 | 0 | 0 | 1 |
| 54 | 5.6 | 3 | 3 | 3 | 3 | 3 | 2 | 3 | 3 | 3 | 3 | 3 | 3 | 3 | 3 | 3 | 3 |
|  | 1.12 | 2 | 3 | 3 | 3 | 3 | 2 | 3 | 3 | 3 | 3 | 3 | 3 | 3 | 3 | 3 | 3 |
|  | 0.28 | 2 | 2 | 3 | 2 | 3 | 1 | 2 | 1 | 1 | 2 | 2 | 0 | 3 | 3 | 3 | 3 |
|  | 0.056 | 0 | 1 | 0 | 0 | 0 | 0 | 0 | 0 | 1 | 1 | 1 | 1 | 0 | 1 | 0 | 2 |
|  | 0.0112 | 0 | 0 | 0 | 0 | 0 | 0 | 0 | 0 | 0 | 0 | 0 | 0 | 0 | 0 | 0 | 0 |
| 55 | 5.6 | 2 | 3 | 3 | 3 | 3 | 2 | 3 | 3 | 3 | 3 | 3 | 2 | 3 | 3 | 3 | 3 |

TABLE 6-continued
PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 3 | 3 | 3 | 3 | 3 | 3 | 2 | 2 | 3 | 3 | 1 | 3 | 3 | 3 | 3 |
| | 0.28 | 0 | 2 | 0 | 1 | 2 | 0 | 1 | 0 | 1 | 2 | 2 | 1 | 2 | 2 | 2 | 3 |
| | 0.056 | 0 | 1 | 0 | 0 | 0 | 0 | 0 | 0 | 0 | 2 | 2 | 0 | 0 | 0 | 0 | 0 |
| 56 | 5.6 | 3 | 3 | 3 | 3 | 3 | 2 | 3 | 3 | 3 | 3 | 3 | 3 | 3 | 3 | 3 | 3 |
| | 1.12 | 3 | 2 | 3 | 3 | 3 | 1 | 3 | 3 | 3 | 3 | 3 | 3 | 3 | 3 | 3 | 3 |
| | 0.28 | 0 | 1 | 0 | 3 | 3 | 0 | 3 | 1 | 2 | 3 | 3 | 2 | 3 | 3 | 3 | 3 |
| | 0.056 | 0 | 0 | 0 | 0 | 1 | 0 | 0 | 0 | 0 | 0 | 0 | 0 | 0 | 3 | 1 | 3 |
| | 0.0112 | 0 | 0 | 0 | 0 | 0 | 0 | 0 | 0 | 0 | 0 | 0 | 0 | 0 | 0 | 0 | 0 |
| 57 | 5.6 | 0 | 1 | 0 | 0 | 3 | 0 | 0 | 1 | 0 | 1 | 1 | 1 | 3 | 3 | 3 | 3 |
| | 1.12 | 0 | 0 | 0 | 0 | 0 | 0 | 0 | 0 | 0 | N | 0 | 0 | 0 | 0 | 0 | 2 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 58 | 5.6 | 0 | 2 | 3 | 3 | 3 | 0 | 3 | 1 | 2 | 3 | 3 | 2 | 3 | 3 | 3 | 3 |
| | 1.12 | 0 | 1 | 0 | 0 | 0 | 2 | 0 | 2 | 0 | 0 | 0 | 0 | 1 | 2 | 2 | 2 |
| | 0.28 | 0 | 0 | 0 | 0 | 0 | 0 | 0 | 0 | 0 | 0 | 0 | 0 | 0 | 0 | 0 | 0 |
| 59 | 5.6 | 0 | 2 | 1 | 1 | 3 | 0 | 2 | 2 | 1 | 3 | 2 | 2 | 1 | 2 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 60 | 5.6 | 0 | 3 | 3 | 3 | 3 | 3 | 3 | 3 | 3 | 3 | 3 | 3 | 3 | 3 | 3 | 3 |
| | 1.12 | 1 | 3 | 3 | 3 | 3 | 3 | 3 | 3 | 3 | 3 | 3 | 3 | 3 | 3 | 3 | 3 |
| | 0.28 | 0 | 3 | 1 | 2 | 3 | 0 | 3 | 1 | 2 | 3 | 3 | 1 | 3 | 3 | 3 | 3 |
| | 0.056 | 0 | 2 | 0 | 0 | 2 | 0 | 0 | 0 | 2 | 2 | 0 | 1 | 2 | 2 | 2 | 3 |
| 61 | 5.6 | 0 | 3 | 0 | 0 | 3 | 0 | 3 | 2 | 2 | 3 | 2 | 1 | 3 | 3 | 3 | 3 |
| | 1.12 | 0 | 0 | 0 | 0 | 0 | 0 | 0 | 0 | 2 | 2 | 2 | 0 | 0 | 1 | 0 | 2 |
| | 0.28 | 0 | 0 | 0 | 0 | 0 | 0 | 0 | 0 | 0 | 0 | 0 | 0 | 0 | 0 | 0 | 0 |
| 62 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 3 | 3 | 3 | 2 | 3 | 2 | 2 | 3 | 3 | 2 | 3 | 3 | 3 | 3 |
| | 0.28 | 0 | 2 | 0 | 0 | 3 | 0 | 2 | 0 | 0 | 0 | 0 | 0 | 3 | 3 | 3 | 3 |
| | 0.28 | 0 | 1 | 0 | 0 | 0 | 0 | 0 | 0 | 0 | 1 | 0 | 0 | 1 | 3 | 3 | 3 |
| | 0.056 | 0 | 0 | 0 | 0 | 0 | 0 | 0 | 0 | 0 | 0 | 0 | 0 | 0 | 0 | 0 | 2 |
| 63 | 5.6 | 3 | 3 | 3 | 3 | 3 | 2 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | 0.28 | 0 | 3 | 2 | 3 | 3 | 0 | 3 | 2 | 3 | 3 | 3 | 2 | 3 | 3 | 3 | 3 |
| | 0.056 | 0 | 2 | 1 | 1 | 3 | N | 3 | 1 | 1 | 2 | 2 | 0 | 3 | 3 | 3 | 3 |
| | 0.0112 | 0 | 0 | 0 | 0 | 2 | 0 | 2 | 0 | 0 | 0 | 0 | 0 | 0 | 1 | 0 | 2 |
| 64 | 5.6 | 0 | 1 | 0 | 0 | 3 | 0 | 0 | 0 | 0 | 0 | 0 | 0 | 0 | 1 | 2 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 65 | 5.6 | 3 | 3 | 3 | 3 | 3 | 2 | 3 | 3 | 3 | 3 | 3 | 3 | 3 | 3 | 3 | 3 |
| | 1.12 | 0 | 1 | 1 | 0 | 3 | N | 3 | 3 | 1 | 2 | 1 | 1 | 3 | 3 | 3 | 3 |
| | 0.28 | 0 | 0 | 0 | 0 | 0 | 0 | 0 | 0 | 0 | 0 | 0 | 0 | 0 | 0 | 1 | 2 |
| | 0.056 | 0 | 0 | 0 | 0 | 0 | 0 | 0 | 0 | 0 | 0 | 0 | 0 | 0 | 0 | 0 | 0 |
| 66 | 5.6 | 3 | 3 | 3 | 3 | 3 | 2 | 3 | 3 | 3 | 3 | 3 | 3 | 3 | 3 | 3 | 3 |
| | 1.12 | 2 | 3 | 3 | 3 | 3 | 0 | 3 | 2 | 3 | 3 | 3 | 3 | 3 | 3 | 3 | 3 |
| | 0.28 | 0 | 2 | 1 | 3 | 3 | N | 3 | 1 | 1 | 2 | 2 | 2 | 3 | 3 | 3 | 3 |
| | 0.056 | 0 | 3 | 0 | 0 | 3 | 0 | 2 | 0 | 1 | 1 | 1 | 0 | 2 | 1 | 1 | 3 |
| | 0.0112 | 0 | 0 | 0 | 0 | 0 | 0 | 0 | 0 | 0 | 0 | 0 | 0 | 0 | 0 | 0 | 0 |
| 69 | 5.6 | 0 | 3 | 3 | 3 | 3 | 0 | 3 | 3 | 3 | 3 | 3 | 3 | 3 | 3 | 3 | 3 |
| | 1.12 | 0 | 3 | 3 | 3 | 3 | 3 | 3 | 2 | 3 | 3 | 2 | 3 | 3 | 3 | 3 | 3 |
| | 0.28 | 2 | 2 | 0 | 0 | 2 | 0 | 2 | 0 | 0 | 3 | 2 | 1 | 1 | 1 | 3 | 3 |
| 70 | 5.6 | 2 | 3 | 3 | 3 | 3 | 2 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 1 | 3 | 1 | 3 | 3 | 0 | 3 | 0 | 1 | 3 | 3 | 1 | 3 | 3 | 3 | 3 |
| | 0.056 | 0 | 0 | 0 | 1 | 2 | 0 | 0 | 0 | 0 | 1 | 0 | 0 | 0 | 0 | 0 | 2 |
| 71 | 5.6 | 2 | 3 | 3 | 3 | 3 | 0 | 2 | 2 | 3 | 3 | 3 | 3 | 3 | 3 | 3 | 3 |
| | 1.12 | 1 | 3 | 3 | 3 | 3 | 0 | 2 | 0 | 2 | 3 | 3 | 2 | 2 | 3 | 3 | 3 |
| | 0.28 | 0 | 0 | 0 | 0 | 0 | 0 | 0 | 0 | 2 | 1 | 0 | 0 | 0 | 1 | 0 | 2 |
| | 0.056 | 0 | 0 | 0 | 0 | 0 | 0 | 0 | 0 | 0 | 0 | 0 | 0 | 0 | 0 | 0 | 0 |
| 72 | 5.6 | 0 | 3 | 3 | 3 | 3 | 0 | 3 | 3 | 3 | 3 | 3 | 3 | 3 | 3 | 3 | 3 |
| | 1.12 | 0 | 0 | 3 | 3 | 3 | 0 | 2 | 3 | 3 | 3 | 3 | 3 | 3 | 3 | 3 | 3 |
| | 0.28 | 0 | 3 | 3 | 3 | 0 | 0 | 0 | 2 | 3 | 3 | 3 | 2 | 2 | 2 | 3 | 3 |
| | 0.056 | 0 | 2 | 0 | 0 | 0 | 0 | 0 | 0 | 2 | 2 | 1 | 0 | 1 | 2 | 2 | 3 |
| 73 | 5.6 | 0 | 3 | 3 | 3 | 3 | 0 | 3 | 3 | 3 | 3 | 3 | 3 | 3 | 3 | 3 | 3 |
| | 1.12 | 0 | 3 | 2 | 2 | 1 | 0 | 2 | 2 | 1 | 3 | 1 | 0 | 2 | 2 | 3 | 3 |
| | 0.28 | 0 | 0 | 0 | 0 | 0 | 0 | N | 0 | 0 | 0 | 0 | 0 | 0 | 0 | 0 | 3 |
| | 0.056 | 0 | 0 | 0 | 0 | 0 | 0 | 0 | 0 | 0 | 0 | 0 | 0 | 0 | 0 | 0 | 0 |
| 74 | 5.6 | 3 | 3 | 3 | 3 | 3 | 0 | 3 | 3 | 3 | 3 | 3 | 3 | 3 | 3 | 3 | 3 |
| | 1.12 | 1 | 3 | 3 | 3 | 3 | 2 | 2 | 2 | 3 | 3 | 3 | 2 | 3 | 3 | 3 | 3 |
| | 0.28 | 0 | 2 | 0 | 3 | 3 | 0 | 0 | 1 | 2 | 2 | 2 | 0 | 0 | 2 | 3 | 3 |
| | 0.056 | 0 | 0 | 0 | 0 | 0 | 0 | 0 | 0 | 0 | 0 | 0 | 0 | 0 | 0 | 1 | 0 |
| 75 | 5.6 | 3 | 3 | 0 | 0 | 0 | 0 | 2 | 1 | 1 | 2 | 2 | 2 | 3 | 1 | 2 | 3 |
| | 1.12 | 0 | 0 | 0 | 0 | 0 | 0 | 0 | 0 | 0 | 0 | 0 | 0 | 0 | 0 | 1 | 2 |
| | 0.28 | 0 | 0 | 0 | 0 | 0 | 0 | 0 | 0 | 0 | 0 | 0 | 0 | 0 | 0 | 0 | 0 |
| 76 | 5.6 | 3 | 3 | 3 | 3 | 3 | 2 | 3 | 3 | 3 | 3 | 3 | 3 | 3 | 3 | 3 | 3 |
| | 1.12 | 2 | 3 | 3 | 3 | 3 | 1 | 3 | 3 | 3 | 3 | 1 | 3 | 3 | 3 | 3 | 3 |
| | 0.28 | 0 | 3 | 1 | 2 | 3 | 0 | 2 | 1 | 2 | 2 | 2 | 1 | 3 | 3 | 3 | 3 |
| | 0.056 | 0 | 2 | 0 | 1 | 3 | 0 | 2 | 1 | 0 | 2 | 1 | 0 | 1 | 3 | 3 | 3 |
| | 0.0112 | 0 | 0 | 0 | 0 | 0 | 0 | 0 | 0 | 0 | 0 | 0 | 0 | 0 | 0 | 0 | 2 |
| 77 | 5.6 | 3 | 3 | 3 | 3 | 3 | 1 | 3 | 3 | 3 | 3 | 3 | 2 | 3 | 3 | 3 | 3 |

TABLE 6-continued

PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 3 | 0 | 3 | 3 | 1 | 3 | 2 | 1 | 3 | 2 | 0 | 3 | 3 | 3 | 3 |
| | 0.28 | 0 | 2 | 0 | 1 | 3 | 0 | 2 | 1 | 1 | 2 | 2 | 0 | 2 | 2 | 3 | 3 |
| | 0.056 | 0 | 0 | 0 | 0 | 0 | 0 | 0 | 0 | 0 | 0 | 0 | 0 | 0 | 0 | 0 | 0 |
| 78 | 5.6 | 0 | 3 | 1 | 1 | 2 | 0 | 2 | 2 | 0 | 3 | 2 | 1 | 3 | 3 | 3 | 3 |
| | 1.12 | 0 | 1 | 0 | 0 | 0 | 0 | 0 | 0 | 0 | 0 | 0 | 0 | 2 | 2 | 1 | 2 |
| | 0.28 | 0 | 0 | 0 | 0 | 0 | 0 | 0 | 0 | 0 | 0 | 0 | 0 | 0 | 0 | 0 | 0 |
| 79 | 5.6 | 2 | 3 | 3 | 3 | 3 | 0 | 3 | 3 | 3 | 3 | 3 | 3 | 3 | 3 | 3 | 3 |
| | 1.12 | 0 | 3 | 1 | 0 | 3 | 0 | 2 | 0 | 0 | 3 | 2 | 0 | 2 | 3 | 3 | 3 |
| | 0.28 | 0 | 1 | 0 | 0 | 0 | 0 | 0 | 0 | 0 | 0 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | 0 |
| 80 | 5.6 | 2 | 3 | 3 | 3 | 3 | 0 | 3 | 3 | 3 | 3 | 3 | 3 | 3 | 3 | 3 | 3 |
| | 1.12 | 0 | 3 | 0 | 2 | 3 | 0 | 3 | 3 | 2 | 3 | 3 | 1 | 3 | 3 | 3 | 3 |
| | 0.28 | 0 | 2 | 0 | 0 | 1 | 0 | 0 | 0 | 0 | 0 | 0 | 0 | 0 | 2 | 3 | 3 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 81 | 5.6 | 1 | 3 | 3 | 3 | 3 | 0 | 3 | 3 | 3 | 3 | 3 | 3 | 3 | 3 | 3 | 3 |
| | 1.12 | 0 | 3 | 0 | 3 | 3 | 0 | 2 | 1 | 2 | 3 | 2 | 1 | 3 | 3 | 3 | 3 |
| | 0.28 | 0 | 2 | 0 | 0 | 0 | 0 | 2 | 0 | 0 | 1 | 0 | 0 | 1 | 2 | 3 | 3 |
| | 0.56 | 0 | 1 | 0 | 0 | 0 | 0 | 1 | 0 | 0 | 0 | 0 | 0 | 0 | 0 | 0 | 0 |
| 82 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 1 | 3 | 3 | 0 | 3 | 2 | 3 | 3 | 2 | 3 | 3 | 3 | 3 | 3 |
| | 0.28 | 0 | 2 | 0 | 2 | 2 | 0 | 2 | 0 | 1 | 1 | 0 | 0 | 2 | 3 | 3 | 3 |
| | 0.056 | 0 | 0 | 0 | 0 | 0 | 0 | 0 | 0 | 0 | 0 | 0 | 0 | 0 | 0 | 0 | 0 |
| 85 | 5.6 | 0 | 3 | 3 | 2 | 3 | 0 | 3 | 1 | 3 | 3 | 3 | 3 | 3 | 3 | 3 | 3 |
| | 1.12 | 0 | 3 | 0 | 2 | 1 | 0 | 1 | 0 | 2 | 3 | 2 | 1 | 2 | 2 | 3 | 3 |
| | 0.28 | 0 | 0 | 0 | 0 | 0 | 0 | 0 | 0 | 0 | 0 | 0 | 0 | 0 | 0 | 2 | 1 |
| | 0.056 | 0 | 0 | 0 | 0 | 0 | 0 | 0 | 0 | 0 | 0 | 0 | 0 | 0 | 0 | 0 | 0 |
| 87 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 1 | 3 | 0 | 2 | 3 | 0 | 1 | 3 | 3 | 3 | 2 | 1 | 2 | 3 | 3 | 3 |
| | 0.056 | 0 | 1 | 0 | 0 | 0 | 0 | 0 | 0 | 0 | 0 | 1 | 0 | 1 | 1 | 1 | 2 |
| 89 | 5.6 | 0 | 3 | 3 | 2 | 3 | 0 | 3 | 2 | 2 | 3 | 3 | 3 | 3 | 3 | 3 | 3 |
| | 1.12 | 0 | 0 | 0 | 0 | 0 | 0 | 0 | 0 | 0 | 0 | 0 | 0 | 0 | 0 | 1 | 2 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 90 | 5.6 | 3 | 3 | 3 | 3 | 3 | 0 | 3 | 3 | 3 | 3 | 3 | 3 | 3 | 3 | 3 | 3 |
| | 1.12 | 0 | 2 | 1 | 0 | 0 | 0 | 0 | 2 | 1 | 2 | 1 | 1 | 1 | 3 | 3 | 3 |
| | 0.28 | 0 | 1 | 0 | 0 | 0 | 0 | 0 | 0 | 0 | 0 | 0 | 0 | 1 | 2 | 2 | 3 |
| 91 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 2 | 3 | 3 | 3 | 3 | 3 | 3 | 3 | 3 |
| | 0.28 | 0 | 2 | 1 | 0 | 3 | 0 | 2 | 1 | 1 | 2 | 2 | 1 | 3 | 3 | 3 | 3 |
| | 0.056 | 0 | 0 | 0 | 0 | 0 | 0 | 0 | 0 | 1 | 1 | 0 | 0 | 0 | 0 | 0 | 2 |
| 92 | 5.6 | 1 | 2 | 2 | 3 | 3 | 0 | 2 | 2 | 3 | 3 | 2 | 1 | 3 | 3 | 3 | 3 |
| | 1.12 | 0 | 2 | 0 | 0 | 0 | 0 | 0 | 0 | 0 | 0 | 0 | 0 | 0 | 3 | 3 | 3 |
| | 0.28 | 0 | 2 | 0 | 0 | 0 | 0 | 0 | 0 | 0 | 0 | 0 | 0 | 0 | 0 | 0 | 1 |
| 93 | 5.6 | 3 | 3 | 3 | 3 | 3 | 0 | 3 | 3 | 3 | 3 | 3 | 3 | 3 | 3 | 3 | 3 |
| | 1.12 | 1 | 2 | 3 | 3 | 3 | 3 | 3 | 3 | 3 | 3 | 2 | 2 | 3 | 3 | 3 | 3 |
| | 0.28 | 0 | 3 | 1 | 1 | 2 | 1 | 0 | 0 | 0 | 0 | 0 | 0 | 3 | 3 | 3 | 3 |
| | 0.056 | 0 | 0 | 0 | 0 | 0 | 0 | 0 | 0 | 0 | 0 | 0 | 0 | 0 | 0 | 0 | 2 |
| 94 | 5.6 | 0 | 2 | 1 | 1 | 0 | 0 | 0 | 1 | 1 | 3 | 2 | 1 | 3 | 2 | 3 | 3 |
| | 1.12 | 0 | 0 | 0 | 0 | 0 | 0 | 0 | 0 | 0 | 0 | 0 | 0 | 0 | 0 | 0 | 3 |
| | 0.28 | 0 | 0 | 0 | 0 | 0 | 0 | 0 | 0 | 0 | 0 | 0 | 0 | 0 | 0 | 0 | 0 |
| 95 | 5.6 | 0 | 2 | 1 | 2 | 2 | 0 | 1 | 2 | 1 | 2 | 2 | 1 | 2 | 3 | 3 | 3 |
| | 1.12 | 0 | 1 | 0 | 0 | 0 | 0 | 0 | 0 | 0 | 0 | 0 | 0 | 1 | 2 | 3 | 3 |
| | 0.28 | 0 | 0 | 0 | 0 | 0 | 0 | 0 | 0 | 1 | 0 | 0 | 0 | 0 | 0 | 0 | 0 |
| 96 | 5.6 | 0 | 3 | 2 | 3 | 3 | 0 | 3 | 3 | 3 | 3 | 3 | 1 | 3 | 3 | 3 | 3 |
| | 1.12 | 1 | 2 | 0 | 2 | 3 | N | 2 | 2 | 3 | 3 | 3 | 1 | 3 | 3 | 3 | 3 |
| | 0.28 | 0 | 0 | 0 | 0 | 0 | N | 0 | 0 | 0 | 0 | 0 | 0 | 0 | 0 | 0 | 1 |
| | 0.056 | 0 | 0 | 0 | 0 | 0 | N | 0 | 0 | 0 | 3 | 3 | 1 | 1 | 2 | 2 | 3 |
| | 0.28* | 0 | 0 | 0 | 0 | 0 | 0 | 0 | 0 | 0 | 0 | 0 | 0 | 0 | 2 | 1 | 2 |
| | 0.056* | 0 | 0 | 0 | 0 | 0 | 0 | 0 | 0 | 0 | 0 | 0 | 0 | 0 | 0 | 0 | 0 |
| 98 | 5.6 | 0 | 1 | 0 | 0 | 0 | 0 | 0 | 0 | 1 | 3 | 2 | 1 | 1 | 2 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 1 | 0 | 0 | 0 | 0 | 0 | 0 | 0 |
| 100 | 5.6 | 0 | 3 | 3 | 0 | 3 | 0 | 1 | 2 | 2 | 3 | 2 | 2 | 1 | 3 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 102 | 5.6 | 0 | 2 | 1 | 1 | 1 | 0 | 0 | 2 | 2 | 2 | 1 | 1 | 0 | 3 | 3 | 3 |
| | 1.12 | 0 | 0 | 0 | 0 | 0 | 0 | 0 | 0 | 0 | 0 | 0 | 0 | 0 | 0 | 0 | 1 |
| | 0.28 | 0 | 0 | 0 | 0 | 0 | 0 | 0 | 0 | 0 | 0 | 0 | 0 | 0 | 0 | 0 | 0 |
| 108 | 5.6 | 0 | 0 | 0 | 0 | 0 | N | 0 | 0 | 0 | 0 | 0 | 0 | 0 | 1 | 3 | 3 |
| | 1.12 | 0 | 0 | 0 | 0 | 0 | N | 0 | 0 | 0 | 0 | 0 | 0 | 0 | 0 | 0 | 1 |
| | 0.28 | 0 | 0 | 0 | 0 | 0 | N | 0 | 0 | 0 | 0 | 0 | 0 | 0 | 0 | 0 | 0 |
| 109 | 5.6 | 0 | 0 | 0 | 0 | 3 | N | 2 | 2 | 1 | 3 | 3 | 0 | 3 | 3 | 3 | 3 |
| | 1.12 | 0 | 0 | 0 | 0 | 0 | N | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 110 | 5.6 | 0 | 1 | 0 | 0 | 2 | N | 0 | 1 | 1 | 1 | 1 | 1 | 2 | 3 | 3 | 3 |
| | 1.12 | 0 | 0 | 0 | 0 | 0 | 0 | 0 | 0 | 0 | 0 | 0 | 0 | 0 | 0 | 1 | 1 |
| | 0.28 | 0 | 0 | 0 | 0 | 0 | 0 | 0 | 0 | 0 | 0 | 0 | 0 | 0 | 0 | 0 | 0 |

TABLE 6-continued
PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 111 | 5.6 | 0 | 1 | 1 | 0 | 1 | 0 | 0 | 0 | 0 | 0 | 0 | 0 | 0 | 3 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | N | 0 | 0 | 0 | 0 | 0 | 0 | 0 | 0 | 0 | 0 |
| 112 | 5.6 | 0 | 3 | 3 | 3 | 3 | N | 3 | 3 | 3 | 3 | 3 | 3 | 3 | 3 | 3 | 3 |
| | 1.12 | 0 | 2 | 1 | 2 | 2 | N | 2 | 3 | 2 | 3 | 2 | 2 | 3 | 2 | 3 | 3 |
| | 0.28 | 0 | 0 | 0 | 0 | 0 | N | 0 | 0 | 0 | 0 | 0 | 0 | 0 | 0 | 0 | 2 |
| | 0.056 | 0 | 0 | 0 | 0 | 0 | N | 0 | 0 | 0 | 0 | 0 | 0 | 0 | 0 | 0 | 0 |
| 113 | 5.6 | 0 | 1 | 3 | 2 | 1 | 0 | 2 | 2 | 3 | 3 | 3 | 2 | 3 | 3 | 3 | 3 |
| | 1.12 | 0 | 1 | 0 | 0 | 0 | 0 | 0 | 0 | 1 | 0 | 0 | 0 | 0 | 0 | 2 | 2 |
| | 0.28 | 0 | 0 | 0 | 0 | 0 | N | 0 | 0 | 0 | 0 | 0 | 0 | 0 | 0 | 0 | 0 |
| | 0.056 | 0 | 0 | 0 | 0 | 0 | N | 0 | 0 | 0 | 0 | 0 | 0 | 0 | 0 | 0 | 0 |
| 114 | 5.6 | 3 | 3 | 3 | 3 | 3 | 3 | 3 | 3 | 3 | 3 | 3 | 3 | 3 | 3 | 3 | 3 |
| | 1.12 | 0 | 3 | 3 | 3 | 3 | 0 | 3 | 2 | 3 | 3 | 3 | 3 | 3 | 3 | 3 | 3 |
| | 0.28 | 0 | 1 | 0 | 0 | 2 | 0 | 0 | 1 | 1 | 2 | 1 | 1 | 0 | 3 | 3 | 0 |
| | 0.056 | 0 | 0 | 0 | 0 | 0 | N | 0 | 0 | 0 | 0 | 0 | 0 | 0 | 0 | 0 | 0 |
| 115 | 5.6 | 0 | 3 | 1 | 3 | 2 | 1 | 2 | 1 | 2 | 3 | 1 | 2 | 2 | 3 | 3 | 3 |
| | 1.12 | 0 | 1 | 0 | 0 | 0 | 0 | 0 | 0 | 0 | 0 | 0 | 0 | 0 | 2 | 3 | 2 |
| | 0.28 | 0 | 0 | 0 | 0 | 0 | 0 | 0 | 0 | 0 | 0 | 0 | 0 | 0 | 0 | 0 | 0 |
| 116 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | 0.28 | 1 | 3 | 0 | 2 | 3 | 0 | 1 | 1 | 1 | 2 | 2 | 1 | 1 | 3 | 3 | 3 |
| | 0.056 | 0 | 0 | 0 | 0 | 0 | 0 | 0 | 0 | 0 | 0 | 0 | 0 | 0 | 1 | 1 | 2 |
| | 0.0112 | 0 | 0 | 0 | 0 | 0 | 0 | 0 | 0 | 0 | 0 | 0 | 0 | 0 | 0 | 0 | 0 |
| 117 | 5.6 | 2 | 3 | 3 | 3 | 3 | 2 | 3 | 3 | 3 | 3 | 2 | 2 | 3 | 3 | 3 | 3 |
| | 1.12 | 0 | 1 | 2 | 2 | 2 | 0 | 0 | 0 | 1 | 2 | 1 | 1 | 3 | 3 | 3 | 3 |
| | 0.28 | 0 | 0 | 0 | 0 | 0 | 0 | 0 | 0 | 0 | 0 | 0 | 0 | 0 | 1 | 2 | 3 |
| | 0.056 | 0 | 0 | 0 | 0 | 0 | N | 0 | 0 | 0 | 0 | 0 | 0 | 0 | 0 | 0 | 0 |
| 118 | 5.6 | 3 | 3 | 3 | 3 | 3 | 3 | 3 | 3 | 3 | 3 | 3 | 2 | 3 | 3 | 3 | 3 |
| | 1.12 | 0 | 1 | 2 | 1 | 2 | 1 | 1 | 0 | 1 | 1 | 0 | 0 | 2 | 1 | 3 | 3 |
| | 0.28 | 0 | 0 | 0 | 0 | 0 | 0 | 0 | 0 | 0 | 0 | 0 | 0 | 0 | 0 | 2 | 3 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | N | 0 | 0 | 0 | 0 | 0 | 0 | 0 | 0 | 0 | 0 |
| 119 | 5.6 | 3 | 3 | 3 | 3 | 3 | 0 | 3 | 3 | 3 | 3 | 3 | 3 | 3 | 3 | 3 | 3 |
| | 1.12 | 0 | 2 | 3 | 2 | 3 | 0 | 2 | 3 | 3 | 3 | 2 | 3 | 1 | 3 | 3 | 3 |
| | 0.28 | 0 | 0 | 0 | 0 | 0 | 0 | 0 | 0 | 0 | 0 | 0 | 0 | 0 | 3 | 3 | 3 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 120 | 5.6 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| 121 | 5.6 | 3 | 3 | 3 | 0 | 3 | 3 | 0 | 3 | 3 | 3 | 3 | 3 | 3 | 3 | 3 | 3 |
| | 1.12 | 0 | 3 | 3 | 1 | 3 | 0 | 3 | 3 | 2 | 3 | 2 | 1 | 3 | 3 | 3 | 3 |
| | 0.28 | 0 | 1 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 122 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | 0.28 | 0 | 3 | 0 | 2 | 3 | 0 | 2 | 1 | 2 | 3 | 2 | 1 | 3 | 3 | 3 | 3 |
| | 0.056 | 0 | 0 | 0 | 0 | 0 | 0 | 0 | 0 | 0 | 0 | 0 | 0 | 1 | 1 | 2 | 2 |
| | 0.0112 | 0 | 0 | 0 | 0 | 0 | 0 | 0 | 0 | 0 | 0 | 0 | 0 | 0 | 0 | 0 | 0 |
| 123 | 5.6 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | 0 | 0 | 0 | 0 | 0 | 0 | 0 | 0 | 0 | 0 | 0 |
| 124 | 5.6 | 0 | 2 | 1 | 2 | 3 | 0 | 3 | 2 | 2 | 3 | 3 | 2 | 3 | 3 | 3 | 3 |
| | 1.12 | 0 | 0 | 0 | 0 | 0 | 0 | 0 | 0 | 0 | 0 | 0 | 0 | 3 | 2 | 2 | 3 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | N | 0 | 0 | 0 | 0 | 0 | 0 | 0 | 0 | 0 | 0 |
| 125 | 5.6 | 0 | 3 | 3 | 2 | 3 | 0 | 3 | 3 | 3 | 3 | 3 | 3 | 3 | 3 | 3 | 3 |
| | 1.12 | 0 | 0 | 0 | 0 | 0 | 0 | 0 | 0 | 0 | 2 | 2 | 1 | 1 | 3 | 3 | 3 |
| | 0.28 | 0 | 0 | 0 | 0 | 0 | 0 | 0 | 0 | 0 | 0 | 0 | 0 | 0 | 0 | 0 | 0 |
| 126 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 2 | 1 | 3 | 0 | 2 | 2 | 2 | 3 | 3 | 2 | 3 | 3 | 3 | 3 |
| | 0.28 | 0 | 3 | 0 | 0 | 0 | 0 | 0 | 3 | 3 | 2 | 2 | 1 | 2 | 3 | 3 | 3 |
| | 0.056 | 0 | 0 | 0 | 0 | 0 | 0 | 0 | 0 | 0 | 0 | 0 | 0 | 0 | 1 | 1 | 2 |
| | 0.0112 | 0 | 0 | 0 | 0 | 0 | 0 | 0 | 0 | 0 | 0 | 0 | 0 | 0 | 1 | 0 | 1 |
| 127 | 5.6 | 3 | 3 | 3 | 3 | 3 | 3 | 3 | 3 | 3 | 3 | 3 | 3 | 3 | 3 | 3 | 3 |
| | 1.12 | 0 | 3 | 0 | 1 | 3 | 3 | 2 | 1 | 2 | 3 | 2 | 2 | 1 | 3 | 3 | 3 |
| | 0.28 | 0 | 0 | 0 | 0 | 0 | 3 | 0 | 0 | 0 | 0 | 0 | 0 | 0 | 1 | 2 | 2 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | N | 0 | 0 | 0 | 0 | 0 | 0 | 0 | 0 | 0 | 0 |
| | 5.6* | 3 | 3 | 3 | 3 | 3 | 0 | 3 | 3 | 3 | 3 | 3 | 3 | 3 | 3 | 3 | 3 |
| | 1.12* | 0 | 3 | 0 | 1 | 3 | 0 | 3 | 3 | 2 | 3 | 2 | 1 | 2 | 3 | 3 | 3 |
| | 0.28* | 0 | 0 | 0 | 0 | 0 | 0 | 0 | 0 | 0 | 0 | 0 | 0 | 0 | 0 | 1 | 2 |
| 128 | 5.6 | 0 | 2 | 2 | 2 | 3 | 0 | 0 | 0 | 1 | 3 | 2 | 1 | 3 | 3 | 3 | 3 |
| | 1.12 | 0 | 2 | 0 | 0 | 0 | 0 | 0 | 0 | 0 | 2 | 2 | 1 | 1 | 3 | 3 | 3 |
| | 0.28 | 0 | 3 | 3 | 1 | 3 | 0 | 2 | 1 | 2 | 3 | 3 | 1 | 3 | 3 | 3 | 3 |
| 130 | 5.6 | 3 | 3 | 3 | 3 | 3 | 0 | 3 | 3 | 3 | 3 | 3 | 3 | 3 | 3 | 3 | 3 |
| | 1.12 | 1 | 3 | 1 | 1 | 3 | 0 | 3 | 3 | 3 | 3 | 3 | 3 | 3 | 3 | 3 | 3 |
| | 0.28 | 0 | 1 | 0 | 1 | 1 | 0 | 3 | 0 | 0 | 3 | 2 | 0 | 3 | 2 | 2 | 3 |
| | 0.056 | 0 | 0 | 0 | 1 | 0 | 0 | 0 | 0 | 0 | 1 | 1 | 0 | 0 | 0 | 0 | 1 |
| 131 | 5.6 | 0 | 2 | 0 | 0 | 0 | 0 | 1 | 1 | 1 | 3 | 3 | 2 | 1 | 3 | 3 | 3 |
| | 1.12 | 0 | 0 | 0 | 0 | 0 | 0 | 0 | 0 | 0 | 0 | 0 | 1 | 0 | 0 | 0 | 3 |

TABLE 6-continued
PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 0.28 | 0 | 0 | 0 | 0 | 0 | 0 | 0 | 0 | 0 | 0 | 0 | 0 | 0 | 0 | 0 | 0 |
| 136 | 5.6 | 0 | 0 | 1 | 1 | 0 | 0 | 1 | 0 | 1 | 2 | 2 | 0 | 2 | 1 | 3 | 3 |
| | 1.12 | 0 | 1 | 1 | 0 | 0 | 0 | 1 | 0 | 0 | 1 | 1 | 0 | 1 | 0 | 0 | 3 |
| | 0.28 | 0 | 0 | 0 | 0 | 0 | 0 | 0 | 0 | 0 | 0 | 0 | 0 | 0 | 0 | 0 | 3 |
| 137 | 5.6 | 2 | 3 | 3 | 3 | 3 | 0 | 3 | 3 | 3 | 3 | 3 | 3 | 3 | 3 | 3 | 3 |
| | 1.12 | 0 | 3 | 3 | 1 | 3 | 0 | 3 | 1 | 2 | 3 | 3 | 2 | 3 | 3 | 3 | 3 |
| | 0.28 | 0 | 0 | 0 | 0 | 0 | 0 | 0 | 0 | 0 | 0 | 0 | 1 | 3 | 2 | 3 | 3 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 138 | 5.6 | 0 | 0 | 0 | 0 | 0 | 0 | 0 | 0 | 0 | 0 | 0 | 0 | 0 | 0 | 0 | 0 |
| | 1.12 | 0 | 0 | 0 | 0 | 0 | N | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 139 | 5.6 | 0 | 3 | 0 | 1 | 3 | 0 | 3 | 3 | 3 | 3 | 3 | 3 | 3 | 3 | 3 | 3 |
| | 1.12 | 0 | 2 | 0 | 0 | 0 | 0 | 1 | 1 | 1 | 2 | 2 | 1 | 0 | 0 | 2 | 2 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 140 | 5.6 | 3 | 3 | 3 | 3 | 3 | 0 | 3 | 3 | 3 | 3 | 3 | 3 | 3 | 3 | 3 | 3 |
| | 1.12 | 0 | 3 | 2 | 2 | 3 | 0 | 3 | 3 | 3 | 3 | 3 | 3 | 2 | 3 | 3 | 3 |
| | 0.28 | 1 | 2 | 0 | 1 | 1 | 0 | 3 | 1 | 2 | 3 | 3 | 2 | 3 | 3 | 3 | 3 |
| | 0.056 | 0 | 1 | 0 | 0 | 0 | 0 | 0 | 3 | 3 | 3 | 1 | 1 | 0 | 1 | 1 | 3 |
| | 0.0112 | 0 | 0 | 0 | 0 | 0 | 0 | 0 | 0 | 0 | 0 | 0 | 0 | 0 | 0 | 0 | 0 |
| 141 | 5.6 | 1 | 3 | 3 | 3 | 3 | 0 | 3 | 2 | 3 | 3 | 3 | 3 | 3 | 3 | 3 | 3 |
| | 1.12 | 0 | 3 | 3 | 3 | 2 | 0 | 0 | 0 | 3 | 3 | 3 | 2 | 3 | 3 | 3 | 3 |
| | 0.28 | 0 | 2 | 0 | 1 | 0 | 0 | 0 | 0 | 2 | 3 | 2 | 0 | 0 | 0 | 3 | 3 |
| | 0.056 | 0 | 0 | 0 | 0 | 0 | 0 | 0 | 0 | 0 | 1 | 0 | 0 | 0 | 0 | 1 | 3 |
| 144 | 5.6 | 1 | 2 | 2 | 2 | 3 | N | 2 | 1 | 2 | 3 | 3 | 2 | 3 | 3 | 3 | 3 |
| | 1.12 | 0 | 0 | 0 | 0 | 0 | 0 | 0 | 0 | 0 | 0 | 0 | 0 | 0 | 0 | 2 | 2 |
| | 0.28 | 0 | 0 | 0 | 0 | 0 | 0 | 0 | 0 | 0 | 0 | 0 | 0 | 0 | 0 | 0 | 0 |
| 145 | 5.6 | 0 | 3 | 1 | 1 | 1 | 0 | 3 | 0 | 3 | 3 | 3 | 1 | 3 | 3 | 3 | 3 |
| | 1.12 | 0 | 1 | 1 | 0 | 0 | 0 | 0 | 0 | 0 | 0 | 0 | 0 | 1 | 0 | 1 | 3 |
| | 0.28 | 0 | 0 | 0 | 0 | 0 | 0 | 0 | 0 | 0 | 0 | 0 | 0 | 0 | 0 | 0 | 2 |
| 149 | 5.6 | 0 | 2 | 3 | 1 | 1 | 0 | 0 | 0 | 0 | 2 | 3 | 2 | 2 | 1 | 3 | 3 |
| | 1.12 | 0 | 1 | 1 | 0 | 0 | 0 | 0 | 0 | 0 | 1 | 2 | 0 | 2 | 1 | 3 | 3 |
| | 0.28 | 0 | 2 | 0 | 0 | 0 | 0 | 0 | 0 | 0 | 0 | 0 | 0 | 0 | 0 | 1 | 3 |
| | 0.056 | 0 | 0 | 1 | 0 | 0 | 0 | 0 | 0 | 0 | 0 | 1 | 2 | 0 | 0 | 0 | 1 |
| 156 | 5.6 | 0 | 2 | 3 | 2 | 2 | 0 | 2 | 0 | 1 | 3 | 3 | 1 | 2 | 3 | 3 | 3 |
| | 1.12 | 0 | 1 | 0 | 0 | 0 | 0 | 1 | 0 | 0 | 0 | 0 | 0 | 0 | 1 | 3 | 3 |
| | 0.28 | 0 | 0 | 0 | 0 | 0 | 0 | 0 | 0 | 0 | 0 | 0 | 0 | 0 | 0 | 0 | 0 |
| 165 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | 0.28 | 0 | 3 | 1 | 3 | 3 | N | 3 | 1 | 2 | 3 | 2 | 1 | 3 | 3 | 3 | 3 |
| | 0.056 | 0 | 0 | 0 | 0 | 1 | 0 | 0 | 0 | 0 | 0 | 0 | 0 | 1 | 2 | 2 | 2 |
| 166 | 5.6 | 3 | 3 | 3 | 3 | 3 | 3 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 3 | 3 | 3 | 3 | 3 | 3 |
| | 0.28 | 0 | 2 | 3 | 3 | 3 | 0 | 3 | 0 | 2 | 2 | 2 | 1 | 3 | 3 | 3 | 3 |
| | 0.056 | 0 | 0 | 0 | 0 | 0 | N | 0 | 0 | 1 | 0 | 0 | 0 | 0 | 0 | 0 | 2 |
| | 0.0112 | 0 | 0 | 0 | 0 | 0 | N | 0 | 0 | 0 | 0 | 0 | 0 | 0 | 0 | 0 | 0 |
| 167 | 5.6 | 2 | 3 | 3 | 3 | 3 | 1 | 3 | 3 | 3 | 3 | 3 | 3 | 3 | 3 | 3 | 3 |
| | 1.12 | 0 | 0 | 0 | 1 | 1 | 0 | 0 | 0 | 0 | 2 | 2 | 1 | 0 | 1 | 2 | 3 |
| | 0.28 | 0 | 0 | 0 | 0 | 0 | 0 | 0 | 0 | 0 | 0 | 0 | 0 | 0 | 1 | 0 | 0 |
| | 0.056 | 0 | 0 | 0 | 0 | 0 | 0 | 0 | 0 | 0 | 0 | 0 | 0 | 0 | 0 | 0 | 0 |
| 168 | 5.6 | 0 | 0 | 0 | 0 | 0 | 0 | 0 | 0 | 0 | 0 | 0 | 0 | 0 | 0 | 0 | 2 |
| | 1.12 | 0 | 0 | 0 | 0 | 0 | 0 | 0 | 0 | 0 | 0 | 0 | 0 | 0 | 0 | 0 | 0 |
| 170 | 5.6 | 0 | 1 | 0 | 0 | 1 | 0 | 2 | 0 | 0 | 2 | 2 | 1 | 1 | 1 | 1 | 3 |
| | 1.12 | 0 | 0 | 0 | 0 | 0 | 0 | 0 | 0 | 0 | 0 | 0 | 0 | 0 | 0 | 0 | 1 |
| | 0.28 | 0 | 0 | 0 | 1 | 0 | 0 | 0 | 0 | 0 | 0 | 0 | 0 | 0 | 0 | 0 | 0 |
| 172 | 5.6 | 3 | 3 | 3 | 3 | 3 | 3 | 3 | 3 | 3 | 3 | 3 | 3 | 3 | 3 | 3 | 3 |
| | 1.12 | 0 | 2 | 0 | 1 | 3 | 0 | 1 | 2 | 2 | 3 | 1 | 1 | 3 | 3 | 3 | 3 |
| | 0.28 | 0 | 1 | 0 | 0 | 1 | 0 | 0 | 0 | 0 | 0 | 0 | 1 | 1 | 1 | 1 | 2 |
| | 0.056 | 0 | 0 | 0 | 0 | 0 | N | 0 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 174 | 5.6 | 0 | 2 | 0 | 1 | 3 | 0 | 3 | 2 | 1 | 3 | 2 | 0 | 3 | 3 | 3 | 3 |
| | 1.12 | 0 | 0 | 0 | 0 | 1 | 0 | 1 | 0 | 0 | 1 | 0 | 0 | 0 | 0 | 0 | 0 |
| | 0.28 | 0 | 0 | 0 | 1 | 0 | N | 0 | 0 | 0 | 0 | 0 | 0 | 0 | 0 | 0 | 0 |
| | 0.056 | 0 | 0 | 0 | 0 | 0 | N | 0 | 0 | 0 | 0 | 0 | 0 | 0 | 0 | 0 | 0 |
| 175 | 5.6 | 3 | 3 | 3 | 3 | 3 | 2 | 3 | 3 | 3 | 3 | 3 | 3 | 3 | 3 | 3 | 3 |
| | 1.12 | 0 | 3 | 2 | 3 | 3 | 1 | 3 | 2 | 2 | 3 | 3 | 1 | 3 | 3 | 3 | 3 |
| | 0.28 | 0 | 2 | 2 | 2 | 3 | 1 | 2 | 1 | 1 | 3 | 2 | 0 | 3 | 3 | 3 | 3 |
| | 0.056 | 0 | 2 | 0 | 1 | 2 | 0 | 0 | N | 0 | 0 | 0 | 0 | 0 | 1 | 2 | 3 |
| | 0.0112 | 0 | 0 | 0 | 1 | 1 | 0 | 0 | 1 | 1 | 0 | 0 | 0 | 0 | 0 | 1 | 2 |
| 178 | 5.6 | 3 | 3 | 3 | 3 | 3 | 2 | 3 | 3 | 3 | 3 | 3 | 3 | 3 | 3 | 3 | 3 |
| | 1.12 | 2 | 3 | 3 | 3 | 3 | 0 | 3 | 3 | 2 | 3 | 3 | 2 | 3 | 3 | 3 | 3 |
| | 0.28 | 0 | 2 | 2 | 3 | 2 | 0 | 2 | 2 | 2 | 2 | 3 | 2 | 3 | 3 | 3 | 3 |
| | 0.056 | 0 | 0 | 0 | 3 | 0 | 0 | 0 | 1 | 1 | 1 | 2 | 0 | 1 | 2 | 3 | 3 |
| | 0.0112 | 0 | 0 | 0 | 1 | 2 | 0 | 1 | 1 | 1 | 0 | 0 | 0 | 2 | 1 | 1 | 1 |
| 183 | 5.6 | 0 | 3 | 3 | 2 | 3 | 0 | 3 | 1 | 2 | 3 | 3 | 1 | 3 | 3 | 3 | 3 |
| | 1.12 | 0 | 2 | 2 | 2 | 1 | 0 | 2 | 0 | 2 | 3 | 3 | 1 | 2 | 3 | 3 | 3 |
| | 0.28 | 0 | 1 | 1 | 1 | 0 | 0 | 1 | 0 | 0 | 2 | 1 | 0 | 0 | 2 | 3 | 3 |
| | 0.056 | 0 | 2 | 0 | 1 | 0 | 0 | 1 | 0 | 0 | 0 | 0 | 0 | 2 | 0 | 1 | 2 |
| 185 | 5.6 | 1 | 3 | 3 | 3 | 3 | 3 | 3 | 3 | 3 | 3 | 3 | 3 | 3 | 3 | 3 | 3 |

TABLE 6-continued

PRE-EMERGENT HERBICIDE ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 0 | 0 | 0 | 2 | 3 | 0 | 3 | 1 | 1 | 3 | 2 | 1 | 3 | 3 | 3 | 3 |
| | 0.28 | 0 | 0 | 0 | 0 | 2 | 0 | 3 | 0 | 0 | 2 | 1 | 0 | 2 | 3 | 2 | 3 |
| | 0.056 | 0 | 0 | 0 | 0 | 0 | 0 | 1 | 0 | 0 | 0 | 0 | 0 | 0 | 0 | 0 | 0 |
| 188 | 5.6 | 3 | 3 | 3 | 3 | 3 | 0 | 3 | 3 | 3 | 3 | 3 | 2 | 3 | 3 | 3 | 3 |
| | 1.12 | 3 | 3 | 3 | 3 | 3 | 0 | 3 | 3 | 2 | 3 | 3 | 2 | 3 | 3 | 3 | 3 |
| | 0.28 | 0 | 3 | 2 | 2 | 3 | 0 | 3 | 2 | 2 | 3 | 3 | 1 | 3 | 3 | 3 | 3 |
| | 0.056 | 0 | 1 | 1 | 0 | 0 | 1 | 0 | 0 | 3 | 1 | 0 | 2 | 2 | 2 | 3 | 0 |
| | 0.0112 | 0 | 0 | 0 | 0 | 0 | 0 | 0 | 0 | 0 | 0 | 0 | 0 | 0 | 0 | 0 | 2 |
| 189 | 1.12 | 0 | 0 | 0 | 0 | 0 | 0 | 0 | 0 | 1 | 3 | 0 | 0 | 2 | 0 | 0 | 3 |
| | 0.28 | 0 | 0 | 0 | 0 | 0 | 0 | 0 | 0 | 0 | 1 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | 0 |
| 190 | 5.6 | 3 | 3 | 3 | 3 | 3 | 1 | 3 | 3 | 3 | 3 | 3 | 3 | 3 | 3 | 3 | 3 |
| | 1.12 | 1 | 3 | 1 | 3 | 3 | 0 | 3 | 2 | 2 | 3 | 3 | 2 | 3 | 3 | 3 | 3 |
| | 0.28 | 0 | 1 | 1 | 3 | 3 | 0 | 2 | 1 | 2 | 3 | 3 | 2 | 3 | 3 | 3 | 3 |
| | 0.056 | 0 | 1 | 0 | 2 | 2 | 0 | 1 | 0 | 0 | 3 | 1 | 0 | 2 | 1 | 3 | 3 |
| | 0.0112 | 0 | 0 | 0 | 0 | 0 | 0 | 0 | 0 | 0 | 0 | 0 | 0 | 0 | 0 | 0 | 3 |
| 191 | 5.6 | 1 | 0 | 0 | 0 | 0 | 0 | 2 | 1 | 0 | 2 | 1 | 0 | 1 | 0 | 0 | 0 |
| | 1.12 | 0 | 0 | 0 | 0 | 0 | 0 | 0 | 0 | 0 | 0 | 0 | 0 | 0 | 0 | 0 | 0 |
| 192 | 5.6 | 3 | 3 | 2 | 3 | 3 | 0 | 3 | 3 | 3 | 3 | 3 | 3 | 3 | 3 | 3 | 3 |
| | 1.12 | 0 | 3 | 1 | 3 | 3 | 0 | 3 | 3 | 3 | 3 | 3 | 2 | 3 | 3 | 3 | 3 |
| | 0.28 | 0 | 2 | 1 | 2 | 2 | 0 | 3 | 2 | 1 | 3 | 3 | 2 | 3 | 3 | 3 | 3 |
| | 0.056 | 0 | 0 | 0 | 1 | 0 | 0 | 0 | 0 | 0 | 2 | 1 | 0 | 1 | 1 | 3 | 3 |
| | 0.0112 | 0 | 0 | 0 | 1 | 0 | 0 | 0 | 0 | 0 | 0 | 0 | 0 | 1 | 1 | 0 | 0 |
| 193 | 5.6 | 0 | 1 | 0 | 1 | 2 | 0 | 2 | 1 | 1 | 3 | 2 | 1 | 1 | 1 | 2 | 3 |
| | 1.12 | 0 | 0 | 0 | 0 | 2 | 0 | 0 | 1 | 0 | 1 | 1 | 0 | 0 | 1 | 1 | 2 |
| | 0.28 | 0 | 0 | 0 | 0 | 1 | 0 | 0 | 0 | 0 | 0 | 0 | 0 | 0 | 0 | 1 | 1 |
| 194 | 5.6 | 2 | 3 | 2 | 2 | 2 | 0 | 3 | 3 | 3 | 3 | 3 | 2 | 2 | 3 | 3 | 3 |
| | 1.12 | 2 | 2 | 2 | 2 | 2 | 0 | 3 | 3 | 3 | 3 | 3 | 2 | 2 | 3 | 3 | 3 |
| | 0.28 | 1 | 2 | 0 | 1 | 1 | 0 | 3 | 2 | 2 | 3 | 3 | 1 | 1 | 3 | 3 | 3 |
| | 0.056 | 0 | 1 | 0 | 0 | 1 | 0 | 1 | 2 | 2 | 2 | 1 | 0 | 0 | 3 | 3 | 3 |
| 195 | 5.6 | 3 | 3 | 3 | 3 | 3 | 2 | 3 | 3 | 3 | 3 | 3 | 3 | 3 | 3 | 3 | 3 |
| | 1.12 | 2 | 3 | 3 | 3 | 3 | 0 | 3 | 3 | 3 | 3 | 2 | 3 | 3 | 3 | 3 | 3 |
| | 0.28 | 0 | 2 | 2 | 2 | 3 | 0 | 3 | 3 | 2 | 3 | 3 | 2 | 3 | 3 | 3 | 3 |
| | 0.056 | 0 | 0 | 0 | 1 | 2 | 0 | 3 | 2 | 2 | 3 | 1 | 0 | 3 | 3 | 3 | 3 |
| | 0.0112 | 0 | 1 | 0 | 1 | 0 | 0 | 0 | 1 | 0 | 2 | 0 | 0 | 0 | 1 | 1 | 3 |
| 209 | 5.6 | 0 | 1 | 0 | 1 | 0 | 0 | 2 | 1 | 0 | 2 | 1 | 0 | 1 | 2 | 2 | 1 |
| | 1.12 | 0 | 1 | 0 | 0 | 0 | 0 | 0 | 0 | 1 | 1 | 0 | 2 | 1 | 1 | 1 | 2 |
| | 0.28 | 0 | 0 | 0 | 0 | 0 | 0 | 0 | 0 | 0 | 0 | 0 | 0 | 0 | 0 | 0 | 1 |
| | 0.056 | 0 | 0 | 0 | 0 | 0 | 0 | 0 | 0 | 0 | 0 | 0 | 0 | 0 | 0 | 0 | N |
| | 0.0112 | 0 | 0 | 0 | 0 | 0 | 0 | 0 | 0 | 0 | 0 | 0 | 0 | 0 | 0 | 0 | 0 |
| 210 | 5.6 | 3 | 3 | 3 | 3 | 3 | 1 | 3 | 3 | 3 | 3 | 3 | 3 | 3 | 3 | 3 | 3 |
| | 1.12 | 0 | 3 | 3 | 3 | 3 | 0 | 3 | 2 | 2 | 3 | 3 | 1 | 3 | 3 | 3 | 3 |
| | 0.28 | 0 | 1 | 2 | 2 | 3 | 0 | 3 | 1 | 1 | 3 | 1 | 0 | 3 | 3 | 3 | 3 |
| | 0.056 | 0 | 0 | 0 | 0 | 0 | 0 | 0 | 0 | 0 | 0 | 0 | 2 | 1 | 1 | 1 | 1 |
| | 0.0112 | 0 | 0 | 0 | 0 | 0 | 0 | 0 | 0 | 0 | 0 | 0 | 0 | 0 | 0 | 0 | 1 |
| 216 | 5.6 | 1 | 3 | 3 | 2 | 3 | 0 | 3 | 3 | 3 | 3 | 3 | 3 | 3 | 3 | 3 | 3 |
| | 1.12 | 0 | 2 | 2 | 1 | 2 | 0 | 1 | 1 | 1 | 3 | 3 | 0 | 3 | 3 | 3 | 3 |
| | 0.28 | 0 | 1 | 0 | 1 | 0 | 0 | 0 | 0 | 1 | 1 | 1 | 0 | 1 | 2 | 3 | 3 |
| | 0.056 | 0 | 0 | 1 | 1 | 0 | 0 | 0 | 0 | 0 | 0 | 0 | 0 | 0 | 0 | 0 | 3 |
| | 0.0112 | 0 | 0 | 1 | 1 | 0 | 0 | 0 | 0 | 0 | 0 | 0 | 0 | 0 | 0 | 0 | 2 |

*Retest

The above tables illustrate one aspect of the present invention, that is, the use of the compounds of the invention to kill or injure undesirable plants, e.g., weeds.

The herbicidal composition of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid or organic origin, water, a wetting agent, a dispersing agent, an emulsifying agent or any suitable combination of theses.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan) and polyoxyethylene derivatives of castor oil. Preferred dispersants are methyl cellulose, polyvinyl alcohol, sodium lignin sulfonates, polyoxyethylene/polyoxypropylene block copolymers, polymeric alkyl naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, bentonite, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include chlorinated solvents dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

HETEROCYCLIC NITROGEN/SULFUR DERIVATIVES

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-α:2',1'-c)-pyrazidiinium salt
5-Bromo-3-isopropyl-6-methyluracil
1,1'-Dimethyl-4,4'-bipyridinium
3-methyl-4-amino-6-phenyl-1,2,4-triazin-5-(4H)one
2-(4-chloro-6-ethylamino-1,3,5-S-2-triazinylamino)-2-methylpropionitrile
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate
3-cyclohexyl-6-dimethylamino-1-methyl-1,3,5-triazine-2,4(1H,3H)-dione
4-amino-6-(tert-butyl)-3-methylthio-1,2,4-triazin-5(4H)one
5-amino-4-chloro-2-phenyl-3(1H)-pyridazinone
5-methylamino-4-chloro-2-(α,α,α-trifluoro-m-tolyl)-3(2H)-pyridazinone
5-bromo-3-(sec-butyl)-6-methyluracil

UREAS

N-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
2-Chloro-N[(4-methoxy-6-methyl), 3,5-triazin-2-yl)aminocarbonyl]-benzenesulfonamide
N-(3-trifluoromethylphenyl)-N,N'-dimethylurea
3-(3,4-dichlorophenyl)-1-methoxy-1-methylurea
Methyl 2-(((((4,6-dimethyl-2-pyrimidinyl)amino)-carbonyl)amino)sulfonyl)benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)amino-carbonyl)amino sulfonyl methyl)benzoate
Methyl 2-(((((4-methoxy-6-methyl-1,3,5-triazin-2-yl)amino)carbonyl)amino)sulfonyl)benzoate

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate
Ethyl dipropylthiolcarbamate

ACETAMIDES/ACETANILIDES/ANILINES/AMIDES

2-Chloro-N,N-diallylacetamide
N,N-dimethyl-2,2-diphenylacetamide
N-(2,4-dimethyl-5-[[(trifluoromethyl)sulfonyl]amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide
α,α,α-Trifluoro-2,6-dinitro-N-propyl-N-(2-chloroethyl)-p-toluidine
3,5-Dinitro-4-dipropylamino-benzenesulfonamide
N-(1-ethylpropyl)-3,4-dimethyl-2,6-dinitro-benzenamine

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts
Potassium 4-amino-3,5,6-trichloropicolinate
2,3-Dihydro-3,3-dimethyl-2-ethoxy-5-benzofuranyl methanesulfonate

ETHERS 2,4-Dichlorophenyl-4-nitrophenyl ether
2-Chloro-δ,δ,δ-trifluoro-p-tolyl-3-ethoxy-4-nitrodiphenyl ether
methyl 2-[4-(2,4-dichlorophenoxy)phenoxy]propanoate
butyl 2[4-[(5-(trifluoromethyl)-2-pyridinyl)oxy]-phenoxy]propanoate
5-(2-chloro-4-trifluromethylphenoxy)-N-methyl sulfonyl 2-nitrobenzamide
1'-(Carboethoxy)ethyl 5-[2-chloro-4-(trifluoromethyl)-phenoxy]-2-nitrobenzoate

MISCELLANEOUS 2,6-Dichlorobenzonitrile
Monosodium acid methanearsonate
Disodium methanearsonate
2-(2-chlorophenyl)methyl-4,4-dimethyl-3-isoxazoli dinone
7-oxabicyclo (2.2.1) heptane, 1-methyl-4-(1-methyl ethyl)-2-(2-methylphenylmethoxy)-, exo- Fertizilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | I. Emulsifiable Concentrates | Weight Percent |
|---|---|---|
| A. | Compound of Example 57 | 45.15 |
| | Monochlorobenzene | 44.85 |
| | Ethoxylated nonylphenyl (e.g., Flo Mo 30N, a registered trademark of Sellers Corp.) | 1.7 |
| | Mixture of calcium sulfonyl benzenesulfonate, ethoxylated castor oil, and ethoxylated nonylphenol (e.g., Flo Mo LHF, a registered trademark of Sellers Corp.) | 8.3 |
| | | 100.0 |
| B. | Compound of Example No. 13 | 11.0 |
| | Free acid of complex organic phosphate or aromatic or aliphatic hydrophobe base (e.g., GAFAC RE-610, a registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | C9 aromatics | 5.34 |
| | Monochlorobenzene | 76.96 |
| | | 100.00 |
| C. | Compound of Example No. 16 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |
| | II. Flowables | |
| A. | Compound of Example No. 47 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 74 | 45.0 |
| | Methyl cellulose | .3 |
| | Silica aerogel | 1.5 |
| | Sodium lignosulfonate | 3.5 |
| | Sodium N-methyl-N-oleyl turate | 2.0 |
| | Water | 47.7 |
| | | 100.00 |
| | III. Wettable Powders | |
| A. | Compound of Example No. 94 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example No. 116 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 83 | 10.0 |
| | Sodium lignosulfonate | 3.0 |
| | Sodium N-methyl-N-oleyl-taurate | 1.0 |
| | Kaolinite clay | 86.0 |
| | | 100.00 |
| | IV. Dusts | |
| A. | Compound of Example No. 67 | 2.0 |
| | Attapulgite | 98.0 |
| | | 100.00 |
| B. | Compound of Example No. 21 | 60.0 |
| | Montmorillonite | 40.0 |
| | | 100.00 |
| C. | Compound of Example No. 50 | 30.0 |
| | Ethylene glycol | 1.0 |
| | Bentonite | 69.0 |

I. Emulsifiable Concentrates

| | | Weight Percent |
|---|---|---|
| | | 100.00 |
| D. | Compound of Example No. 22 | 1.0 |
| | Diatomaceous earth | 99.0 |
| | | 100.00 |

V. Granules

| | | |
|---|---|---|
| A. | Compound of Example No. 57 | 5.36 |
| | Granules | 94.64 |
| | | 100.00 |
| B. | Compound of Example No. 23 | 15.0 |
| | Granular attapulgite (20/40 mesh) | 85.0 |
| | | 100.00 |
| C. | Compound of Example No. 44 | 30.0 |
| | Diatomaceous earth (20/40) | 70.0 |
| | | 100.00 |
| D. | Compound of Example No. 66 | 1.0 |
| | Ethylene glycol | 5.0 |
| | Methylene blue | 0.1 |
| | Pyrophyllite | 93.9 |
| | | 100.00 |
| E. | Compound of Example No. 111 | 5.0 |
| | Pyrophyllite (20/40) | 95.0 |
| | | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

What is claimed is:

1. A compound represented by the formula $$\text{Ra} \underset{R_2}{\overset{X}{\diagdown}} \underset{N}{\diagup} \overset{O}{\underset{R_1}{\diagdown}} \text{C-ZR}$$

wherein:
R is selected from the group consisting of hydrogen, lower alkyl, lower alkenyl, lower alkynyl, cyanoalkyl, alkoxyalkyl, haloalkyl, haloalkenyl, benzyl, and a cation, and Z is selected from O and S;

$R_1$ and $R_2$ are independently selected from fluorinated methyl, chlorofluorinated methyl, fluorinated ethyl, and lower alkyl provided that $R_1$ and $R_2$ cannot both be lower alkyl radicals;

Ra is selected from:

$$\overset{O}{\underset{}{\overset{\|}{C}}}\text{ZR}'$$

radicals wherein R' is selected from hydrogen, lower alkyl, lower alkenyl, lower alkynyl, cyanoalkyl, alkoxyalkyl, haloalkyl, haloalkenyl, benzyl and a cation; and;

X is $-S(O)_nR_6$ in which n is an integer from 0-2 inclusive and $R_6$ is selected from lower alkyl, lower alkenyl, lower alkynyl, $C_3$-$C_6$ cycloalkyl, $C_3$-$C_6$ cycloalkylalkyl, haloalkyl, phenyl and phenylalkyl optionally substituted with one or more of halogen, nitro, lower alkyl, lower alkoxy, lower haloalkyl, lower haloalkoxy, and carboalkoxy radicals.

2. A compound according to claim 1 wherein Ra is selected from $$-\overset{O}{\underset{}{\overset{\|}{C}}}-\text{ZR}'$$

3. A compound according to claim 2 wherein R and R' are the same or different lower alkyl radicals.

4. A compound according to claim 3 wherein one of the $R_1$ and $R_2$ is $-CF_3$ and the other is $-CF_2H$.

5. A compound according to claim 4 wherein n is zero and $R_6$ is lower alkyl.

6. A compound according to claim 5 wherein $R_6$ is isopropyl.

7. A compound according to claim 5 wherein $R_6$ is ethyl.

8. A compound according to claim 3 wherein $R_1$ is $-CF_3$ and $R_2$ is $-CF_3$.

9. A compound according to claim 8 wherein n is zero and $R_6$ is lower alkyl.

10. A compound according to claim 9 wherein $R_6$ is isopropyl.

11. A compound according to claim 9 wherein $R_6$ is ethyl.

12. A compound according to claim 3 wherein $R_1$ is $-CF_3$ and $R_2$ is $-CF_2Cl$.

13. A compound according to claim 12 wherein n is zero and $R_6$ is lower alkyl.

14. A compound according to claim 13 wherein $R_6$ is isopropyl.

15. A compound according to claim 13 wherein $R_6$ is ethyl.

16. A compound according to claim 6 wherein R, and R' are independently selected from methyl and ethyl.

17. A compound according to claim 7 wherein R, and R' are independently selected from methyl and ethyl.

18. A herbicidal composition containing a carrier and a herbicidally effective amount of a compound represented by the formula

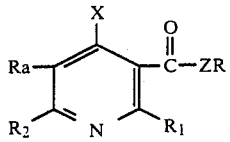

wherein:
R is selected from the group consisting of lower alkyl, lower alkenyl, lower alkynyl, cyanoalkyl, alkoxyalkyl, haloalkyl, haloalkenyl, and Z is selected from O and S;
$R_1$ and $R_2$ are independently selected from fluorinated methyl, chlorofluorinated methyl, fluorinated ethyl, and lower alkyl provided that $R_1$ and $R_2$ cannot both be lower alkyl radicals;
Ra is selected from:

radicals wherein R' is selected from lower alkyl, lower alkenyl, lower alkynyl, cyanoalkyl, alkoxyalkyl, haloalkyl, haloalkenyl and a cation; and;
X is $-S(O)_nR_6$ is which n is an integer from 0-2 inclusive and $R_6$ is selected from lower alkyl, lower alkenyl, lower alkynyl, $C_3-C_6$ cycloalkyl, $C_3-C_6$ cycloalkylalkyl, haloalkyl, phenyl and phenylalkyl optionally substituted with one or more of halogen, nitrol, lower alkyl, lower alkoxy, lower haloalkyl, lower haloalkoxy, and carboalkoxy radicals.

19. A composition according to claim 18 wherein Ra is selected from

20. A composition according to claim 19 wherein R, and R' are the same or different lower alkyl radicals.
21. A composition according to claim 20 wherein one of the $R_1$ and $R_2$ is $-CF_3$ and the other is $-CF_2H$.
22. A composition according to claim 21 wherein n is zero and $R_6$ is lower alkyl.
23. A composition according to claim 22 wherein $R_6$ is isopropyl.
24. A composition according to claim 22 wherein $R_6$ is ethyl.
25. A composition according to claim 20 wherein $R_1$ is $-CF_3$ and $R_2$ is $-CF_3$.
26. A compound according to claim 25 wherein n is zero and $R_6$ is lower alkyl.
27. A composition according to claim 26 wherein $R_6$ is isopropyl.
28. A composition according to claim 26 wherein $R_6$ is ethyl.
29. A composition according to claim 20 wherein $R_1$ is $-CF_3$ and $R_2$ is $-CF_2Cl$.
30. A compound according to claim 29 wherein n is zero and $R_6$ is lower alkyl.
31. A composition according to claim 30 wherein $R_6$ is isopropyl.
32. A composition according to claim 31 wherein $R_6$ is ethyl.
33. A composition according to claim 23 wherein R, and R' are independently selected from methyl and ethyl.
34. A composition according to claim 24 wherein R, and R' are independently selected from methyl and ethyl.
35. A method of controlling undesired vegetation comprising applying to the plant locus an effective amount of a compound represented by the formula

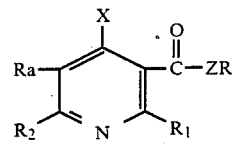

wherein:
R is selected from the group consisting of lower alkyl, lower alkenyl, lower alkynyl, cyanoalkyl, alkoxyalkyl, haloalkyl, and haloalkenyl; and Z is selected from O and S;
$R_1$ and $R_2$ are independently selected from fluorinated methyl, chlorofluorinated methyl, fluorinated ethyl, and lower alkyl provided that $R_1$ and $R_2$ cannot both be lower alkyl radicals;
Ra is selected from:

radicals wherein R' is selected from lower alkyl, lower alkenyl, lower alkynyl, cyanoalkyl, alkoxyalkyl, haloalkyl, haloalkenyl and a cation; and;
X is $-S(O)_nR_6$ is which n is an integer from 0-2 inclusive and $R_6$ is selected from lower alkyl, lower alkenyl, lower alkynyl, $C_3-C_6$ cycloalkyl, $C_3-C_6$ cycloalkylalkyl, haloalkyl, phenyl and phenylalkyl optionally substituted with one or more of halogen, nitro, lower alkyl, lower alkoxy, lower haloalkyl, lower haloalkoxy, and carboalkoxy radicals.

36. A method according to claim 35 wherein Ra is selected from

37. A method according to claim 36 wherein R, and R' are the same or different lower alkyl radicals.
38. A method according to claim 37 wherein one of the $R_1$ and $R_2$ is $-CF_3$ and the other is $-CF_2H$.
39. A method according to claim 38 wherein n is zero and $R_6$ is selected from ethyl and isopropyl.

* * * * *